United States Patent
Kishimoto

(10) Patent No.: US 10,335,395 B2
(45) Date of Patent: Jul. 2, 2019

(54) METHODS OF ADMINISTERING IMMUNOSUPPRESSANTS HAVING A SPECIFIED PHARMACODYNAMIC EFFECTIVE LIFE AND THERAPEUTIC MACROMOLECULES FOR THE INDUCTION OF IMMUNE TOLERANCE

(71) Applicant: Selecta Biosciences, Inc., Watertown, MA (US)

(72) Inventor: Takashi Kei Kishimoto, Lexington, MA (US)

(73) Assignee: Selecta Biosciences, Inc., Watertown, MA (US)

( * ) Notice: Subject to any disclaimer, the term of this patent is extended or adjusted under 35 U.S.C. 154(b) by 228 days.

(21) Appl. No.: 14/269,058

(22) Filed: May 2, 2014

(65) Prior Publication Data
US 2014/0328924 A1    Nov. 6, 2014

Related U.S. Application Data

(60) Provisional application No. 61/948,384, filed on Mar. 5, 2014, provisional application No. 61/948,313, filed on Mar. 5, 2014, provisional application No. 61/907,177, filed on Nov. 21, 2013, provisional application No. 61/881,851, filed on Sep. 24, 2013, provisional application No. 61/881,913, filed on Sep. 24, 2013, provisional application No. 61/881,921, filed on Sep. 24, 2013, provisional application No. 61/819,517, filed on May 3, 2013.

(51) Int. Cl.

| | | |
|---|---|---|
| *A61K 39/395* | (2006.01) | |
| *A61K 31/436* | (2006.01) | |
| *A61K 38/19* | (2006.01) | |
| *A61K 38/21* | (2006.01) | |
| *A61K 38/37* | (2006.01) | |
| *A61K 38/43* | (2006.01) | |
| *A61K 45/06* | (2006.01) | |
| *A61K 31/192* | (2006.01) | |
| *A61K 9/00* | (2006.01) | |
| *A61K 9/127* | (2006.01) | |
| *A61K 9/51* | (2006.01) | |
| *C07K 16/18* | (2006.01) | |
| *C07K 16/24* | (2006.01) | |
| *C07K 16/40* | (2006.01) | |
| *A61K 38/47* | (2006.01) | |
| *A61K 47/69* | (2017.01) | |
| *A61K 39/00* | (2006.01) | |

(52) U.S. Cl.
CPC .......... *A61K 31/436* (2013.01); *A61K 9/0019* (2013.01); *A61K 9/127* (2013.01); *A61K 9/5115* (2013.01); *A61K 9/5153* (2013.01); *A61K 9/5192* (2013.01); *A61K 31/192* (2013.01); *A61K 38/19* (2013.01); *A61K 38/21* (2013.01); *A61K 38/37* (2013.01); *A61K 38/43* (2013.01); *A61K 38/47* (2013.01); *A61K 39/3955* (2013.01); *A61K 39/39533* (2013.01); *A61K 45/06* (2013.01); *A61K 47/6923* (2017.08); *A61K 47/6929* (2017.08); *A61K 47/6935* (2017.08); *A61K 47/6937* (2017.08); *C07K 16/18* (2013.01); *C07K 16/241* (2013.01); *C07K 16/40* (2013.01); *A61K 2039/505* (2013.01); *C12Y 305/01001* (2013.01)

(58) Field of Classification Search
None
See application file for complete search history.

(56) References Cited

U.S. PATENT DOCUMENTS

| | | | |
|---|---|---|---|
| 5,100,669 | A | 3/1992 | Hyon et al. |
| 5,543,158 | A | 8/1996 | Gref et al. |
| 5,679,347 | A | 10/1997 | Porcelli et al. |
| 5,762,904 | A | 6/1998 | Okada et al. |
| 5,912,017 | A | 6/1999 | Mathiowitz et al. |
| 6,060,082 | A | 5/2000 | Chen et al. |
| 6,197,229 | B1 | 3/2001 | Ando et al. |
| 6,251,957 | B1 | 6/2001 | Wilson et al. |
| 6,306,640 | B1 | 10/2001 | Nicolette |
| 6,387,397 | B1 | 5/2002 | Chen et al. |
| 6,838,089 | B1 | 1/2005 | Carlsson et al. |
| 7,045,508 | B2 | 5/2006 | Scaria |
| 8,629,151 | B2 | 1/2014 | Zepp et al. |
| 8,652,487 | B2 | 2/2014 | Maldonado et al. |
| 8,865,487 | B2 | 10/2014 | Kostka et al. |

(Continued)

FOREIGN PATENT DOCUMENTS

| | | |
|---|---|---|
| CN | 101437491 A | 5/2009 |
| CN | 101646418 A | 2/2010 |

(Continued)

OTHER PUBLICATIONS

U.S. Appl. No. 12/788,260, filed May 26, 2010, Zepp et al.

(Continued)

*Primary Examiner* — Yunsoo Kim
(74) *Attorney, Agent, or Firm* — Wolf, Greenfield & Sacks, P.C.

(57) ABSTRACT

This invention relates to methods that provide immunosuppressants and therapeutic macromolecules that are administered within a pharmacodynamically effective window of the immunosuppressants to induce immune tolerance to the therapeutic macromolecules. The methods allow shifting the immune response in favor of tolerogenic immune response development specific to the therapeutic macromolecule.

20 Claims, 4 Drawing Sheets

(56) References Cited

U.S. PATENT DOCUMENTS

| | | |
|---|---|---|
| 9,005,665 B2 | 4/2015 | Gourapura |
| 9,006,254 B2 | 4/2015 | Zepp et al. |
| 9,017,697 B2 | 4/2015 | Thomas |
| 9,066,978 B2 | 6/2015 | Ilyinskii et al. |
| 9,276,815 B2* | 3/2016 | Anumala ............. H04L 41/083 |
| 9,289,476 B2* | 3/2016 | Kishimoto ............. A61K 39/00 |
| 9,289,477 B2* | 3/2016 | Fraser ................... A61K 39/00 |
| 9,295,718 B2* | 3/2016 | Fraser ................... A61K 39/00 |
| 9,764,031 B2 | 9/2017 | Ilyinskii et al. |
| 9,884,112 B2 | 2/2018 | Zepp et al. |
| 9,987,354 B2 | 6/2018 | Fraser et al. |
| 9,993,548 B2 | 6/2018 | Maldonado et al. |
| 9,994,443 B2 | 6/2018 | Zepp et al. |
| 10,004,802 B2 | 6/2018 | Kishimoto et al. |
| 10,039,822 B2 | 8/2018 | Altreuter et al. |
| 10,046,064 B2 | 8/2018 | Kishimoto |
| 10,071,114 B2 | 9/2018 | Kishimoto |
| 2002/0014242 A1 | 2/2002 | Scaria et al. |
| 2002/0019361 A1 | 2/2002 | Scaria |
| 2002/0086049 A1 | 7/2002 | Bolton et al. |
| 2002/0095135 A1 | 7/2002 | Meeker |
| 2004/0204379 A1 | 1/2004 | Cheng et al. |
| 2004/0038406 A1 | 2/2004 | Unger et al. |
| 2004/0043483 A1 | 3/2004 | Qian et al. |
| 2006/0002852 A1 | 1/2006 | Saltzman et al. |
| 2006/0002971 A1 | 1/2006 | Saltzman et al. |
| 2006/0147432 A1 | 7/2006 | Moore et al. |
| 2006/0210638 A1 | 9/2006 | Liversidge et al. |
| 2006/0222652 A1 | 10/2006 | Sebbel et al. |
| 2006/0251677 A1 | 11/2006 | Bachmann et al. |
| 2006/0251710 A1 | 11/2006 | Kwon et al. |
| 2006/0251711 A1 | 11/2006 | Konduri et al. |
| 2006/0269540 A1 | 11/2006 | Robert et al. |
| 2007/0110685 A1 | 5/2007 | Auspitz et al. |
| 2007/0254897 A1 | 11/2007 | Gjorstrup |
| 2008/0031899 A1 | 2/2008 | Reddy et al. |
| 2008/0145441 A1 | 6/2008 | Penades et al. |
| 2008/0160089 A1 | 7/2008 | Vitiello et al. |
| 2008/0254045 A1 | 10/2008 | Donda et al. |
| 2008/0311140 A1 | 12/2008 | Lee et al. |
| 2009/0004259 A1 | 1/2009 | Rabinovich et al. |
| 2009/0028910 A1 | 1/2009 | DeSimone et al. |
| 2009/0074828 A1 | 3/2009 | Alexis et al. |
| 2009/0082260 A1 | 3/2009 | Lamb et al. |
| 2009/0155292 A1 | 6/2009 | Santamaria et al. |
| 2009/0226525 A1 | 9/2009 | de los Rios et al. |
| 2010/0008932 A1 | 1/2010 | Bensussan et al. |
| 2010/0028450 A1 | 2/2010 | Vasu et al. |
| 2010/0055076 A1 | 3/2010 | Lim et al. |
| 2010/0055189 A1 | 3/2010 | Hubbell et al. |
| 2010/0062968 A1 | 3/2010 | Pulendran et al. |
| 2010/0068261 A1 | 3/2010 | Tamarkin et al. |
| 2010/0068286 A1 | 3/2010 | Troiano et al. |
| 2010/0069426 A1 | 3/2010 | Zale et al. |
| 2010/0080816 A1 | 4/2010 | Hadeiba et al. |
| 2010/0112077 A1 | 5/2010 | Desai et al. |
| 2010/0129392 A1 | 5/2010 | Shi et al. |
| 2010/0129439 A1 | 5/2010 | Alexis et al. |
| 2010/0151000 A1 | 6/2010 | Thomas et al. |
| 2010/0172994 A1 | 7/2010 | Sigmund et al. |
| 2010/0183602 A1 | 7/2010 | Carballido Herrera et al. |
| 2010/0183727 A1 | 7/2010 | Iannacone et al. |
| 2010/0196401 A1 | 8/2010 | Scaria |
| 2010/0233197 A1 | 9/2010 | Wakatsuki Pedersen et al. |
| 2010/0233251 A1 | 9/2010 | Von Andrian et al. |
| 2010/0273220 A1 | 10/2010 | Yanik et al. |
| 2010/0303850 A1 | 12/2010 | Lipford et al. |
| 2011/0004148 A1 | 1/2011 | Ishii et al. |
| 2011/0020388 A1 | 1/2011 | Zepp et al. |
| 2011/0027217 A1 | 2/2011 | Zepp et al. |
| 2011/0070153 A1 | 3/2011 | Hyde et al. |
| 2011/0070154 A1 | 3/2011 | Hyde et al. |
| 2011/0076273 A1 | 3/2011 | Adler et al. |
| 2011/0110965 A1 | 5/2011 | Fraser et al. |
| 2011/0171248 A1 | 7/2011 | Pittet et al. |
| 2011/0223201 A1 | 9/2011 | Lipford et al. |
| 2011/0262491 A1 | 10/2011 | Keegan et al. |
| 2011/0272836 A1 | 11/2011 | Keegan et al. |
| 2011/0293700 A1 | 12/2011 | Bratzler et al. |
| 2011/0293701 A1 | 12/2011 | Bratzler et al. |
| 2011/0293723 A1 | 12/2011 | Bratzler et al. |
| 2012/0014966 A1 | 1/2012 | Solinger et al. |
| 2012/0027806 A1 | 2/2012 | Ilyinskii et al. |
| 2012/0027808 A1 | 2/2012 | Iannacone et al. |
| 2012/0039989 A1 | 2/2012 | Hubbell et al. |
| 2012/0058153 A1 | 3/2012 | Ilyinskii et al. |
| 2012/0058154 A1 | 3/2012 | Ilyinskii et al. |
| 2012/0064110 A1 | 3/2012 | Ilyinskii et al. |
| 2012/0070493 A1 | 3/2012 | Fraser et al. |
| 2012/0076831 A1 | 3/2012 | Miller et al. |
| 2012/0077860 A1 | 3/2012 | Garcia |
| 2012/0114677 A1 | 5/2012 | Zepp et al. |
| 2012/0171229 A1 | 7/2012 | Zepp et al. |
| 2012/0244222 A1 | 9/2012 | Altreuter et al. |
| 2012/0276109 A1 | 11/2012 | Fraser et al. |
| 2012/0276133 A1 | 11/2012 | Maldonado et al. |
| 2012/0276134 A1* | 11/2012 | Fraser ................... A61K 39/00 424/193.1 |
| 2012/0276155 A1* | 11/2012 | Kishimoto ............. A61K 39/00 424/400 |
| 2012/0276156 A1* | 11/2012 | Fraser ................... A61K 39/00 424/400 |
| 2012/0276157 A1* | 11/2012 | Fraser ................... A61K 39/00 424/400 |
| 2012/0276158 A1* | 11/2012 | Fraser ................... A61K 39/00 424/400 |
| 2012/0276159 A1* | 11/2012 | Fraser ................... A61K 39/00 424/400 |
| 2012/0276160 A1 | 11/2012 | Maldonado et al. |
| 2012/0294888 A1 | 11/2012 | Kishimoto et al. |
| 2012/0301498 A1* | 11/2012 | Altreuter ................ A61K 39/00 424/193.1 |
| 2012/0301510 A1 | 11/2012 | Kishimoto et al. |
| 2012/0308563 A1 | 12/2012 | Arya et al. |
| 2013/0028857 A1 | 1/2013 | Gao et al. |
| 2013/0028941 A1 | 1/2013 | Altreuter et al. |
| 2013/0039954 A1 | 2/2013 | Pittet et al. |
| 2013/0058894 A1 | 3/2013 | Maldonado et al. |
| 2013/0058901 A1 | 3/2013 | Maldonado et al. |
| 2013/0058902 A1 | 3/2013 | Kishimoto et al. |
| 2013/0058963 A1 | 3/2013 | Maldonado et al. |
| 2013/0058970 A1 | 3/2013 | Kishimoto et al. |
| 2013/0058974 A1 | 3/2013 | Maldonado et al. |
| 2013/0058975 A1 | 3/2013 | Maldonado et al. |
| 2013/0058976 A1 | 3/2013 | Kishimoto et al. |
| 2013/0058977 A1 | 3/2013 | Maldonado et al. |
| 2013/0058978 A1 | 3/2013 | Maldonado et al. |
| 2013/0059009 A1 | 3/2013 | Kishimoto et al. |
| 2014/0030344 A1 | 1/2014 | Zepp et al. |
| 2014/0199340 A1 | 7/2014 | Maldonado |
| 2014/0212462 A1 | 7/2014 | Kang et al. |
| 2014/0242173 A1 | 8/2014 | Zepp et al. |
| 2014/0294982 A1 | 10/2014 | Freund et al. |
| 2014/0328854 A1 | 11/2014 | Maldonado et al. |
| 2014/0328921 A1 | 11/2014 | Maldonado |
| 2014/0328922 A1 | 11/2014 | Maldonado |
| 2014/0328923 A1 | 11/2014 | Maldonado et al. |
| 2014/0335186 A1 | 11/2014 | Kishimoto et al. |
| 2014/0356361 A1 | 12/2014 | Maldonado et al. |
| 2015/0024007 A1 | 1/2015 | Hessel et al. |
| 2015/0320728 A1* | 11/2015 | Fraser ................... A61K 39/00 424/185.1 |
| 2015/0320856 A1* | 11/2015 | Altreuter ................ A61K 39/00 424/501 |
| 2015/0320870 A1 | 11/2015 | Maldonado |
| 2015/0320884 A1* | 11/2015 | Fraser ................... A61K 39/00 424/193.1 |
| 2015/0328300 A1 | 11/2015 | Zepp et al. |
| 2015/0328309 A1 | 11/2015 | Ilyinskii et al. |
| 2015/0328333 A1* | 11/2015 | Fraser ................... A61K 39/00 424/193.1 |
| 2015/0335762 A1* | 11/2015 | Fraser ................... A61K 39/00 424/193.1 |

(56) References Cited

U.S. PATENT DOCUMENTS

| | | | |
|---|---|---|---|
| 2015/0359865 A1 | 12/2015 | Kishimoto | |
| 2015/0374815 A1 | 12/2015 | Kishimoto et al. | |
| 2016/0022650 A1* | 1/2016 | Fraser | A61K 39/00 424/185.1 |
| 2016/0030554 A1* | 2/2016 | Kishimoto | A61K 39/00 424/193.1 |
| 2016/0030555 A1* | 2/2016 | Kishimoto | A61K 39/00 424/185.1 |
| 2016/0067228 A1 | 3/2016 | Kishimoto et al. | |
| 2016/0074372 A1 | 3/2016 | Kishimoto | |
| 2016/0074427 A1 | 3/2016 | Kishimoto | |
| 2016/0074531 A1 | 3/2016 | Kishimoto | |
| 2016/0074532 A1 | 3/2016 | Kishimoto | |
| 2016/0128986 A1 | 5/2016 | O'Neil et al. | |
| 2016/0128987 A1 | 5/2016 | Griset et al. | |
| 2016/0220501 A1 | 8/2016 | Fraser et al. | |
| 2016/0243253 A1 | 8/2016 | Fraser et al. | |
| 2016/0256401 A1 | 9/2016 | Fraser et al. | |
| 2016/0279234 A1 | 9/2016 | Kishimoto et al. | |
| 2017/0258927 A1 | 9/2017 | Johnston | |
| 2017/0349433 A1 | 12/2017 | Lipford et al. | |
| 2018/0043023 A1 | 2/2018 | Ilyinski et al. | |
| 2018/0071394 A1 | 3/2018 | O'Neil et al. | |
| 2018/0085319 A1 | 3/2018 | Kishimoto | |
| 2018/0193482 A1 | 7/2018 | Ilyinski et al. | |
| 2018/0256709 A1 | 9/2018 | Zepp et al. | |
| 2018/0289776 A1 | 10/2018 | Johnston et al. | |

FOREIGN PATENT DOCUMENTS

| | | |
|---|---|---|
| CN | 101703781 A | 5/2010 |
| CN | 101861165 A | 10/2010 |
| CN | 102871966 B | 11/2013 |
| EP | 0759941 B1 | 9/2000 |
| EP | 1 932 538 A1 | 6/2008 |
| EP | 2073848 A2 | 7/2009 |
| EP | 2217269 B1 | 8/2010 |
| EP | 2345412 A1 | 7/2011 |
| EP | 2522338 A2 | 11/2012 |
| JP | H01-502909 A | 10/1999 |
| JP | 2005-516893 A | 6/2005 |
| JP | 2006-257095 | 9/2006 |
| JP | 2007-532517 A | 11/2007 |
| JP | 2008-515806 | 5/2008 |
| JP | 2008-532953 A | 8/2008 |
| JP | 2009-531068 | 9/2009 |
| JP | 2010-100578 A | 5/2010 |
| JP | 2010-514805 | 5/2010 |
| JP | 2010-533160 A | 10/2010 |
| KR | 10-2010-0099849 A | 9/2010 |
| WO | WO 88/06451 A1 | 9/1988 |
| WO | WO 95/11696 A1 | 5/1995 |
| WO | WO 96/012406 A1 | 2/1996 |
| WO | WO 96/20698 A2 | 7/1996 |
| WO | WO 98/010056 A1 | 12/1998 |
| WO | WO 99/22762 A1 | 5/1999 |
| WO | WO 99/34826 A1 | 7/1999 |
| WO | WO 02/09770 A1 | 2/2002 |
| WO | WO 02/32404 A2 | 4/2002 |
| WO | WO 02/088304 A2 | 11/2002 |
| WO | WO 2003/033526 A2 | 4/2003 |
| WO | WO 03/094840 A2 | 11/2003 |
| WO | WO 2005/097116 A1 | 10/2005 |
| WO | WO 2006/041890 A2 | 4/2006 |
| WO | WO 2006/094507 A1 | 9/2006 |
| WO | WO 2007/067683 A2 | 6/2007 |
| WO | WO 2007/087341 A2 | 8/2007 |
| WO | WO 2007/098254 A2 | 8/2007 |
| WO | WO 2007/133835 A2 | 11/2007 |
| WO | WO 2008/036374 A2 | 3/2008 |
| WO | WO 2008/043157 A1 | 4/2008 |
| WO | WO 2008/083331 A2 | 7/2008 |
| WO | WO 2008/109163 A1 | 9/2008 |
| WO | WO 2008/150868 A1 | 12/2008 |
| WO | WO 2009/007750 A1 | 1/2009 |
| WO | WO 2009/022154 A2 | 2/2009 |
| WO | WO 2009/039502 A1 | 3/2009 |
| WO | WO 2009/051837 A2 | 4/2009 |
| WO | WO 2009/106999 A2 | 9/2009 |
| WO | WO 2009/131712 A2 | 10/2009 |
| WO | WO 2009/145238 A1 | 12/2009 |
| WO | WO 2010/018384 A1 | 2/2010 |
| WO | WO 2010/027471 A2 | 3/2010 |
| WO | WO 2010/037402 A1 | 4/2010 |
| WO | WO 2010/042863 A1 | 4/2010 |
| WO | WO 2010/042866 | 4/2010 |
| WO | WO 2010/042870 A1 | 4/2010 |
| WO | WO 2010/042876 | 4/2010 |
| WO | WO 2010/047839 A1 | 4/2010 |
| WO | WO 2010/075072 A2 | 7/2010 |
| WO | WO 2010/116141 A2 | 10/2010 |
| WO | WO 2010/123569 A2 | 10/2010 |
| WO | WO 2010/125565 A2 | 11/2010 |
| WO | WO 2010/138192 A2 | 12/2010 |
| WO | WO 2010/138193 A2 | 12/2010 |
| WO | WO 2010/138194 | 12/2010 |
| WO | WO 2011/033090 A1 | 3/2011 |
| WO | WO 2011/109833 A2 | 9/2011 |
| WO | WO 2011/150240 A1 | 12/2011 |
| WO | WO 2011/156119 A1 | 12/2011 |
| WO | WO 2012/019041 A2 | 2/2012 |
| WO | WO 2012/021512 A2 | 2/2012 |
| WO | WO 2012/054920 A2 | 4/2012 |
| WO | WO 2012/149247 A2 | 11/2012 |
| WO | WO 2012/149252 A2 | 11/2012 |
| WO | WO 2012/149255 A2 | 11/2012 |
| WO | WO 2012/149259 A1 | 11/2012 |
| WO | WO 2012/149265 A2 | 11/2012 |
| WO | WO 2012/149268 A1 | 11/2012 |
| WO | WO 2012/149393 A2 | 11/2012 |
| WO | WO 2012/149405 A2 | 11/2012 |
| WO | WO 2012/149411 A1 | 11/2012 |
| WO | WO 2012/158362 A1 | 11/2012 |
| WO | WO 2013/058812 A1 | 4/2013 |
| WO | WO 2014/179771 A1 | 11/2014 |
| WO | WO 2015/162594 A2 | 10/2015 |

OTHER PUBLICATIONS

International Search Report and Written Opinion dated Sep. 22, 2014 in connection with PCT/US2014/036697.

International Preliminary Report on Patentability dated Nov. 12, 2015 in connection with PCT/US2014/036697.

Extended European Search Report dated Oct. 13, 2016 in connection with EP 14791119.2.

"Pluronic." Oxford Dictionary entry accessed via www.oxforddictionary.com on May 6, 2016. 8 pages.

Aalbers et al., Preclinical Potency and Biodistribution Studies of an AAV 5 Vector Expressing Human Interferon-β (ART-I02) for Local Treatment of Patients with Rheumatoid Arthritis. PLoS One. Jun. 24, 2015;10(6):e0130612. doi:10.1371/journal.pone.0130612. 17 pages.

Adorini et al., Tolerogenic dendritic cells induced by vitamin D receptor ligands enhance regulatory T cells inhibiting allograft rejection and autoimmune diseases. J Cell Biochem. Feb. 1, 2003;88(2):227-33.

Anguela et al., Robust ZFN-mediated genome editing in adult hemophilic mice. Blood. Nov. 7, 2013;122(19):3283-7. doi: 10.1182/blood-2013-04-497354. Epub Oct. 1, 2013.

Arruda et al., Strategies to modulate immune responses: a new frontier for gene therapy. Mol Ther. Sep. 2009; 17(9):1492-503. doi: 10.1038/mt.2009.150. Epub Jul. 7, 2009. Review.

Ashe et al., Inhibition of glycogen biosynthesis via mTORC1 suppression as an adjunct therapy for Pompe disease. Mol Genet Metab. Aug. 2010;100(4):309-15. doi: 10.1016/j.ymgme.2010.05. 001. Epub May 5, 2010.

Bae et al., Vinyl sulfone-terminated PEG-PLLA diblock copolymer for thiol-reactive polymeric micelle. Apr. 9, 2009;42(10):3437-42.

(56) References Cited

OTHER PUBLICATIONS

Barzel et al., Promoterless gene targeting without nucleases ameliorates haemophilia B in mice. Nature. Jan. 15, 2015;517(7534):360-4. doi: 10.1038/nature13864. Epub Jul. 15, 2015 21 pages.

Bawarski et al., Emerging nanopharmaceuticals. Nanomed: Nanotechnol Biol Med. 2008;4:273-82.

Binder et al., Tumor necrosis factor-inhibiting therapy preferentially targets bone destruction but not synovial inflammation in a tumor necrosis factor-driven model of rheumatoid arthritis. Arthritis Rheum. Mar. 2013;65(3):608-17. doi: 10.1002/art.37797.

Bisset et al., Therapeutic impact of systemic AAV-mediated RNA interference in a mouse model of myotonic dystrophy. Hum Mol Genet. Sep. 1, 2015;24(17):4971-83. doi: 10.1093/hmg/ddv219. Epub Jun. 16, 2015.

Boden et al., Regulatory T cells in inflammatory bowel disease. Curr Opin Gastroenterol. Nov. 2008;24(6):733-41.

Bouaziz et al., Regulatory B cells as inhibitors of immune responses and inflammation Immunol Rev. Aug. 2008;224:201-14. doi: 10.1111/j.1600-065X.2008.00661.x. Review.

Brown et al., Endogenous microRNA regulation suppresses transgene expression in hematopoietic lineages and enables stable gene transfer. Nat Med. May 2006;12(5):585-91. Epub Apr. 23, 2006.

Bryant et al., Nanoparticle delivery of donor antigens for transplant tolerance in allogeneic islet transplantation. Biomaterials. Oct. 2014;35(31):8887-94. doi: 10.1016/j.biomaterials.2014.06.044.

Caccamo et al., Rapamycin rescues TDP-43 mislocalization and the associated low molecular mass neurofilament instability. J Biol Chem. Oct. 2, 2009;284(40):27416-24. doi: 10.1074/jbc.M109.031278. Epub Aug. 3,2009.

Cappellano et al., Subcutaneous inverse vaccination with PLGA particles loaded with a MOG peptide and IL-10 decreases the severity of experimental autoimmune encephalomyelitis. Vaccine. Aug. 20, 2014 pii: S0264-410X(14)01129-3. doi: 10.1016/j.vaccine.2014.08.016. 9 pages.

Carpentier et al., Effect of alipogene tiparvovec (AAV1-LPL(S447X)) on postprandial chylomicron metabolism in lipoprotein lipase-deficient patients. J Clin Endocrinol Metab. May 2012;97(5):1635-44. doi: 10.1210/jc.2011-3002. Epub Mar. 21, 2012.

Chen et al., Targeting transgene to the heart and liver with AAV9 by different promoters. Clin Exp Pharmacol Physiol. Oct. 2015;42(10):1108-17. doi: 10.1111/1440-1681.12453. Original Article. 24 pages.

Cheng et al., Efficient gene editing in adult mouse livers via adenoviral delivery of CRISPR/Cas9. FEBS Lett. Nov. 3, 2014;588(21):3954-8. doi: 10.1016/j.febslet.2014.09.008. Epub Sep. 19, 2014.

Colman et al., Effects of amino acid sequence changes on antibody-antigen interactions. Res Immunol. Jan. 1994;145(1):33-6.

Coombes et al., A functionally specialized population of mucosal CD103+ DCs induces Foxp3+ regulatory T cells via a TGF-beta and retinoic acid-dependent mechanism. J Exp Med. Aug. 6, 2007;204(8):1757-64. Epub Jul. 9, 2007.

Corti et al., B-Cell Depletion is Protective Against Anti-AAV Capsid Immune Response: A Human Subject Case Study. Mol Ther Methods Clin Dev. 2014;1. pii: 14033. 7 pages.

Cvetanovich et al., Human regulatory T cells in autoimmune diseases. Curr Opin Immunol. Dec. 2010;22(6):753-60. Epub Sep. 24, 2010.

Das et al., Delivery of rapamycin-loaded nanoparticle down regulates ICAM-1 expression and maintains an immunosuppressive profile in human CD34+ progenitor-derived dendritic cells. J Biomed Mater Res A. Jun. 15, 2008 ;85(4):983-92.

Davila et al., Cell-based immunotherapy with suppressor CD8+ T cells in rheumatoid arthritis. J Immunol. Jun. 1, 2005;174(11):7292-301.

Denti et al., Body-wide gene therapy of Duchenne muscular dystrophy in the mdx mouse model. Proc Natl Acad Sci U S A. Mar. 7, 2006;103(10):3758-63. Epub Feb. 24, 2006.

Dinarvand et al., Polylactide-co-glycolide nanoparticles for controlled delivery of anticancer agents. Int J Nanomedicine. 2011;6:877-95. doi: 10.2147/IJN.S18905. Epub May 27, 2011.

Dinesh et al., CD8+ Tregs in lupus, autoimmunity, and beyond. Autoimmun Rev. Jun. 2010;9(8):560-8. doi: 10.1016/j.autrev.2010.03.006. Epub Jun. 1, 2011. 21 pages.

Dobrolovskaja et al., Immunological properties of engineered nonomaterials. Nat Nanotechnol. Aug. 2007;2(8):469-78. Review.

Düchs, Dissertation entitled: Effects of Toll-like receptor agonists on the pathogenesis of atopic asthma in mice, University of Würzburg, Sep. 2011. 147 pages.

Eghtesad et al., Effect of rapamycin on immunity induced by vector-mediated dystrophin expression in mdx skeletal muscle. Sci Rep. 2012;2:399. doi: 10.1038/srep00399. Epub May 8, 2012. 6 pages.

Endharti et al., Cutting edge: CD8+CD122+ regulatory T cells produce IL-10 to suppress IFN-gamma production and proliferation of CD8+ T cells. J Immunol. Dec. 1, 2005;175(11):7093-7.

Falk et al., Induction and suppression of an autoimmune disease by oligomerized T cell epitopes: enhanced in vivo potency of encephalitogenic peptides. J Exp Med. Feb. 21, 2000;191(4):717-30.

Fasier et al., Antagonistic peptides specifically inhibit proliferation, cytokine production, CD40L expression, and help for IgE synthesis by Der p 1-specific human T-cell clones. J Allergy Clin Immunol. Apr. 1998;101(4 Pt 1):521-30.

Faunce et al., Cutting edge: in vitro-generated tolerogenic APC induce CD8+ T regulatory cells that can suppress ongoing experimental autoimmune encephalomyelitis. J Immunol. Feb. 15, 2004;172(4):1991-5.

Fifis et al., Size-dependent immunogenicity: therapeutic and protective properties of nano-vaccines against tumors. J Immunol. Sep. 1, 2004;173(5):3148-54.

Fiorino et al., A single cohort, dose escalation phase 1 study of intravenous infusion of pegsiticase (formerly Uricase-PEG 20), a drug for managing hyperuricemia in refractory gout [Abstract]. Abstracts of the American College of Rheumatology/Association of Rheumatology Health Professionals Annual Scientific Meeting. Atlanta, Georgia. Nov. 6-11, 2010. Arthritis Rheum. Nov. 2010;62 Suppl 10: 144. Doi: 10.1002/art.27913. 2 pages.

Fischer et al., Rapamycin-conditioned, alloantigen-pulsed myeloid dendritic cells present donor MHC class I/peptide via the semi-direct pathway and inhibit survival of antigen-specific CD8(+) T cells in vitro and in vivo. Transpl Immunol. Jul. 2011;25(1):20-6. Epub May 10, 2011.

Fraser et al., Nanoparticle therapy for allergic and inflammatory disease. Anti-Inflammatory & Anti-Allergy Agents Med Chem. Mar. 2010;9(1):54-70.

Gajofatto et al., Treatment strategies for multiple sclerosis: When to start, when to change, when to stop? World J Clin Cases. Jul. 16, 2015;3(7):545-55. doi: 10.12998/wjcc.v3.i7.545.

Gao et al., Contrasting effects of cyclosporine and rapamycin in de novo generation of alloantigen-specific regulatory T cells. Am J Transplant Jul. 2007;7(7):1722-32. Epub May 19, 2007.

Garcia et al., CCR9+ and CD103+ tolerogenic dendritic cell populations in food allergy patients undergoing oral immunotherapy. Clin Transl Allergy. 2011; 1(Suppl 1): O51.

Getts et al., Harnessing nanoparticles for immune modulation. Trends Immunol. Jul. 2015;36(7):419-427.

Goyenvalle et al., Engineering multiple U7snRNA constructs to induce single and multiexon-skipping for Duchenne muscular dystrophy. Mol Ther. Jun. 2012;20(6):1212-21. doi: 10.1038/mt.2012.26. Epub Feb. 21, 2012.

Gray et al., Apoptotic cells protect mice from autoimmune inflammation by the induction of regulatory B cells. Proc Natl Acad Sci U S A. Aug. 28, 2007;104(35):14080-5. Epub Aug. 21, 2007.

Gray et al., What are regulatory B cells? Eur J Immunol. Oct. 2010;40(10):2677-9.

Haddadi et al., Delivery of rapamycin by PLGA nanoparticles enhances its suppressive activity on dendritic cells. J Biomed Mater Res A. Mar. 15, 2008;84(4):885-98.

(56) References Cited

OTHER PUBLICATIONS

Hahn et al., Cellular and molecular mechanisms of regulation of autoantibody production in lupus. Ann N Y Acad Sci. Jun. 2005;1051:433-41. Review. Epub Apr. 10, 2008. 9 pages.

Hahn et al., Tolerogenic treatment of lupus mice with consensus peptide induces Foxp3-expressing, apoptosis-resistant, TGFbeta-secreting CD8+ T cell suppressors. J Immunol. Dec. 1, 2005;175(11):7728-37.

Hamdy et al., Co-delivery of cancer-associated antigen and Toll-like receptor 4 ligand in PLGA nanoparticles induces potent CD8+ T cell-mediated anti-tumor immunity. Vaccine. Sep. 15, 2008;26(39):5046-57. doi: 10.1016/j.vaccine.2008.07.035. Epub Aug. 3, 2008.

Hamdy et al., Part I: targeted particles for cancer immunotherapy. Curr Drug Deliv. May 2011;8(3):261-73.

Hamdy et al., Targeting dendritic cells with nano-particulate PLGA cancer vaccine formulations. Adv Drug Deliv Rev. Sep. 10, 2011;63(10-11):943-55. doi: 10.1016/j.addr.2011.05.021. Epub Jun. 6, 2011. Review.

Hamdy et al., The immunosuppressive activity of polymeric micellar formulation of cyclosporine A: in vitro and in vivo studies. AAPS J. Jun. 2011;13(2):159-68. doi: 10.1208/s12248-011-9259-8. Epub Feb. 19, 2011.

Händel et al., Versatile and efficient genome editing in human cells by combining zinc-finger nucleases with adeno-associated viral vectors. HumGene Ther. Mar. 2012;23(3):321-9. doi: 10.1089/hum.2011.140. Epub Dec. 14, 2011.

Hashimoto et al., Stimulation of host NKT cells by synthetic glycolipid regulates acute graft-versus-host disease by inducing Th2 polarization of donor T cells. J Immunol. Jan. 1, 2005;174(1):551-6.

Hui et al., Modulation of CD8+ T cell responses to AAV vectors with IgG-derived MHC class II epitopes. Mol Ther. Sep. 2013;21(9):1727-37. doi: 10.1038/mt.2013.166. Epub Jul. 16, 2013.

Imamura et al., Pravastatin attenuates allergic airway inflammation by suppressing antigen sensitisation, interleukin 17 production and antigen presentation in the lung. Thorax. Jan. 2009;64(1):44-9. doi: 10.1136/thx.2007.094540. Epub Oct. 3, 2008.

Ito et al., A convenient enzyme-linked immunosorbent assay for rapid screening of anti-adeno-associated virus neutralizing antibodies. Ann Clin Biochem. Nov. 2009;46(Pt 6):508-10. doi: 10.1258/acb.2009.009077. Epub Sep. 3, 2009.

Jhunjhunwala et al., Delivery of rapamycin to dendritic cells using degradable microparticles. J Control Release. Feb. 10, 2009;133(3):191-7. doi: 10.1016/j.jconrel.2008.10.011. Epub Oct. 26, 2008.

Jiang et al., Effects of transient immunosuppression on adenoassociated, virus-mediated, liver-directed gene transfer in rhesus macaques and implications for human gene therapy. Blood. Nov. 15, 2006;108(10):3321-8. Epub Jul. 25, 2006.

Jones, Critically assessing the state-of-the-art in protein structure prediction. Pharmacogenomics J. 2001;1(2):126-34. Review.

Kang et al., Very low-dose tolerance with nucleosomal peptides controls lupus and induces potent regulatory T cell subsets. J Immunol. Mar. 15, 2005;174(6):3247-55.

Karamloo et al., Prevention of allergy by a recombinant multi-allergen vaccine with reduced IgE binding and preserved T cell epitopes. Eur J Immunol. Nov. 2005;35(11):3268-76.

Keselowsky et al., Multifunctional dendritic cell-targeting polymeric microparticles: engineering new vaccines for type 1 diabetes. Hum Vaccin. Jan. 1, 2011;7(1):37-44. Epub Jan. 1, 2011. Review.

Kim et al., Inhibition of follicular T-helper cells by CD8(+) regulatory T cells is essential for self. Nature. Sep. 16, 2010;467(7313):328-32.

Kim et al., Simvastatin induces Foxp3+ T regulatory cells by modulation of transforming growth factor-beta signal transduction. Immunology. Aug. 2010;130(4):484-93. doi: 10.1111/j.1365-2567.2010.03269.x. Epub Apr. 12, 2010.

Kingsley et al., Transplantation tolerance: lessons from experimental rodent models. Transpl Int. Oct. 2007;20(10):828-41. Epub Aug. 17, 2007.

Konya et al., Treating autoimmune disease by targeting CD8(+) T suppressor cells. Expert Opin Biol Ther. Aug. 2009;9(8):951-65. doi: 10.1517/14712590903020759. Review. Epub Aug. 1, 2010. 22 pages.

Lassmann et al., The molecular basis of neurodegeneration in multiple sclerosis. FEBS Lett. Dec. 1, 2011;585(23):3715-23. doi: 10.1016/j.febslet.2011.08.004. Epub Aug. 16, 2011.

Le Hir et al., AAV genome loss from dystrophic mouse muscles during AAV-U7 snRNA-mediated exon-skipping therapy. Mol Ther. Aug. 2013;21(8):1551-8. doi: 10.1038/mt.2013.121. Epub Jun. 11, 2013

Louis Jeune et al., Pre-existing anti-adeno-associated virus antibodies as a challenge in AAV gene therapy. Hum Gene Ther Methods. Apr. 2013;24(2):59-67. doi: 10.1089/hgtb.2012.243. Epub Apr. 3, 2013. Review.

Lutsiak et al., Analysis of poly(D,L-lactic-co-glycolic acid) nanosphere uptake by human dendritic cells and macrophages in vitro. Pharm Res. Oct. 2002;19(10):1480-7.

Manno et al., Successful transduction of liver in hemophilia by AAV-Factor IX and limitations imposed by the host immune response. Nat Med. Mar. 2006;12(3):342-7. Epub Feb. 12, 2006 Erratum in: Nat Med. May 2006;12(5):592.

Martino et al., Engineered AAV vector minimizes in vivo targeting of transduced hepatocytes by capsid-specific CD8+ T cells. Blood. Mar. 21, 2013;121(12):2224-33. doi: 10.1182/blood-2012-10-460733. Epub Jan. 16, 2013.

Mason, Functional Analysis of the Cysteine Residues of Activin A. Mol Endocrinol. 1994;8(3):325-32.

McMahon et al., Epitope spreading initiates in the CNS in two mouse models of multiple sclerosis. Nat Med. Mar. 2005;11(3):335-9. Epub Feb. 27, 2005.

Meliani et al., Determination of anti-adeno-associated virus vector neutralizing antibody titer with an in vitro reporter system. Hum Gene Ther Methods. Apr. 2015;26(2):45-53. doi: 10.1089/hgtb.2015.037.

Menzies et al., Simvastatin does not exhibit therapeutic anti-inflammatory effects in asthma. J Allergy Clin Immunol. Feb. 2007;119(2):328-35. Epub Dec. 4, 2006.

Mingozzi et al., Modulation of tolerance to the transgene product in a nonhuman primate model of AAV-mediated gene transfer to liver. Blood. Oct. 1, 2007;110(7):2334-41. Epub Jul. 3, 2007.

Miyara et al., Therapeutic approaches to allergy and autoimmunity based on FoxP3+ regulatory T-cell activation and expansion. J Allergy Clin Immunol. Apr. 2009;123(4):749-55.

Moghimi et al., Induction of tolerance to factor VIII by transient co-administration with rapamycin. J Thromb Haemost. Aug. 2011;9(8):1524-33. doi: 10.1111/j.1538-7836.2011.04351.x.

Mottram et al., Type 1 and 2 immunity following vaccination is influenced by nanoparticle size: formulation of a model vaccine for respiratory syncytial virus. Mol Pharm. Jan.-Feb. 2007;4(1):73-84.

Nathwani et al., Adenovirus-associated virus vector-mediated gene transfer in hemophilia B. N Engl J Med. Dec. 22, 2011;365(25):2357-65. doi: 10.1056/NEJMoa1108046. Epub Dec. 10, 2011.

Nathwani et al., Long-term safety and efficacy of factor IX gene therapy in hemophilia B. N Engl J Med. Nov. 20, 2014;371(21):1994-2004. doi: 10.1056/NEJMoa1407309. Epub May 20, 2015. 17 pages Nathwani et al., Self-complementary adeno-associated virus vectors containing a novel liverspecific human factor IX expression cassette enable highly efficient transduction of murine and nonhuman primate liver. Blood. Apr. 1, 2006;107(7):2653-61. doi: 10.1182/blood2005104035. Epub Dec. 1, 2005.

Nayak et al., Prevention and Reversal of Antibody Responses Against Factor IX in Gene Therapy for Hemophilia B. Front Microbiol. Dec. 7, 2011;2:244. doi: 10.3389/fmicb.2011.00244. eCollection 2011.

Neuhaus et al., mTOR inhibitors: an overview. Liver Transpl. Jun. 2001;7(6):473-84.

Ngo et al., In The Protein Folding Problem and Tertiary Structure Prediction, 1994. Eds Mertz et al. Birkhauser. Boston, MA. 1994:433,491-5.

Nixon et al., Synthetic peptides entrapped in microparticles can elicit cytotoxic T cell activity. Vaccine. Nov. 1996;14(16):1523-30.

(56) References Cited

OTHER PUBLICATIONS

Oh et al., CD4+CD25+ regulatory T cells in autoimmune arthritis. Immunol Rev. Jan. 2010;233(1):97-111.

Omata et al., Ovalbumin-specific IgE modulates ovalbumin-specific T-cell response after repetitive oral antigen administration. J Allergy Clin Immunol. Apr. 2005;115(4):822-7.

Paolicelli et al., Surface-modified PLGA-based nanoparticles that can efficiently associate and deliver virus-like particles. Nanomedicine (Lond). Aug. 2010;5(6):843-53.

Platt et al., CRISPR-Cas9 knockin mice for genome editing and cancer modeling. Cell. Oct. 9, 2014;159(2):440-55. doi: 10.1016/j.cell.2014.09.014. Epub Sep. 25, 2014.

Post et al., Adenoviral PR39 improves blood flow and myocardial function in a pig model of chronic myocardial ischemia by enhancing collateral formation. Am J Physiol Regul Integr Comp Physiol. Mar. 2006;290(3):R494-500. Epub Oct. 27, 2005.

Ran et al., In vivo genome editing using *Staphylococcus aureus* Cas9. Nature. Apr. 9, 2015;520(7546):186-91. doi: 10.1038/nature14299. Epub Apr. 1, 2015.

Reichardt et al., Impact of Mammalian Target of Rapamycin Inhibition on Lymphoid Homing and Tolerogenic Function of Nanoparticle-Labeled Dendritic Cells following Allogeneic Hematopoietic Cell Transplantation. J Immunol. 2008;181:4770-9.

Samuel et al., Nanoparticle delivery systems for control of immunity. Proceedings of the 2004 Intl. Conference on MEMS, NANO and Smart Systems (ICMENS '04). IEEE 2004. 3 pages.

Samuel et al., Polymeric nanoparticles for targeted delivery of Therapeutic Vaccines to dendritic cells. Proceedings of the International Conference on MEMS, NANO and Smart Systems. (ICMENS '03). IEEE 2003. 5 pages.

Schmidt et al., CRISPR genome engineering and viral gene delivery: a case of mutual attraction. Biotechnol J. Feb. 2015;10(2):258-72. doi: 10.1002/biot.201400529. Epub Feb. 6, 2015.

Seffernick et al., Melamine deaminase and atrazine chlorohydrolase: 98 percent identical but functionally different. J Bacteriol. Apr. 2001;183(8):2405-10.

Senis et al., CRISPR/Cas9-mediated genome engineering: an adeno-associated viral (AAV) vector toolbox. Biotechnol J. Nov. 2014;9(11):1402-12. doi: 10.1002/biot.201400046. Epub Oct. 6, 2014 Supporting Information. 26 pages.

Sharabi et al., The suppression of murine lupus by a tolerogenic peptide involves foxp3-expressing CD8 cells that are required for the optimal induction and function of foxp3-expressing CD4 cells. J Immunol. Sep. 1, 2008;181(5):3243-51.

Shen et al., Combined effect of cyclosporine and sirolimus on improving the longevity of recombinant adenovirus-mediated transgene expression in the retina. Arch Ophthalmol. Jul. 2001;119(7):1033-43.

Shimizu et al., Direct anti-inflammatory mechanisms contribute to attenuation of experimental allograft arteriosclerosis by statins. Circulation. Oct. 28, 2003;108(17):2113-20. Epub Sep. 29, 2003.

Skolnick et al., From genes to protein structure and function: novel applications of computational approaches in the genomic era. Trends Biotechnol. Jan. 2000;18(1):34-9. Review.

Soroosh et al., Th9 and allergic. disease. Immunology. Aug. 2009;127(4):450-8. doi: 10.1111/j.1365-2567.2009.03114.x.

Stanek et al., Silencing mutant huntingtin by adeno-associated virus-mediated RNA interference ameliorates disease manifestations in the YAC128 mouse model of Huntington's disease. Hum Gene Ther. May 2014;25(5):461-74. doi: 10.1089/hum.2013.200. Epub Mar. 21, 2014.

Stepkowski et al., Inhibition of host-versus-graft and graft-versus-host responses after small bowel transplantation in rats by rapamycin. Transplantation. Feb. 1992;53(2):258-64.

Suzuki et al., Inhibitory CD8+ T cells in Autoimmune Disease. Hum Immunol. Nov. 2008;69(11):781-9. doi:10.1016/j.humimm.2008.08.283. Epub Nov. 1, 2009.

Tai et al., A novel rapamycin-polymer conjugate based on a new poly(ethylene glycol) multiblock copolymer. Pharm Res. Mar. 2014;31(3):706-19. doi: 10.1007/s11095-013-1192-3. Epub Sep. 26, 2013.

Tarzi et al., Peptide immunotherapy for allergic disease. Expert Opin Biol Ther. Jul. 2003;3(4):617-26. Review.

Thomson et al., Immunoregulatory functions of mTOR inhibition. Nat Rev Immunol. May 2009;9(5):324-37. doi: 10.1038/nri2546.

Tosatto et al., Large-scale prediction of protein structure and function from sequence. Curr Pharm Des. 2006;12(17):2067-86. Review.

Tuohy, Peptide determinants of myelin proteolipid protein (PLP) in autoimmune demyelinating disease: a review. Neurochem Res. Aug. 1994;19(8):935-44.

Turnquist et al., Rapamycin-conditioned dendritic cells are poor stimulators of allogeneic CD4+ T cells, but enrich for antigen-specific Foxp3+ T regulatory cells and promote organ transplant tolerance. J Immunol. Jun. 1, 2007;178(11):7018-31.

Vila et al., Regulatory T cells and autoimmunity. Curr Opin Hematol. Jul. 2009;16(4):274-9.

Wang et al., A systematic assessment of MHC class II peptide binding predictions and evaluation of a consensus approach. PLoS Comput Biol. Apr. 4, 2008;4(4):e1000048. doi: 10.1371/journal.pcbi.1000048.

Weber et al., AAV-mediated delivery of zinc finger nucleases targeting hepatitis B virus inhibits active replication. PLoS One. May 14, 2014;9(5):e97579. doi: 10.1371/journal.pone.0097579. eCollection 2014. 14 pages.

Witkowski et al., Conversion of a beta-ketoacyl synthase to a malonyl decarboxylase by replacement of the active-site cysteine with glutamine. Biochemistry. Sep. 7, 1999;38(36):11643-50.

Wu et al., Humanization of a murine monoclonal antibody by simultaneous optimization of framework and CDR residues. J Mol Biol. Nov. 19, 1999;294(1):151-62.

Yamaguchi et al., Around hematological malignancies. Trends in Hematological Malignancies. 2010;2(2):96-98.

Yamaki et al., Preventive and therapeutic effects of rapamycin, a mammalian target of rapamycin inhibitor, on food allergy in mice. Allergy. Oct. 2012;67(10):1259-70. doi: 10.1111/a11.12000. Epub Aug. 23, 2012.

Yeste et al., Nanoparticle-mediated codelivery of myelin antigen and a tolerogenic small molecule suppresses experimental autoimmune encephalomyelitis. Proc Natl Acad Sci U S A. Jul. 10, 2012;109(28):11270-5. doi: 10.1073/pnas.1120611109. Epub Jun. 27, 2012.

Yuan et al., Preparation of rapamycin-loaded chitosan/PLA nanoparticles for immunosuppression in corneal transplantation. Int J Pharm. Feb. 12, 2008;349(1-2):241-8. Epub Aug. 11, 2007.

Zhang et al., The mechanism of B lymphocytes in inducing immune tolerance. Immunol J. Jul. 2010;26(7):643-6.

Zhang-Hoover et al., Tolerogenic APC generate CD8+ T regulatory cells that modulate pulmonary interstitial fibrosis. J Immunol. Jan. 1, 2004;172(1):178-85.

Zhou et al., Updates of mTOR inhibitors. Anticancer Agents Med Chem. Sep. 2010;10(7):571-81.

Zweers, Biodegradable nanoparticles of intravascular drug delivery. Unversiteit Twente, 2003.

Amu et al., Regulatory B cells prevent and reverse allergic airway inflammation via FoxP3-positive T regulatory cells in a murine model. J Allergy Clin Immunol. 2010;125:1114-24.

Battaglia et al., Rapamycin promotes expansion of functional CD4+CD25+FOXP3+ regulatory T cells of both healthy subjects and type 1 diabetic patients. J Immunol. Dec. 15, 2006;177(12):8338-47.

Beevers et al., Curcumin inhibits the mammalian target of rapamycin-mediated signaling pathways in cancer cells. Int J Cancer. Aug. 15, 2006;119(4):757-64.

Bocian et al., Rapamycin, unlike cyclosporine A, enhances suppressive functions of in vitro-induced CD4+CD25+ Tregs. Nephrol Dial Transplant. Mar. 2010 ;25(3):710-7. doi: 10.1093/ndt/gfp586. Epub Nov. 9, 2009.

Dao et al., Pharmacokinetics and pharmacodynamics evaluation of therapeutic protein drugs. China Pharm. Dec. 31, 2007;18(32):2546-7.

(56) References Cited

OTHER PUBLICATIONS

Delgoffe et al., The mTOR kinase differentially regulates effector and regulatory T cell lineage commitment. Immunity. Jun. 19, 2009;30(6):832-44. doi: 10.1016/j.immuni.2009.04.014.
Dilillo et al., B10 cells and regulatory B cells balance immune responses during inflammation, autoimmunity, and cancer. Ann N Y Acad Sci. Jan. 2010;1183:38-57. doi: 10.1111/j.1749-6632.2009. 05137.x. Review.
Fourtounas et al., Different immunosuppressive combinations on T-cell regulation in renal transplant recipients. Am J Nephrol. 2010;32(1):1-9. doi: 10.1159/000313940. Epub May 20, 2010.
Kim et al., Effects of cyclosporine and rapamycin on immunoglobulin production by preactivated human B cells. Clin Exp Immunol. Jun. 1994;96(3):508-12.
Lu et al., Rapamycin promotes the expansion of CD4(+) Foxp3(+) regulatory T cells after liver transplantation. Transplant Proc. Jun. 2010;42(5):1755-7. doi: 10.1016/j.transproceed.2009.10.008.
Maldonado et al., Polymeric synthetic nanoparticles for the induction of antigen-specific immunological tolerance. Proc Natl Acad Sci U S A. Jan. 13, 2015;112(2):E156-65. doi: 10.1073/pnas. 1408686111. Epub Dec. 29, 2014.
Moraes-Fontes et al., Steroid treatments in mice do not alter the number and function of regulatory T cells, but amplify cyclophosphamide-induced autoimmune disease. J Autoimmun. Sep. 2009;33(2):109-20. doi: 10.1016/j.jaut.2009.03.008. Epub Apr. 11, 2009.
Papisov, Acyclic polyacetals from polysaccharides: biomimetic biomedical "stealth" polymers. Chapter 19. ACS Symposium Series. Feb. 15, 2001:786:301-14.
Sbiera et al., Influence of short-term glucocorticoid therapy on regulatory T cells in vivo. PLoS One. 2011;6(9):e24345. doi: 10.1371/journal.pone.0024345. Epub Sep. 2, 2011.
[No Author Listed] Selecta Biosciences Announces Dosing of First Patent in Phase 1b Clinical Trial of SEL-212, Designed to be the First Non-Immunogenic Biologic Treatment for Gout. Press Release. Dec. 23, 2015. Retrieved from the Internet via http://selectabio. com/2015/12/23/selecta-biosciences-announces-dosing-of-first-patient-in-phase-1b-clinical-trial-of-se1-212-designed-to-be-the-first-non-immunogenic-biologic-treatment-for-gout. Last access on May 10, 2017.
Berhanu et al., Pegloticase failure and a possible solution: Immunosuppression to prevent intolerance and inefficacy in patients with gout. Semin Arthritis Rheum. Jun. 2017;46(6):754-758. doi: 10.1016/j.semarthrit.2016.09.007. Epub Sep. 20, 2016.
Hershfield et al., Induced and pre-existing anti-polyethylene glycol antibody in a trial of every 3-week dosing of pegloticase for refractory gout, including in organ transplant recipients. Arthritis Res Ther. Mar. 7, 2014;16(2):R63. doi: 10.1186/ar4500.
Ishii, [Allergen-specific immunotherapy utilizing mechanisms for immune regulation]. Nihon Rinsho Meneki Gakkai Kaishi. Oct. 2008;31(5):392-8. Review.
Kishimoto et al., Improving the efficacy and safety of biologic drugs with tolerogenic nanoparticles. Nat Nanotechnol. Oct. 2016;11(10):890-899. doi: 10.1038/nnano.2016.135. Epub Aug. 1, 2016.
Kunisawa et al., Fusogenic liposome functions as an efficient immunoadjuvant in inducing humoral immune-response to soluble antigen. Drug Delivery System. Jan. 1998;13(1):21-26.
Lipsky et al., Pegloticase immunogenicity: the relationship between efficacy and antibody development in patients treated for refractory chronic gout. Arthritis Res Ther. Mar. 4, 2014;16(2):R60. doi: 10.1186/ar4497.
Macary et al., Ovalbumin-specific, MHC class I-restricted, alpha beta-positive, Tc1 and Tc0 CD8+ T cell clones mediate the in vivo inhibition of rat IgE. J Immunol. Jan. 15, 1998;160(2):580-7.
McKay et al., A novel anti-inflammatory role of simvastatin in a murine model of allergic asthma. J Immunol. Mar. 1, 2004;172(5):2903-8.
Renz et al., Comparison of the allergenicity of ovalbumin and ovalbumin peptide 323-339. Differential expansion of V beta-expressing T cell populations. J Immunol. Dec. 15, 1993;151(12):7206-13.
U.S. Appl. No. 14/273,099, filed May 8, 2014, Zepp et al.
U.S. Appl. No. 14/658,040, filed Mar. 13, 2015, Zepp et al.
U.S. Appl. No. 13/289,211, filed Nov. 4, 2011, Zepp et al.
U.S. Appl. No. 14/802,260, filed Jul. 17, 2015, Altreuter et al.
U.S. Appl. No. 13/457,936, filed Apr. 27, 2012, Kishimoto et al.
U.S. Appl. No. 13/458,220, filed Apr. 27, 2012, Fraser et al.
U.S. Appl. No. 14/161,660, filed Jan. 22, 2014, Maldonado.
U.S. Appl. No. 14/846,964, filed Sep. 7, 2015, Kishimoto.
U.S. Appl. No. 14/846,967, filed Sep. 7, 2015, Kishimoto.
[No Author Listed] Drug delivery system. Nankodo Co., Ltd. Apr. 15, 1986:70-1.
Alewine et al., Efficacy of RG7787, a next-generation mesothelin-targeted immunotoxin, against triple-negative breast and gastric cancers. Mol Cancer Ther. Nov. 2014;13(11):2653-61. doi: 10.1158/1535-7163.MCT-14-0132. Epub Sep. 19, 2014.
Baker et al., Immunogenicity of protein therapeutics: The key causes, consequences and challenges. Self Nonself—Immune Recognition and Signaling. Dec. 1, 2010;1(4):314-22.
Bayle et al., Rapamycin analogs with differential binding specificity permit orthogonal control of protein activity. Chem Biol. Jan. 2006;13(1):99-107.
Esposito et al., Rapamycin inhibits relapsing experimental autoimmune encephalomyelitis by both effector and regulatory T cells modulation. J Neuroimmunol. Mar. 30, 2010;220(1-2):52-63. doi: 10.1016/j.jneuroim.2010.01.001. Epub Feb. 11, 2010.
Hassan et al., Major cancer regressions in mesothelioma after treatment with an anti-mesothelin immunotoxin and immune suppression. Sci Transl Med. Oct. 23, 2013;5(208):208ra147. doi: 10.1126/scitranslmed.3006941.
Maher et al., Targeting cytotoxic T lymphocytes for cancer immunotherapy. Br J Cancer. Aug. 31, 2004;91(5):817-21. Review.
Maldonado et al., How tolerogenic dendritic cells induce regulatory T cells. Adv Immunol. 2010;108:111-65. doi: 10.1016/B978-0-12-380995-7.00004-5. Review.
Mazor et al., Immunogenicity of therapeutic recombinant immunotoxins. Immunol Rev. Mar. 2016;270(1):152-64. doi: 10.1111/imr.12390. Review.
McFarland et al., Ovalbumin(323-339) peptide binds to the major histocompatibility complex class II I-A(d) protein using two functionally distinct registers. Biochemistry. Dec. 14, 1999;38(50):16663-70.
Mine et al., Epitope characterization of ovalbumin in BALB/c mice using different entry routes. Biochim Biophys Acta. Feb. 2007;1774(2):200-12. Epub Dec. 19, 2006.
Onda et al., Tofacitinib suppresses antibody responses to protein therapeutics in murine hosts. J Immunol. Jul. 1, 2014;193(1):48-55. doi: 10.4049/jimmunol.1400063. Epub Jun. 2, 2014.
Pastan et al., Immunotoxin therapy of cancer. Nat Rev Cancer. Jul. 2006;6(7):559-65. Review.
Quarcoo et al., Resiquimod, a new immune response modifier from the family of imidazoquinolinamines, inhibits allergen-induced Th2 responses, airway inflammation and airway hyper-reactivity in mice. Clin Exp Allergy. Aug. 2004;34(8):1314-20.
Reddy et al., Detection of autoreactive myelin proteolipid protein 139-151-specific T cells by using MHC II (IAs) tetramers. J Immunol. Jan 15, 2003;170(2):870-7.
Rice-Ficht et al., Polymeric particles in vaccine delivery. Curr Opin Microbiol. Feb. 2010;13(1):106-12. doi: 10.1016/j.mib.2009.12. 001. Epub Jan. 14, 2010. Review.
Rizvi et al., Activity and safety of nivolumab, an anti-PD-1 immune checkpoint inhibitor, for patients with advanced, refractory squamous non-small-cell lung cancer (CheckMate 063): a phase 2, single-arm trial. Lancet Oncol. Mar. 2015;16(3):257-65. doi: 10.1016/S1470-2045(15)70054-9. Epub Feb. 20, 2015.
Zhang, Introduction to basic medicine. China University of Science and Technology Press. Aug. 31, 2012:423.
U.S. Appl. No. 13/948,129, filed Jul. 22, 2013, Zepp et al.
U.S. Appl. No. 12/788,261, filed May 26, 2010, Lipford et al.
U.S. Appl. No. 15/889,014, filed Feb. 5, 2018, Zepp et al.

(56) References Cited

OTHER PUBLICATIONS

U.S. Appl. No. 12/862,076, filed Aug. 24, 2010, Fraser et al.
U.S. Appl. No. 13/116,453, filed May 26, 2011, Bratzler et al.
U.S. Appl. No. 12/764,569, filed Apr. 21, 2010, Lipford et al.
U.S. Appl. No. 15/629,973, filed Jun. 22, 2017, Lipford et al.
U.S. Appl. No. 13/116,488, filed May 26, 2011, Bratzler et al.
U.S. Appl. No. 15/684,896, filed Aug. 23, 2017, Ilyinskii et al.
U.S. Appl. No. 13/116,556, filed May 26, 2011, Bratzler et al.
U.S. Appl. No. 13/428,340, filed Mar. 23, 2012, Altreuter et al.
U.S. Appl. No. 14/810,418, filed Jul. 27, 2015, Fraser et al.
U.S. Appl. No. 15/050,397, filed Feb. 22, 2016, Fraser et al.
U.S. Appl. No. 16/056,204, filed Aug. 6, 2018, Altreuter et al.
U.S. Appl. No. 13/560,955, filed Jul. 27, 2012, Altreuter et al.
U.S. Appl. No. 14/810,427, filed Jul. 27, 2015, Fraser et al.
U.S. Appl. No. 15/061,096, filed Mar. 4, 2016, Fraser et al.
U.S. Appl. No. 13/457,994, filed Apr. 27, 2012, Fraser et al.
U.S. Appl. No. 14/810,442, filed Jul. 27, 2015, Fraser et al.
U.S. Appl. No. 14/810,450, filed Jul. 27, 2015 Fraser et al.
U.S. Appl. No. 14/810,457, filed Jul. 27, 2015, Kishimoto et al.
U.S. Appl. No. 15/061,204, filed Mar. 4, 2016, Kishimoto et al.
U.S. Appl. No. 14/810,466, filed Jul. 27, 2015, Kishimoto et al.
U.S. Appl. No. 14/810,472, filed Jul. 27, 2015, Fraser et al.
U.S. Appl. No. 14/810,476, filed Jul. 27, 2015, Maldonado.
U.S. Appl. No. 14/269,047, filed May 2, 2014, Maldonado et al.
U.S. Appl. No. 14/296,204, filed Jun. 4, 2014, Maldonado et al.
U.S. Appl. No. 14/269,048, filed May 2, 2014, Maldonado.
U.S. Appl. No. 14/269,054, filed May 2, 2014, Maldonado.
U.S. Appl. No. 14/269,056, filed May 2, 2014 Maldonado et al.
U.S. Appl. No. 14/269,042, filed May 2, 2014, Kishimoto et al.
U.S. Appl. No. 14/742,583, filed Jun. 17, 2015, Kishimoto.
U.S. Appl. No. 14/751,106, filed Jun. 25, 2015, Kishimoto et al.
U.S. Appl. No. 14/846,949, filed Sep. 7, 2015, Kishimoto.
U.S. Appl. No. 14/846,952, filed Sep. 7, 2015, Kishimoto.
U.S. Appl. No. 14/846,958, filed Sep. 7, 2015, Kishimoto.
U.S. Appl. No. 16/100,040, filed Aug. 9, 2018, Kishimoto.
U.S. Appl. No. 14/934,132, filed Nov. 5, 2015, Griset et al.
U.S. Appl. No. 14/934,135, filed Nov. 5, 2015, Griset et al.
U.S. Appl. No. 15/456,520, filed Mar. 11, 2017, Johnston.
U.S. Appl. No. 15/685,648, filed Aug. 24, 2017, O'Neil.
U.S. Appl. No. 15/717,710, filed Sep. 27, 2017, Kishimoto.
U.S. Appl. No. 15/863,076, filed Jan. 5, 2018, Ilyinskii et al.
U.S. Appl. No. 15/917,742, filed Mar. 11, 2018, Johnston.
U.S. Appl. No. 16/159,166, filed Oct. 12, 2018 Ilyinskii et al.
[No Author Listed] Anaphylaxis. Manuals for Management of Individual Serious Adverse Drug Reactions. Ministry of Health, Labor and Welfare. Mar. 2008:1-34. Accessed online via http://www.info.pmda.go.jp/juutoku/file/jfm0803003.pdf.
[No Author Listed] New pharmacology. Nankodo Co. Ltd. 3rd Revised Ed. 1996:p. 468.
Abeles, PEG-ing down (and preventing?) the cause of pegloticase failure. Arthritis Res Ther. May 30, 2014;16(3):112. doi: 10.1186/ar4572.
Aronovich et al., Quantitative analysis of α-L-iduronidase expression in immunocompetent mice treated with the Sleeping Beauty transposon system. PLoS One. Oct. 21, 2013;8(10):e78161. doi: 10.1371/journal.pone.0078161. eCollection 2013.
Azzi et al., Polylactide-cyclosporin a nanoparticles for targeted immunosuppression. FASEB J. Oct. 2010;24(10):3927-38. doi: 10.1096/fj.10-154690. Epub Jun. 14, 2010.
Bi et al., High-efficiency targeted editing of large viral genomes by RNA-guided nucleases. PLoS Pathog. May 1, 2014;10(5):e1004090. doi: 10.1371/journal.ppat.1004090. eCollection May 2014.
Comas et al., New nanoformulation of rapamycin Rapatar extends lifespan in homozygous p53-/-mice by delaying carcinogenesis. Aging (Albany NY). Oct. 2012;4(10):715-22.
Crittenden et al., New therapies for gout. Annu Rev Med. 2013;64:325-37. doi: 10.1146/annurev-med-080911-105830.
Dai et al., Cellular and humoral immune responses to adenoviral vectors containing factor IX gene: tolerization of factor IX and vector antigens allows for long-term expression. Proc Natl Acad Sci U S A. Feb. 28, 1995;92(5):1401-5.
Dupont et al., The evolving role of sirolimus in renal transplantation. QJM. Jun. 2003;96(6):401-9. Review.
Garay et al., Therapeutic perspectives on uricases for gout. Joint Bone Spine. May 2012;79(3):237-42. doi: 10.1016/j.jbspin.2012.01.004. Epub Feb. 25, 2012 Review.
Goyenvalle et al., Rescue of dystrophic muscle through U7 snRNA-mediated exon skipping. Science. Dec. 3, 2004;306(5702):1796-9. Epub Nov. 4, 2004.
Kaplan et al., Transient immunosuppression with deoxyspergualin improves longevity of transgene expression and ability to readminister adenoviral vector to the mouse lung. Hum Gene Ther. Jun. 10, 1997;8(9):1095-104.
Lowenstein, The case for immunosuppression in clinical gene transfer. Mol Ther. Aug. 2005;12(2):185-6.
Matsui et al., Delivery of full-length factor VIII using a piggyBac transposon vector to correct a mouse model of hemophilia A. PLoS One. Aug. 15, 2014;9(8):e104957. doi: 10.1371/journal.pone.0104957. eCollection 2014.
Ming et al. Medical Immunology. Yunnan University Press. Feb. 28, 2009. p. 40-41.
Mori et al., Biological drug for refractory juvenile idiopathic arthritis. Clin Rheum. 2006;18(2):191-6.
Nayak et al., Prophylactic immune tolerance induced by changing the ratio of antigen-specific effector to regulatory T cells. J Thromb Haemost. Sep. 2009;7(9):1523-32. doi: 10.1111/j.1538-7836.2009.03548.x. Epub Jul. 6, 2009.
Reinders et al., New advances in the treatment of gout: review of pegloticase. Ther Clin Risk Manag. Oct. 27, 2010;6:543-50. doi: 10.2147/TCRM.S6043.
Rybak-Smith et al., Complement activation by carbon nanotubes. Adv Drug Deliv Rev. Sep. 16, 2011;63(12):1031-41. doi: 10.1016/j.addr.2011.05.012. Epub Jun. 12, 2011. Review.
Sato et al., Induction of immunotolerance by the application of chase-sulzberger effect. JP J Translpant. 1995;30(3):231-9.
Sato et al., Prolongation of the immunosuppression by repeated injections of donor antigen via the portal vein. JP J Transplant. 1995;30(2):149-54.
Sundy et al., Reduction of plasma urate levels following treatment with multiple doses of pegloticase (polyethylene glycol-conjugated uricase) in patients with treatment-failure gout: results of a phase II randomized study. Arthritis Rheum. Sep. 2008;58(9):2882-91. doi: 10.1002/art.23810.
Tardieu et al., Intracerebral administration of adeno-associated viral vector serotype rh.10 carrying human SGSH and SUMF1 cDNAs in children with mucopolysaccharidosis type IIIA disease: results of a phase I/II trial. Hum Gene Ther. Jun. 2014;25(6):506-16. doi: 10.1089/hum.2013.238. Epub May 5, 2014.
Vogt et al., Urate oxidase (rasburicase) for treatment of severe tophaceous gout. Nephrol Dial Transplant. Feb. 2005;20(2):431-3.
Wang et al., Sustained AAV-mediated dystrophin expression in a canine model of Duchenne muscular dystrophy with a brief course of immunosuppression. Mol Ther. Jun. 2007;15(6):1160-6. Epub Apr. 10, 2007.
Zhang et al., Induction of tolerance to FVIII using nanoparticles in a murine model of hemophilia A. Blood. Nov. 15, 2013;122:2337.

* cited by examiner

METHODS OF ADMINISTERING IMMUNOSUPPRESSANTS HAVING A SPECIFIED PHARMACODYNAMIC EFFECTIVE LIFE AND THERAPEUTIC MACROMOLECULES FOR THE INDUCTION OF IMMUNE TOLERANCE

RELATED APPLICATIONS

This application claims the benefit under 35 U.S.C. § 119 of U.S. provisional applications 61/819,517, filed May 3, 2013; 61/881,851, filed Sep. 24, 2013; 61/881,913, filed Sep. 24, 2013; 61/881,921, filed Sep. 24, 2013; 61/907,177, filed Nov. 21, 2013; 61/948,313, filed Mar. 5, 2014; and 61/948,384, filed Mar. 5, 2014, the entire contents of each of which are incorporated herein by reference.

FIELD OF THE INVENTION

This invention relates to methods that provide immunosuppressants and therapeutic macromolecules that are administered within a pharmacodynamically effective window of the immunosuppressants to induce immune tolerance to the therapeutic macromolecules. The methods allow shifting the immune response in favor of tolerogenic immune response development specific to the therapeutic macromolecule. The methods provided herein can be used to generate a tolerogenic immune response in a subject in which the administration of a therapeutic macromolecule is or is expected to result in an undesired immune response.

BACKGROUND OF THE INVENTION

Therapeutic treatments, such as protein or enzyme replacement therapies, often result in undesired immune responses to the particular therapeutic. Such undesired immune responses may be reduced through the use of immunosuppressant drugs. Conventional immunosuppressant drugs, however, are broad-acting. Additionally, in order to maintain immunosuppression, immunosuppressant drug therapy is generally a life-long proposition. Unfortunately, the use of broad-acting immunosuppressants are associated with a risk of severe side effects, such as tumors, infections, nephrotoxicity and metabolic disorders. Accordingly, new tolerogenic therapies would be beneficial.

SUMMARY OF THE INVENTION

In one aspect a method comprising administering an immunosuppressant to a subject in a first class of subjects at an administration dose that provides an administration pharmacodynamic effective-life, with respect to a therapeutic macromolecule, and administering the therapeutic macromolecule to the subject within the duration of the administration pharmacodynamic effective-life of the immunosuppressant is provided. In one embodiment, the pharmacodynamic effective-life has a duration that ranges from a minimum of 20 hours to a maximum of 1 month.

In one embodiment, the therapeutic macromolecule and immunosuppressant are not attached to one another. In one embodiment, the therapeutic macromolecule is not attached to a synthetic nanocarrier.

In one embodiment of any one of the methods provided herein, the method further comprises determining the administration dose of the immunosuppressant based on a test dose of the immunosuppressant. In one embodiment of any one of the methods provided herein, the test dose possesses a test pharmacodynamic effective-life with respect to the therapeutic macromolecule that has a duration that ranges from a minimum of 20 hours to a maximum of 1 month in a second class of subjects.

In another aspect, any one of the immunosuppressant compositions provided herein is provided for use in a method of inducing tolerance to a therapeutic macromolecule. In one embodiment of any one of the methods provided herein, the method comprises: (a) administering the immunosuppressant to a subject at a dose sufficient to elicit a pharmacodynamic effective-life the duration of which pharmacodynamic effective-life ranges between 20 hours to 1 month, and (b) administering the therapeutic macromolecule to said subject within the duration of said pharmacodynamic effective-life. In one embodiment of any one of the methods provided herein, the therapeutic macromolecule and immunosuppressant are not attached to one another. In one embodiment of any one of the methods provided herein, the therapeutic macromolecule is not attached to a synthetic nanocarrier.

In another aspect, a use of any one of the immunosuppressant compositions provided herein is provided for the manufacture of a medicament for use in any one of the methods provide herein, such as a method of inducing tolerance to a therapeutic macromolecule in a subject. In one embodiment, the method comprises (a) administering the immunosuppressant to a subject at a dose sufficient to elicit a pharmacodynamic effective-life the duration of which pharmacodynamic effective-life ranges between 20 hours to 1 month; and (b) administering the therapeutic macromolecule to said subject within the duration of said pharmacodynamic effective-life. In one embodiment of any one of the methods provided herein, the therapeutic macromolecule and immunosuppressant are not attached to one another. In another embodiment of any one of the methods provided herein, the therapeutic macromolecule is not attached to a synthetic nanocarrier.

In one embodiment of any one of the methods, immunosuppressants or uses provided herein, the immunosuppressant comprises synthetic nanocarriers that comprise a synthetic nanocarrier-attached immunosuppressant, implantable osmotic pumps, bi-specific antibodies, or implantable polymeric depot materials. In one embodiment of any one of the methods, immunosuppressants or uses provided herein, the immunosuppressant comprises a synthetic nanocarrier-attached immunosuppressant.

In one embodiment of any one of the methods, immunosuppressants or uses provided herein, the synthetic nanocarrier comprises lipid nanoparticles, polymeric nanoparticles, metallic nanoparticles, surfactant-based emulsions, dendrimers, buckyballs, nanowires, virus-like particles, protein particles, or nanoparticles that comprise a combination of nanomaterials, optionally, wherein such nanoparticles are lipid-polymer nanoparticles.

In one embodiment of any one of the methods, immunosuppressants or uses provided herein, the immunosuppressant comprises statins; mTOR inhibitors; TGF-β signaling agents; TGF-β receptor agonists; histone deacetylase inhibitors; corticosteroids; inhibitors of mitochondrial function; P38 inhibitors; NF-κβ inhibitors, Dexamethasone; TCPA-1; IKK VII; adenosine receptor agonists; prostaglandin E2 agonists; phosphodiesterase inhibitors; proteasome inhibitors; kinase inhibitors; G-protein coupled receptor agonists; G-protein coupled receptor antagonists; glucocorticoids; retinoids; cytokine inhibitors; cytokine receptor inhibitors; cytokine receptor activators; peroxisome proliferator-activated receptor antagonists; peroxisome proliferator-activated receptor agonists; histone deacetylase inhibitors; calcineurin inhibitors; phosphatase inhibitors; PI3 KB inhibitors; autophagy inhibitors; aryl hydrocarbon receptor inhibitors; proteasome inhibitor I (PSI); oxidized ATPs; IDO, vitamin D3; cyclosporins; aryl hydrocarbon receptor inhibitors; resveratrol; azathiopurine; 6-mercaptopurine; 6-thioguanine; FK506; sanglifehrin A; salmeterol; mycophenolate mofetil; aspirin and other COX inhibitors; niflumic acid; estriol; or triptolide. In one embodiment of any one of the methods, immunosuppressants or uses provided herein, the immunosuppressant comprises mTOR inhibitors. In one embodiment of any one of the methods, immunosuppressants or uses provided herein, the mTOR inhibitor comprises rapamycin.

In one embodiment of any one of the methods, immunosuppressants or uses provided herein, a loading of the immunosuppressant in the synthetic nanocarriers ranges between 0.0001 wt % and 50 wt %, based on the total dry recipe weight of materials in the synthetic nanocarrier (weight/weight). In one embodiment of any one of the methods, immunosuppressants or uses provided herein, the loading of the immunosuppressant in the synthetic nanocarriers ranges between 0.1 wt % and 10 wt %, based on the total dry recipe weight of materials in the synthetic nanocarrier (weight/weight).

In one embodiment of any one of the methods, immunosuppressants or uses provided herein, the therapeutic macromolecule comprises a therapeutic protein or a therapeutic polynucleotide. In one embodiment of any one of the methods, immunosuppressants or uses provided herein, the therapeutic protein comprises enzymes, enzyme cofactors, hormones, blood clotting factors, cytokines, growth factors, monoclonal antibodies or polyclonal antibodies.

In one embodiment of any one of the methods, immunosuppressants or uses provided herein, the administration pharmacodynamic effective-life has a duration that ranges from a minimum of 20 hours to a maximum of 2 weeks. In another embodiment of any one of the methods, immunosuppressants or uses provided herein, the administration pharmacodynamic effective-life has a duration that ranges from a minimum of 20 hours to a maximum of 1 week. In another embodiment of any one of the methods, immunosuppressants or uses provided herein, the administration pharmacodynamic effective-life has a duration that ranges from a minimum of 24 hours to a maximum of 2 days. In another embodiment of any one of the methods, immunosuppressants or uses provided herein, the test pharmacodynamic effective-life has a duration that ranges from a minimum of 20 hours to a maximum of 2 weeks. In another embodiment of any one of the methods, immunosuppressants or uses provided herein, the test pharmacodynamic effective-life has a duration that ranges from a minimum of 20 hours to a maximum of 1 week. In another embodiment of any one of the methods, immunosuppressants or uses provided herein, the test pharmacodynamic effective-life has a duration that ranges from a minimum of 24 hours to a maximum of 2 days.

In one embodiment of any one of the methods, immunosuppressants or uses provided herein, the administration dose of the immunosuppressant is determined based on the test dose of the immunosuppressant, together with use of allometric or isometric scaling techniques. In one embodiment of any one of the methods, immunosuppressants or uses provided herein, the first class of subjects and the second class of subjects are a same class of subjects. In one embodiment of any one of the methods, immunosuppressants or uses provided herein, the first class of subjects and the second class of subjects are different classes of subjects.

In one embodiment of any one of the methods, immunosuppressants or uses provided herein, the synthetic nanocarriers comprise lipid nanoparticles. In another embodiment of any one of the methods, immunosuppressants or uses provided herein, the synthetic nanocarriers comprise liposomes. In another embodiment of any one of the methods, immunosuppressants or uses provided herein, the synthetic nanocarriers comprise metallic nanoparticles. In another embodiment of any one of the methods, immunosuppressants or uses provided herein, the metallic nanoparticles comprise gold nanoparticles. In another embodiment of any one of the methods, immunosuppressants or uses provided herein, the synthetic nanocarriers comprise polymeric nanoparticles. In another embodiment of any one of the methods, immunosuppressants or uses provided herein, the polymeric nanoparticles comprise polymer that is a non-methoxy-terminated, pluronic polymer. In another embodiment of any one of the methods, immunosuppressants or uses provided herein, the polymeric nanoparticles comprise a polyester, polyester attached to a polyether, polyamino acid, polycarbonate, polyacetal, polyketal, polysaccharide, polyethyloxazoline or polyethyleneimine. In another embodiment of any one of the methods, immunosuppressants or uses provided herein, the polyester comprises a poly(lactic acid), poly(glycolic acid), poly(lactic-co-glycolic acid) or polycaprolactone. In another embodiment of any one of the methods, immunosuppressants or uses provided herein, the polymeric nanoparticles comprise a polyester and a polyester attached to a polyether. In another embodiment of any one of the methods, immunosuppressants or uses provided herein, the polyether comprises polyethylene glycol or polypropylene glycol.

In another embodiment of any one of the methods, immunosuppressants or uses provided herein, the mean of a particle size distribution obtained using dynamic light scattering of the synthetic nanocarriers is a diameter greater than 100 nm. In another embodiment of any one of the methods, immunosuppressants or uses provided herein, the diameter is greater than 150 nm. In another embodiment of any one of the methods, immunosuppressants or uses provided herein, the diameter is greater than 200 nm. In another embodiment of any one of the methods, immunosuppressants or uses provided herein, the diameter is greater than 250 nm. In another embodiment of any one of the methods, immunosuppressants or uses provided herein, the diameter is greater than 300 nm.

In another embodiment of any one of the methods, immunosuppressants or uses provided herein, an aspect ratio of the synthetic nanocarriers is greater than 1:1, 1:1.2, 1:1.5, 1:2, 1:3, 1:5, 1:7 or 1:10.

In another aspect, a method of manufacturing any one of the immunosuppressant and/or therapeutic macromolecule compositions provided herein is provided. In one embodiment, the method of manufacturing comprises producing a dose or dosage form of a therapeutic macromolecule and producing a dose or dosage form of an immunosuppressant. In another embodiment of any one of the methods of manufacturing provided, the step of producing a dose or dosage form of an immunosuppressant comprises attaching the immunosuppressant to synthetic nanocarriers. In another embodiment of any one of the methods of manufacturing provided, the method further comprises combining the dose or dosage form of the immunosuppressant and dose or dosage form of the therapeutic macromolecule in a kit.

In another aspect, any one of the methods of manufacturing can be for manufacturing a medicament for performing any one of the methods provided herein, and such methods of manufacturing are also provided. In one embodiment, the method of manufacturing is for manufacturing a medicament for inducing tolerance to a therapeutic macromolecule. In another embodiment, the method of manufacturing is for manufacturing a medicament for administration of an immunosuppressant and therapeutic macromolecule such that the therapeutic macromolecule is administered during the pharmacodynamic-effective life of the immunosuppressant. In another embodiment of any one of the methods of manufacturing provided herein, the immunosuppressant is attached to synthetic nanocarriers.

DETAILED DESCRIPTION OF THE INVENTION

Figure 1:
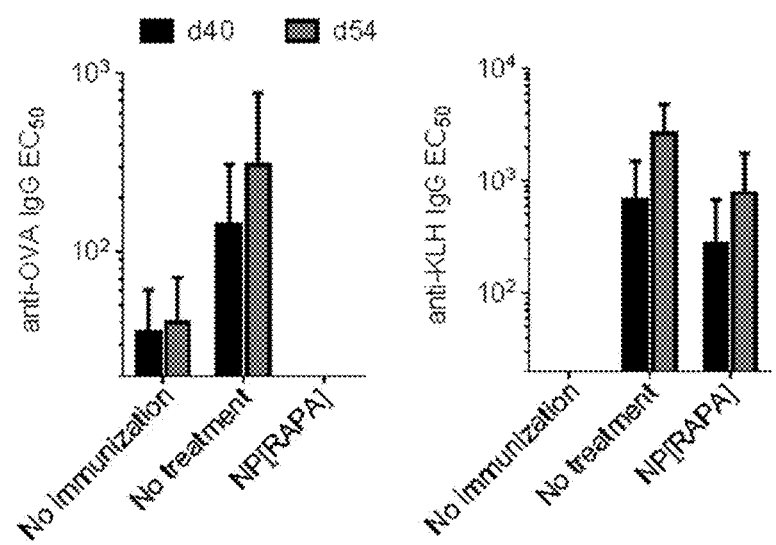
FIG. 1 shows IgG responses to encapsulated rapamycin administered with OVA and KLH.

Before describing the present invention in detail, it is to be understood that this invention is not limited to particularly exemplified materials or process parameters as such may, of course, vary. It is also to be understood that the terminology used herein is for the purpose of describing particular embodiments of the invention only, and is not intended to be limiting of the use of alternative terminology to describe the present invention.

All publications, patents and patent applications cited herein, whether supra or infra, are hereby incorporated by reference in their entirety for all purposes.

As used in this specification and the appended claims, the singular forms "a," "an" and "the" include plural referents unless the content clearly dictates otherwise. For example, reference to "a polymer" includes a mixture of two or more such molecules or a mixture of differing molecular weights of a single polymer species, reference to "a synthetic nanocarrier" includes a mixture of two or more such synthetic nanocarriers or a plurality of such synthetic nanocarriers, reference to "a RNA molecule" includes a mixture of two or more such RNA molecules or a plurality of such RNA molecules, reference to "an immunosuppressant" includes a mixture of two or more such materials or a plurality of such immunosuppressant molecules, and the like.

As used herein, the term "comprise" or variations thereof such as "comprises" or "comprising" are to be read to indicate the inclusion of any recited integer (e.g. a feature, element, characteristic, property, method/process step or limitation) or group of integers (e.g. features, element, characteristics, properties, method/process steps or limitations) but not the exclusion of any other integer or group of integers. Thus, as used herein, the term "comprising" is inclusive and does not exclude additional, unrecited integers or method/process steps.

In embodiments of any one of the compositions and methods provided herein, "comprising" may be replaced with "consisting essentially of" or "consisting of". The phrase "consisting essentially of" is used herein to require the specified integer(s) or steps as well as those which do not materially affect the character or function of the claimed invention. As used herein, the term "consisting" is used to indicate the presence of the recited integer (e.g. a feature, element, characteristic, property, method/process step or limitation) or group of integers (e.g. features, element, characteristics, properties, method/process steps or limitations) alone.

A. Introduction

The methods provided herein can allow for improved therapeutic effects as a result of the administration of a therapeutic macromolecule during a pharmacodynamically effective window (or the pharmacodynamic effective-life) of an immunosuppressant. The immunosuppressant, in some embodiments, is administered by way of attachment to synthetic nanocarriers. The methods and compositions provided herein help maximize the benefit of the immunosuppressant therapy when administering a therapeutic macromolecule to a subject.

The inventors have unexpectedly and surprisingly discovered that the problems and limitations noted above can be overcome by practicing the invention disclosed herein. In particular, the inventors have unexpectedly discovered that it is possible to provide methods comprising administering an immunosuppressant to a subject at an administration dose that provides an administration pharmacodynamic effective-life, with respect to a therapeutic macromolecule, that has a duration that ranges from a minimum of 20 hours to a maximum of 1 month and administering the therapeutic macromolecule to the subject within the duration of the administration pharmacodynamic effective-life of the immunosuppressant, wherein the immunosuppressant and therapeutic macromolecule are not coupled to one another, and the therapeutic macromolecule is not coupled to a synthetic nanocarrier. Related compositions are also provided herein.

The present invention is illustrated in the Examples below, which illustrate various compositions useful in practicing the present invention, and also provide data illustrating the concepts underlying pharmacodynamic effective-life in certain embodiments of the present invention.

The invention will now be described in more detail below.

B. Definitions

"Administration dose" or "administration dose of an immunosuppressant" means a dose of the immunosuppressant that is suitable for administration. In embodiments, the administration dose is based on a test dose of the immunosuppressant. In embodiments, the administration dose may be determined based on information from a test dose of the immunosuppressant, together with application of allometric scaling techniques. See, for instance, I. Mahmood, "Interspecies Pharmacokinetic Scaling Principles and Application of Allometric Scaling", Pine House Publishers 2005. In embodiments, the administration dose may be determined based on information from a test dose of the immunosuppressant, together with application of isometric scaling techniques, particularly if the first class of subjects and the second class of subjects are from the same species. In embodiments, the administration dose may be determined by direct experimentation in the second class of subjects, based on the test dose, rather than simply projected using allometric or isometric scaling as described above.

"Administering" or "administration" or "administer" means providing a material to a subject in a manner that is pharmacologically useful. In embodiments, "administering" or "administration" or "administer" comprises "causing to be administered." "Causing to be administered" means causing, urging, encouraging, aiding, inducing or directing, directly or indirectly, another party to administer the material.

"Administration pharmacodynamic effective-life" means a pharmacodynamic effective-life of an immunosuppressant that is determined with respect to a therapeutic macromolecule at an administration dose of the immunosuppressant and in a first class of subjects. In embodiments, the recited immunosuppressants may have an administration pharmacodynamic effective-life, with respect to a therapeutic macromolecule, that has a duration that ranges from a minimum of 20 hours to a maximum of 1 month, preferably from a minimum of 20 hours to a maximum of 2 weeks, preferably from a minimum of 20 hours to a maximum of 1 week, preferably from a minimum of 20 hours to a maximum of 5 days, preferably from a minimum of 20 hours to a maximum of 3 days, preferably from a minimum of 24 hours to a maximum of 2 days. Preferably, a therapeutic macromolecule is administered during the pharmacodynamic effective live, and thus, in some embodiments, can be administered at the same time or soon after the administration of the immunosuppressant provided that the administration of the therapeutic macromolecule occurs before the end of the duration of the pharmacodynamic effective life.

"Amount effective" in the context of a composition or dose for administration to a subject refers to an amount of the composition or dose that produces one or more desired responses in the subject, for example, the generation of a tolerogenic immune response (e.g., a reduction in the proliferation, activation, induction, survival, recruitment of therapeutic macromolecule-specific B cells or a reduction in the production of therapeutic macromolecule-specific antibodies). In some embodiments, the amount effective is a therapeutically effective amount. Therefore, in some embodiments, an amount effective is any amount of a composition or dose provided herein that produces one or more of the desired immune effects and/or therapeutic effects as provided herein. This amount can be for in vitro or in vivo purposes. For in vivo purposes, the amount can be one that a clinician would believe may have a clinical benefit for a subject in need of therapeutic macromolecule administration and/or antigen-specific immune tolerance thereto.

Amounts effective can involve reducing the level of an undesired immune response, although in some embodiments, it involves preventing an undesired immune response altogether. Amounts effective can also involve delaying the occurrence of an undesired immune response. An amount that is effective can also be an amount that produces a desired therapeutic endpoint or a desired therapeutic result. In other embodiments, the amounts effective can involve enhancing the level of a desired response, such as a therapeutic endpoint or result. Amounts effective, preferably, result in a tolerogenic immune response in a subject to an antigen, such as a therapeutic macromolecule. The achievement of any of the foregoing can be monitored by routine methods.

In some embodiments of any one of the methods provided, the amount effective is one in which the desired response persists in the subject. In other embodiments of any of the compositions and methods provided, the amount effective is one which produces a measurable desired response for a period of time.

Amounts effective will depend, of course, on the particular subject being treated; the severity of a condition, disease or disorder; the individual patient parameters including age, physical condition, size and weight; the duration of the treatment; the nature of concurrent therapy (if any); the specific route of administration and like factors within the knowledge and expertise of the health practitioner. These factors are well known to those of ordinary skill in the art and can be addressed with no more than routine experimentation. It is generally preferred that a maximum dose be used, that is, the highest safe dose according to sound medical judgment. It will be understood by those of ordinary skill in the art, however, that a patient may insist upon a lower dose or tolerable dose for medical reasons, psychological reasons or for virtually any other reason.

In general, doses of the immunosuppressants and/or therapeutic macromolecules in the compositions of the invention refer to the amount of the immunosuppressants and/or therapeutic macromolecules. Alternatively, the dose can be administered based on the number of synthetic nanocarriers that provide the desired amount of immunosuppressants.

"Antigen" means a B cell antigen or T cell antigen. "Type(s) of antigens" means molecules that share the same, or substantially the same, antigenic characteristics. In some embodiments, antigens may be proteins, polypeptides, peptides, lipoproteins, glycolipids, polynucleotides, polysaccharides or are contained or expressed in cells. In some embodiments, such as when the antigens are not well defined or characterized, the antigens may be contained within a cell or tissue preparation, cell debris, cell exosomes, conditioned media, etc.

"Antigen-specific" refers to any immune response that results from the presence of the antigen, or portion thereof, or that generates molecules that specifically recognize or bind the antigen. In some embodiments, when the antigen comprises the therapeutic macromolecule, antigen-specific may mean therapeutic macromolecule-specific. For example, where the immune response is antigen-specific antibody production, antibodies are produced that specifically bind the antigen (e.g., therapeutic macromolecule). As another example, where the immune response is antigen-specific B cell or CD4+ T cell proliferation and/or activity, the proliferation and/or activity results from recognition of the antigen, or portion thereof, alone or in complex with MHC molecules, B cells, etc.

"Assessing an immune response" refers to any measurement or determination of the level, presence or absence, reduction, increase in, etc. of an immune response in vitro or in vivo. Such measurements or determinations may be performed on one or more samples obtained from a subject. Such assessing can be performed with any of the methods provided herein or otherwise known in the art. Any one of the methods provided herein can include a step of assessing an immune response.

"Attach" or "Attached" or "Couple" or "Coupled" (and the like) means to chemically associate one entity (for example a moiety) with another. In some embodiments, the attaching is covalent, meaning that the attaching occurs in the context of the presence of a covalent bond between the two entities. In non-covalent embodiments, the non-covalent attaching is mediated by non-covalent interactions including but not limited to charge interactions, affinity interactions, metal coordination, physical adsorption, host-guest interactions, hydrophobic interactions, TT stacking interactions, hydrogen bonding interactions, van der Waals interactions, magnetic interactions, electrostatic interactions, dipole-dipole interactions, and/or combinations thereof. In embodiments, encapsulation is a form of attaching. In embodiments, therapeutic macromolecules and immunosuppressants are not attached to one another, meaning that the therapeutic macromolecules and immunosuppressants are not subjected to a process specifically intended to chemically associate one with another. In embodiments, therapeutic macromolecules and/or immunosuppressants are not attached to synthetic nanocarriers, meaning that the therapeutic macromolecules (and/or immunosuppressants) and synthetic nanocarriers are not subjected to a process specifically intended to chemically associate one with another.

"Average", as used herein, refers to the arithmetic mean unless otherwise noted.

"Class of subjects" means a grouping of subjects that share one or more common characteristics (such as biological taxonomy, eating habits, sleeping habits, immune system biology, physical presence in a location, etc.). Classes need not follow only standard biology taxonomy. Determining a result in a class of subjects can be useful to project results achievable in another class of subjects (e.g. use of animal models in predicting or exploring human disease).

"Determining" or "determine" means to ascertain a factual relationship. Determining may be accomplished in a number of ways, including but not limited to performing experiments, or making projections. For instance, a dose of an immunosuppressant or therapeutic macromolecule may be determined by starting with a test dose and using known scaling techniques (such as allometric or isometric scaling) to determine the dose for administration. Such may also be used to determine a protocol as provided herein. In another embodiment, the dose may be determined by testing various doses in a subject, i.e. through direct experimentation based on experience and guiding data. In embodiments, "determining" or "determine" comprises "causing to be determined." "Causing to be determined" means causing, urging, encouraging, aiding, inducing or directing or acting in coordination with an entity for the entity to ascertain a factual relationship; including directly or indirectly, or expressly or impliedly.

"Dosage form" means a pharmacologically and/or immunologically active material in a medium, carrier, vehicle, or device suitable for administration to a subject. Any one of the compositions or doses provided herein may be in a dosage form.

"Dose" refers to a specific quantity of a pharmacologically and/or immunologically active material for administration to a subject for a given time.

"Encapsulate" means to enclose at least a portion of a substance within a synthetic nanocarrier. In some embodiments, a substance is enclosed completely within a synthetic nanocarrier. In other embodiments, most or all of a substance that is encapsulated is not exposed to the local environment external to the synthetic nanocarrier. In other embodiments, no more than 50%, 40%, 30%, 20%, 10% or 5% (weight/weight) is exposed to the local environment. Encapsulation is distinct from absorption, which places most or all of a substance on a surface of a synthetic nanocarrier, and leaves the substance exposed to the local environment external to the synthetic nanocarrier.

"Generating" means causing an action, such as a physiologic or immunologic response (e.g., a tolerogenic immune response) to occur, either directly oneself or indirectly.

"Identifying a subject" is any action or set of actions that allows a clinician to recognize a subject as one who may benefit from the methods, compositions or kits provided herein. Preferably, the identified subject is one who is in need of a therapeutic benefit from a therapeutic macromolecule and/or in which an anti-therapeutic macromolecule-specific antibody response has occurred or is expected to occur (or is at risk of occurring) as provided herein. The action or set of actions may be either directly oneself or indirectly. In one embodiment of any one of the methods provided herein, the method further comprises identifying a subject in need of a method, composition or kit as provided herein.

"Immunosuppressant" means a compound that causes an APC to have an immunosuppressive effect (e.g., tolerogenic effect) or a T cell or a B cell to be suppressed. An immunosuppressive effect generally refers to the production or expression of cytokines or other factors by the APC that reduces, inhibits or prevents an undesired immune response or that promotes a desired immune response, such as a regulatory immune response. When the APC acquires an immunosuppressive function (under the immunosuppressive effect) on immune cells that recognize an antigen presented by this APC, the immunosuppressive effect is said to be specific to the presented antigen. Without being bound by any particular theory, it is thought that the immunosuppressive effect is a result of the immunosuppressant being delivered to the APC, preferably in the presence of an antigen. In one embodiment, the immunosuppressant is one that causes an APC to promote a regulatory phenotype in one or more immune effector cells. For example, the regulatory phenotype may be characterized by the inhibition of the production, induction, stimulation or recruitment of antigen-specific CD4+ T cells or B cells, the inhibition of the production of antigen-specific antibodies, the production, induction, stimulation or recruitment of Treg cells (e.g., CD4+CD25highFoxP3+ Treg cells), etc. This may be the result of the conversion of CD4+ T cells or B cells to a regulatory phenotype. This may also be the result of induction of FoxP3 in other immune cells, such as CD8+ T cells, macrophages and iNKT cells. In one embodiment, the immunosuppressant is one that affects the response of the APC after it processes an antigen. In another embodiment, the immunosuppressant is not one that interferes with the processing of the antigen. In a further embodiment, the immunosuppressant is not an apoptotic-signaling molecule. In another embodiment, the immunosuppressant is not a phospholipid.

Immunosuppressants include, but are not limited to, statins; mTOR inhibitors, such as rapamycin or a rapamycin analog; TGF-β signaling agents; TGF-β receptor agonists; histone deacetylase inhibitors, such as Trichostatin A; corticosteroids; inhibitors of mitochondrial function, such as rotenone; P38 inhibitors; NF-κβ inhibitors, such as 6Bio, Dexamethasone, TCPA-1, IKK VII; adenosine receptor agonists; prostaglandin E2 agonists (PGE2), such as Misoprostol; phosphodiesterase inhibitors, such as phosphodiesterase 4 inhibitor (PDE4), such as Rolipram; proteasome inhibitors; kinase inhibitors; G-protein coupled receptor agonists; G-protein coupled receptor antagonists; glucocorticoids; retinoids; cytokine inhibitors; cytokine receptor inhibitors; cytokine receptor activators; peroxisome proliferator-activated receptor antagonists; peroxisome proliferator-activated receptor agonists; histone deacetylase inhibitors; calcineurin inhibitors; phosphatase inhibitors; PI3 KB inhibitors, such as TGX-221; autophagy inhibitors, such as 3-Methyladenine; aryl hydrocarbon receptor inhibitors; proteasome inhibitor I (PSI); and oxidized ATPs, such as P2X receptor blockers. Immunosuppressants also include IDO, vitamin D3, cyclosporins, such as cyclosporine A, aryl hydrocarbon receptor inhibitors, resveratrol, azathiopurine (Aza), 6-mercaptopurine (6-MP), 6-thioguanine (6-TG), FK506, sanglifehrin A, salmeterol, mycophenolate mofetil (MMF), aspirin and other COX inhibitors, niflumic acid, estriol, methotrexate and triptolide. In embodiments, the immunosuppressant may comprise any of the agents provided herein.

The immunosuppressant can be a compound that directly provides the immunosuppressive effect on APCs or it can be a compound that provides the immunosuppressive effect indirectly (i.e., after being processed in some way after administration). Immunosuppressants, therefore, include prodrug forms of any of the compounds provided herein.

In embodiments of any one of the methods, compositions or kits provided herein, the immunosuppressants provided herein are attached to synthetic nanocarriers. In preferable embodiments, the immunosuppressant is an element that is in addition to the material that makes up the structure of the synthetic nanocarrier. For example, in one embodiment, where the synthetic nanocarrier is made up of one or more polymers, the immunosuppressant is a compound that is in addition and attached to the one or more polymers. As another example, in one embodiment, where the synthetic nanocarrier is made up of one or more lipids, the immunosuppressant is again in addition and attached to the one or more lipids. In embodiments, such as where the material of the synthetic nanocarrier also results in an immunosuppressive effect, the immunosuppressant is an element present in addition to the material of the synthetic nanocarrier that results in an immunosuppressive effect.

In embodiments of any one of the methods, compositions or kits provided herein, the immunosuppressant is in a form, such as a nanocrystalline form, whereby the form of the immunosuppressant itself is a particle or particle-like. In embodiments, such forms mimic a virus or other foreign pathogen. Many drugs have been nanonized and appropriate methods for producing such drug forms would be known to one of ordinary skill in the art. Drug nanocrystals, such as nanocrystalline rapamycin are known to those of ordinary skill in the art (Katteboinaa, et al. 2009, International Journal of PharmTech Resesarch; Vol. 1, No. 3; pp 682-694. As used herein a "drug nanocrystal" refers to a form of a drug (e.g., an immunosuppressant) that does not include a carrier or matrix material. In some embodiments, drug nanocrystals comprise 90%, 95%, 98% or 99% or more drug. Methods for producing drug nanocrystals include, without limitation, milling, high pressure homogenization, precipitation, spray drying, rapid expansion of supercritical solution (RESS), Nanoedge® technology (Baxter Healthcare), and Nanocrystal Technology™ (Elan Corporation). In some embodiments, a surfactant or a stabilizer may be used for steric or electrostatic stability of the drug nanocrystal. In some embodiments the nanocrystal or nanocrytalline form of an immunosuppressant may be used to increase the solubility, stability, and/or bioavailability of the immunosuppressant, particularly immunosuppressants that are insoluble or labile. In some embodiments, administration of the immunosuppressant in nanocrystalline form induces tolerance to a therapeutic macromolecule.

Other exemplary immunosuppressants include, but are not limited, small molecule drugs, natural products, antibodies (e.g., antibodies against CD20, CD3, CD4), biologics-based drugs, carbohydrate-based drugs, nanoparticles, liposomes, RNAi, antisense nucleic acids, aptamers, methotrexate, NSAIDs; fingolimod; natalizumab; alemtuzumab; anti-CD3; tacrolimus (FK506); cytokines and growth factors, such as TGF-β and IL-10; etc. In any one of the aspects or embodiments provided herein the immunosuppressants can be attached to synthetic nanocarriers or delivered in the form of implantable osmotic pumps, such as ALZET® implantable osmotic pumps, implantable depot materials or bi-specific antibodies (anti-CD22+Ag, anti-GITR+Ag, or anti-LAG3+Ag). Further immunosuppressants, are known to those of skill in the art, and the invention is not limited in this respect.

"Load" when attached to a synthetic nanocarrier of the immunosuppressant is the amount of the immunosuppressant attached to a synthetic nanocarrier based on the total dry recipe weight of materials in the synthetic nanocarrier (weight/weight). Generally, the load is calculated as an average across a population of synthetic nanocarriers. In one embodiment, load of the immunosuppressant on average across synthetic nanocarriers ranges between 0.0001 wt % and 99 wt %. In another embodiment, the load of the immunosuppressant ranges between 0.01 wt % and 50 wt %. In another embodiment, the load is between 0.1 wt % and 20 wt %. In a further embodiment, the load of the immunosuppressant ranges between 0.1 wt % and 10 wt %. In still a further embodiment, the load of the immunosuppressant ranges between 1 wt % and 10 wt %. In still a further embodiment, the load is between 7 wt % and 20 wt %. In yet another embodiment, the load of the immunosuppressant ranges at least 0.1 wt %, at least 0.2 wt %, at least 0.3 wt %, at least 0.4 wt %, at least 0.5 wt %, at least 0.6 wt %, at least 0.7 wt %, at least 0.8 wt %, at least 0.9 wt %, at least 1 wt %, at least 2 wt %, at least 3 wt %, at least 4 wt %, at least 5 wt %, at least 6 wt %, at least at least 7 wt %, at least 8 wt %, at least 9 wt %, at least 10 wt %, at least 11 wt %, at least 12 wt %, at least 13 wt %, at least 14 wt %, at least 15 wt %, at least 16 wt %, at least 17 wt %, at least 18 wt %, at least 19 wt %, at least 20 wt %, at least 25 wt %, at least 30 wt %, at least 40 wt %, at least 50 wt %, at least 60 wt %, at least 70 wt %, at least 80 wt %, at least 90 wt %, at least 95 wt %, at least 96 wt %, at least 97 wt %, at least 98 wt % or at least 99 wt % on average across the population of synthetic nanocarriers. In yet a further embodiment, the load of the immunosuppressant is 0.1 wt %, 0.2 wt %, 0.3 wt %, 0.4 wt %, 0.5 wt %, 0.6 wt %, 0.7 wt %, 0.8 wt %, 0.9 wt %, 1 wt %, 2 wt %, 3 wt %, 4 wt %, 5 wt %, 6 wt %, 7 wt %, 8 wt %, 9 wt %, 10 wt %, 11 wt %, 12 wt %, 13 wt %, 14 wt %, 15 wt %, 16 wt %, 17 wt %, 18 wt %, 19 wt % or 20 wt % on average across the population of synthetic nanocarriers. In some embodiments of the above embodiments, the load of the immunosuppressant is no more than 25 wt % on average across a population of synthetic nanocarriers. In embodiments, the load is calculated as may be described in the Examples or as otherwise known in the art.

In some embodiments, when the form of the immunosuppressant is itself a particle or particle-like, such as a nanocrystalline immunosuppressant, the load of immunosuppressant is the amount of the immunosuppressant in the particles or the like (weight/weight). In such embodiments, the load can approach 97%, 98%, 99% or more.

"Maximum dimension of a synthetic nanocarrier" means the largest dimension of a nanocarrier measured along any axis of the synthetic nanocarrier. "Minimum dimension of a synthetic nanocarrier" means the smallest dimension of a synthetic nanocarrier measured along any axis of the synthetic nanocarrier. For example, for a spheroidal synthetic nanocarrier, the maximum and minimum dimension of a synthetic nanocarrier would be substantially identical, and would be the size of its diameter. Similarly, for a cuboidal synthetic nanocarrier, the minimum dimension of a synthetic nanocarrier would be the smallest of its height, width or length, while the maximum dimension of a synthetic nanocarrier would be the largest of its height, width or length. In an embodiment, a minimum dimension of at least 75%, preferably at least 80%, more preferably at least 90%, of the synthetic nanocarriers in a sample, based on the total number of synthetic nanocarriers in the sample, is equal to or greater than 100 nm. In an embodiment, a maximum dimension of at least 75%, preferably at least 80%, more preferably at least 90%, of the synthetic nanocarriers in a sample, based on the total number of synthetic nanocarriers in the sample, is equal to or less than 5 µm. Preferably, a minimum dimension of at least 75%, preferably at least 80%, more preferably at least 90%, of the synthetic nanocarriers in a sample, based on the total number of synthetic nanocarriers in the sample, is greater than 110 nm, more preferably greater than 120 nm, more preferably greater than 130 nm, and more preferably still greater than 150 nm. Aspects ratios of the maximum and minimum dimensions of synthetic nanocarriers may vary depending on the embodiment. For instance, aspect ratios of the maximum to minimum dimensions of the synthetic nanocarriers may vary from 1:1 to 1,000,000:1, preferably from 1:1 to 100,000:1, more preferably from 1:1 to 10,000:1, more preferably from 1:1 to 1000:1, still more preferably from 1:1 to 100:1, and yet more preferably from 1:1 to 10:1. Preferably, a maximum dimension of at least 75%, preferably at least 80%, more preferably at least 90%, of the synthetic nanocarriers in a sample, based on the total number of synthetic nanocarriers in the sample is equal to or less than 3 µm, more preferably equal to or less than 2 µm, more preferably equal to or less than 1 µm, more preferably equal to or less than 800 nm, more preferably equal to or less than 600 nm, and more preferably still equal to or less than 500 nm. In preferred embodiments, a minimum dimension of at least 75%, preferably at least 80%, more preferably at least 90%, of the synthetic nanocarriers in a sample, based on the total number of synthetic nanocarriers in the sample, is equal to or greater than 100 nm, more preferably equal to or greater than 120 nm, more preferably equal to or greater than 130 nm, more preferably equal to or greater than 140 nm, and more preferably still equal to or greater than 150 nm. Measurement of synthetic nanocarrier dimensions (e.g., effective diameter) may be obtained, in some embodiments, by suspending the synthetic nanocarriers in a liquid (usually aqueous) media and using dynamic light scattering (DLS) (e.g. using a Brookhaven ZetaPALS instrument). For example, a suspension of synthetic nanocarriers can be diluted from an aqueous buffer into purified water to achieve a final synthetic nanocarrier suspension concentration of approximately 0.01 to 0.1 mg/mL. The diluted suspension may be prepared directly inside, or transferred to, a suitable cuvette for DLS analysis. The cuvette may then be placed in the DLS, allowed to equilibrate to the controlled temperature, and then scanned for sufficient time to acquire a stable and reproducible distribution based on appropriate inputs for viscosity of the medium and refractive indicies of the sample. The effective diameter, or mean of the distribution, is then reported. Determining the effective sizes of high aspect ratio, or non-spheroidal, synthetic nanocarriers may require augmentative techniques, such as electron microscopy, to obtain more accurate measurements. "Dimension" or "size" or "diameter" of synthetic nanocarriers means the mean of a particle size distribution, for example, obtained using dynamic light scattering.

"Non-methoxy-terminated polymer" means a polymer that has at least one terminus that ends with a moiety other than methoxy. In some embodiments, the polymer has at least two termini that ends with a moiety other than methoxy. In other embodiments, the polymer has no termini that ends with methoxy. "Non-methoxy-terminated, pluronic polymer" means a polymer other than a linear pluronic polymer with methoxy at both termini. Polymeric nanoparticles as provided herein can comprise non-methoxy-terminated polymers or non-methoxy-terminated, pluronic polymers.

"Pharmaceutically acceptable excipient" or "pharmaceutically acceptable carrier" means a pharmacologically inactive material used together with a pharmacologically active material to formulate the compositions. Pharmaceutically acceptable excipients comprise a variety of materials known in the art, including but not limited to saccharides (such as glucose, lactose, and the like), preservatives such as antimicrobial agents, reconstitution aids, colorants, saline (such as phosphate buffered saline), and buffers.

"Pharmacodynamic effective-life" means a first, dose-dependent period that is after the administration of an immunosuppressant to a subject, during which administration of antigen results in antigen-specific tolerance in the subject measurable during a second period starting at a time ranging from five days to 3 months after administration of the antigen. In embodiments, the pharmacodynamic effective-life can be measured as the mean of individual pharmacodynamic effective-lives measured in one or more subjects, such as a first class of subjects, and measured singly or multiple times in each measured subject.

"Providing" means an action or set of actions that an individual performs that supply a needed item or set of items or methods for practicing of the present invention. The action or set of actions may be taken either directly oneself or indirectly.

"Providing a subject" is any action or set of actions that causes a clinician to come in contact with a subject and administer a composition provided herein thereto or to perform a method provided herein thereupon. Preferably, the subject is one who is in need of therapeutic macromolecule administration and antigen-specific tolerance thereto. The action or set of actions may be taken either directly oneself or indirectly. In one embodiment of any one of the methods provided herein, the method further comprises providing a subject.

"Subject" means animals, including warm blooded mammals such as humans and primates; avians; domestic household or farm animals such as cats, dogs, sheep, goats, cattle, horses and pigs; laboratory animals such as mice, rats and guinea pigs; fish; reptiles; zoo and wild animals; and the like.

"Synthetic nanocarrier(s)" means a discrete object that is not found in nature, and that possesses at least one dimension that is less than or equal to 5 microns in size. Albumin nanoparticles are generally included as synthetic nanocarriers, however in certain embodiments the synthetic nanocarriers do not comprise albumin nanoparticles. In embodiments, synthetic nanocarriers do not comprise chitosan. In other embodiments, synthetic nanocarriers are not lipid-based nanoparticles. In further embodiments, synthetic nanocarriers do not comprise a phospholipid.

A synthetic nanocarrier can be, but is not limited to, one or a plurality of lipid-based nanoparticles (also referred to herein as lipid nanoparticles, i.e., nanoparticles where the majority of the material that makes up their structure are lipids), polymeric nanoparticles, metallic nanoparticles, surfactant-based emulsions, dendrimers, buckyballs, nanowires, virus-like particles (i.e., particles that are primarily made up of viral structural proteins but that are not infectious or have low infectivity), peptide or protein-based particles (also referred to herein as protein particles, i.e., particles where the majority of the material that makes up their structure are peptides or proteins) (such as albumin nanoparticles) and/or nanoparticles that are developed using a combination of nanomaterials such as lipid-polymer nanoparticles. Synthetic nanocarriers may be a variety of different shapes, including but not limited to spheroidal, cuboidal, pyramidal, oblong, cylindrical, toroidal, and the like. Synthetic nanocarriers according to the invention comprise one or more surfaces. Exemplary synthetic nanocarriers that can be adapted for use in the practice of the present invention comprise: (1) the biodegradable nanoparticles disclosed in U.S. Pat. No. 5,543,158 to Gref et al., (2) the polymeric nanoparticles of Published US Patent Application 20060002852 to Saltzman et al., (3) the lithographically constructed nanoparticles of Published US Patent Application 20090028910 to DeSimone et al., (4) the disclosure of WO 2009/051837 to von Andrian et al., (5) the nanoparticles disclosed in Published US Patent Application 2008/0145441 to Penades et al., (6) the protein nanoparticles disclosed in Published US Patent Application 20090226525 to de los Rios et al., (7) the virus-like particles disclosed in published US Patent Application 20060222652 to Sebbel et al., (8) the nucleic acid attached virus-like particles disclosed in published US Patent Application 20060251677 to Bachmann et al., (9) the virus-like particles disclosed in WO2010047839A1 or WO2009106999A2, (10) the nanoprecipitated nanoparticles disclosed in P. Paolicelli et al., "Surface-modified PLGA-based Nanoparticles that can Efficiently Associate and Deliver Virus-like Particles" Nanomedicine. 5(6):843-853 (2010), (11) apoptotic cells, apoptotic bodies or the synthetic or semisynthetic mimics disclosed in U.S. Publication 2002/0086049, or (12) those of Look et al., Nanogel-based delivery of mycophenolic acid ameliorates systemic lupus erythematosus in mice" J. Clinical Investigation 123(4):1741-1749 (2013). In embodiments, synthetic nanocarriers may possess an aspect ratio greater than 1:1, 1:1.2, 1:1.5, 1:2, 1:3, 1:5, 1:7, or greater than 1:10.

Synthetic nanocarriers according to the invention that have a minimum dimension of equal to or less than about 100 nm, preferably equal to or less than 100 nm, do not comprise a surface with hydroxyl groups that activate complement or alternatively comprise a surface that consists essentially of moieties that are not hydroxyl groups that activate complement. In a preferred embodiment, synthetic nanocarriers according to the invention that have a minimum dimension of equal to or less than about 100 nm, preferably equal to or less than 100 nm, do not comprise a surface that substantially activates complement or alternatively comprise a surface that consists essentially of moieties that do not substantially activate complement. In a more preferred embodiment, synthetic nanocarriers according to the invention that have a minimum dimension of equal to or less than about 100 nm, preferably equal to or less than 100 nm, do not comprise a surface that activates complement or alternatively comprise a surface that consists essentially of moieties that do not activate complement. In embodiments, synthetic nanocarriers exclude virus-like particles. In embodiments, synthetic nanocarriers may possess an aspect ratio greater than 1:1, 1:1.2, 1:1.5, 1:2, 1:3, 1:5, 1:7, or greater than 1:10.

"Test dose" or "test dose of an immunosuppressant" means a dose of the immunosuppressant that is for testing.

"Test pharmacodynamic effective-life" means a pharmacodynamic effective-life of an immunosuppressant that is determined with respect to a therapeutic macromolecule at a test dose of the immunosuppressant and in a second class of subjects. In embodiments, the recited immunosuppressants may have a test pharmacodynamic effective-life, with respect to a therapeutic macromolecule, that has a duration that ranges from a minimum of 20 hours to a maximum of 1 month, preferably from a minimum of 20 hours to a maximum of 2 weeks, preferably from a minimum of 20 hours to a maximum of 1 week, preferably from a minimum of 20 hours to a maximum of 5 days, preferably from a minimum of 20 hours to a maximum of 3 days, preferably from a minimum of 24 hours to a maximum of 2 days.

A "therapeutic macromolecule" refers to any protein, carbohydrate, lipid or nucleic acid that may be administered to a subject and have a therapeutic effect. In some embodiments, administration of the therapeutic macromolecule to a subject may result in an undesired immune response, including production of anti-therapeutic macromolecule-specific antibodies. As described herein, administration of a therapeutic macromolecule as provided herein, in some embodiments, can enhance the therapeutic effectiveness of the therapeutic macromolecule, such as by reducing undesired immune responses thereto. In some embodiments, the therapeutic macromolecule may be a therapeutic polynucleotide or therapeutic protein.

"Therapeutic polynucleotide" means any polynucleotide or polynucleotide-based therapy that may be administered to a subject and have a therapeutic effect. Such therapies include gene silencing. Examples of such therapy are known in the art, and include, but are not limited to, naked RNA (including messenger RNA, modified messenger RNA, and forms of RNAi). Examples of other therapeutic polynucleotides are provided elsewhere herein. Therapeutic polynucleotides may be produced in, on or by cells and also may be obtained using cell free or from fully synthetic in vitro methods. Subjects, therefore, include any subject that is in need of treatment with any of the foregoing. Such subject include those that will receive any of the foregoing.

"Therapeutic protein" means any protein or protein-based therapy that may be administered to a subject and have a therapeutic effect. Such therapies include protein replacement and protein supplementation therapies. Such therapies also include the administration of exogenous or foreign proteins, antibody therapies, and cell or cell-based therapies. Therapeutic proteins comprise, but are not limited to, enzymes, enzyme cofactors, hormones, blood clotting factors, cytokines, growth factors, monoclonal antibodies, antibody-drug conjugates, and polyclonal antibodies. Examples of other therapeutic proteins are provided elsewhere herein. Therapeutic proteins may be produced in, on or by cells and may be obtained from such cells or administered in the form of such cells. In embodiments, the therapeutic protein is produced in, on or by mammalian cells, insect cells, yeast cells, bacteria cells, plant cells, transgenic animal cells, transgenic plant cells, etc. The therapeutic protein may be recombinantly produced in such cells. The therapeutic protein may be produced in, on or by a virally transformed cell. Subjects, therefore, include any subject that is in need of treatment with any of the foregoing. Such subject include those that will receive any of the foregoing.

C. Compositions Useful in the Practice of the Methods

Provided herein are methods and related compositions useful for reducing the generation of undesired immune responses and promoting the generation of tolerogenic immune responses that are specific to therapeutic macromolecules. The methods and compositions help maximize the benefit of administering an immunosuppressant by administering a therapeutic macromolecule during a pharmacodynamic effective-life, with respect to the therapeutic macromolecule, of the immunosuppressant. The inventive methods can be practiced with subjects in which a tolerogenic immune response to therapeutic macromolecules is desired. Such subjects include those that will be administered a therapeutic macromolecule. Of specific usefulness in the practice of the present invention are immunosuppressants that have a pharmacodynamic effective-life, with respect to a therapeutic macromolecule, that has a duration that ranges from a minimum of 20 hours to a maximum of 1 month. A variety of immunosuppressants may be used in the practice of the present invention.

In certain embodiments, the recited immunosuppressant may be in the form of a device such as an implantable osmotic pump. One such implantable osmotic pump that may be used in the practice of the present invention is the ALZET® brand implantable osmotic pump (available from the Durect Corporation, Cupertino Calif.). ALZET® brand osmotic pumps are miniature implantable osmotic pumps that can continuously deliver drugs, hormones and other test agents at controlled rates from one day to four weeks without the need for external connections, frequent handling or repeated dosing. These infusion pumps can be used for systemic administration when implanted under the skin or in the body. They can be attached to a catheter for intravenous, intracerebral, or intra-arterial infusion or for targeted delivery, where the effects of a drug or test agent are localized in a particular tissue or organ. The pumps are powered by the osmotic difference between the pump and the body fluid of an animal and thus require no external power source. ALZET pumps have been used to target delivery to a wide variety of sites including the spinal cord, spleen, liver, organ or tissue transplants, and wound healing sites. See, for example, S. M. Stepkowski et al., "Inhibition of host-versus-graft and graft-versus-host responses after small bowel transplantation in rats by rapamycin." Transplantation (1992) 53(-2-):258-264. Other information regarding ALZET® brand osmotic pumps is available at alzet.com.

In embodiments, the recited immunosuppressant may be in the form of bi-specific antibodies (BsAbs) with one variable region designed to target a receptor for antigen (such as BCR) that selectively binds the macromolecules of interest on the immune cells and the other variable region designed to bind a target (such as cell surface receptors) on immune cells that are involved in stimulating tolerance. In another embodiment, the BsAbs consist of one variable region (anti-idiotypic region or antibody) designed to target the variable region of another antibody that binds to the macromolecule of interest and the other variable region designed to bind a target (such as cell surface receptors) on immune cells that are involved in stimulating tolerance. By virtue of combination of two binding specificities, the selectivity and potency of the BsAb immunosuppressant can be improved and immune tolerance of the macromolecules of interest can be induced. In embodiments, immunosuppressant BsAbs targets include, but are not limited to CD-19, CD-20, CD-21, CD-22 on B-cells (Ref: M. R. Clatworthy, American Journal of Transplantation 2011; 11: 1359-1367), and GITR (Glucocorticoid-induced tumor necrosis factor (TNF) receptor family-related gene. GITR is a type I transmembrane protein with homology to TNF receptor family members. GITR is expressed at low levels on resting CD4+ and CD8+ T cells and up-regulated following T-cell activation. Ligation of GITR provides a costimulatory signal that enhances both CD4+ and CD8+ T-cell proliferation and effector functions, particularly in the setting of suboptimal T-cell receptor (TCR) stimulation. In addition, GITR is expressed constitutively at high levels on regulatory T cells (Tregs) and has been explored as a potential target for overcoming Treg suppression. Signaling through GITR, using GITR ligand, abrogates the suppressive effects of Tregs, enhances autoreactive and alloreactive T-cell responses, and exacerbates autoimmunity). Another BsAbs target may comprise LAG3 (aka CD223). CD223 binds to MHC class II with higher affinity than CD4, and it is thought that this interaction is involved in the negative regulation of T-cell activation and homeostatic proliferation. Furthermore, CD223 is expressed by CD4+CD25+ regulatory T cells, and it has been suggested that CD223 may be involved in their regulatory function), in addition to other such targets known in the art.

In certain embodiments, the recited immunosuppressant may be in the form of implantable polymeric depot materials. In embodiments, implantable polymeric depot materials comprise a microporous, solid matrix of a biocompatible, biodegradable thermoplastic polymer, a rate modifying agent and a bioactive material. The matrix is formed in a solution or suspension to form an injectable liquid. The matrix controls the rate and extent of release of the bioactive agent from the matrix. The process by which the depots are formed in part is responsible for development of rate and release control. Interaction of the liquid composition with an aqueous medium either in situ in the body or external to the body to coagulate the polymer system at least in part causes the desired controlled release profile as a function of the variation of the components and concentrations of the various components. Exemplary implantable polymeric depot materials can be found in U.S. Pat. No. 5,702,716 to Dunn et al., entitled "Polymeric compositions useful as controlled release implants"; and U.S. Pat. No. 6,130,200 to Brodbeck et al., entitled "Gel composition and methods".

The recited immunosuppressants may also be administered in the form of synthetic nanocarriers that comprise the immunosuppressants. A wide variety of synthetic nanocarriers can be used according to the invention. In some embodiments, synthetic nanocarriers are spheres or spheroids. In some embodiments, synthetic nanocarriers are flat or plate-shaped. In some embodiments, synthetic nanocarriers are cubes or cubic. In some embodiments, synthetic nanocarriers are ovals or ellipses. In some embodiments, synthetic nanocarriers are cylinders, cones, or pyramids.

In some embodiments, it is desirable to use a population of synthetic nanocarriers that is relatively uniform in terms of size or shape so that each synthetic nanocarrier has similar properties. For example, at least 80%, at least 90%, or at least 95% of the synthetic nanocarriers, based on the total number of synthetic nanocarriers, may have a minimum dimension or maximum dimension that falls within 5%, 10%, or 20% of the average diameter or average dimension of the synthetic nanocarriers.

Synthetic nanocarriers can be solid or hollow and can comprise one or more layers. In some embodiments, each layer has a unique composition and unique properties relative to the other layer(s). To give but one example, synthetic nanocarriers may have a core/shell structure, wherein the core is one layer (e.g. a polymeric core) and the shell is a second layer (e.g. a lipid bilayer or monolayer). Synthetic nanocarriers may comprise a plurality of different layers.

In some embodiments, synthetic nanocarriers may optionally comprise one or more lipids. In some embodiments, a synthetic nanocarrier may comprise a liposome. In some embodiments, a synthetic nanocarrier may comprise a lipid bilayer. In some embodiments, a synthetic nanocarrier may comprise a lipid monolayer. In some embodiments, a synthetic nanocarrier may comprise a micelle. In some embodiments, a synthetic nanocarrier may comprise a core comprising a polymeric matrix surrounded by a lipid layer (e.g., lipid bilayer, lipid monolayer, etc.). In some embodiments, a synthetic nanocarrier may comprise a non-polymeric core (e.g., metal particle, quantum dot, ceramic particle, bone particle, viral particle, proteins, nucleic acids, carbohydrates, etc.) surrounded by a lipid layer (e.g., lipid bilayer, lipid monolayer, etc.).

In other embodiments, synthetic nanocarriers may comprise metal particles, quantum dots, ceramic particles, etc. In some embodiments, a non-polymeric synthetic nanocarrier is an aggregate of non-polymeric components, such as an aggregate of metal atoms (e.g., gold atoms).

In some embodiments, synthetic nanocarriers may optionally comprise one or more amphiphilic entities. In some embodiments, an amphiphilic entity can promote the production of synthetic nanocarriers with increased stability, improved uniformity, or increased viscosity. In some embodiments, amphiphilic entities can be associated with the interior surface of a lipid membrane (e.g., lipid bilayer, lipid monolayer, etc.). Many amphiphilic entities known in the art are suitable for use in making synthetic nanocarriers in accordance with the present invention. Such amphiphilic entities include, but are not limited to, phosphoglycerides; phosphatidylcholines; dipalmitoyl phosphatidylcholine (DPPC); dioleylphosphatidyl ethanolamine (DOPE); dioleyloxypropyltriethylammonium (DOTMA); dioleoylphosphatidylcholine; cholesterol; cholesterol ester; diacylglycerol; diacylglycerolsuccinate; diphosphatidyl glycerol (DPPG); hexanedecanol; fatty alcohols such as polyethylene glycol (PEG); polyoxyethylene-9-lauryl ether; a surface active fatty acid, such as palmitic acid or oleic acid; fatty acids; fatty acid monoglycerides; fatty acid diglycerides; fatty acid amides; sorbitan trioleate (Span®85) glycocholate; sorbitan monolaurate (Span®20); polysorbate 20 (Tween®20); polysorbate 60 (Tween®60); polysorbate 65 (Tween®65); polysorbate 80 (Tween®80); polysorbate 85 (Tween®85); polyoxyethylene monostearate; surfactin; a poloxomer; a sorbitan fatty acid ester such as sorbitan trioleate; lecithin; lysolecithin; phosphatidylserine; phosphatidylinositol; sphingomyelin; phosphatidylethanolamine (cephalin); cardiolipin; phosphatidic acid; cerebrosides; dicetylphosphate; dipalmitoylphosphatidylglycerol; stearylamine; dodecylamine; hexadecyl-amine; acetyl palmitate; glycerol ricinoleate; hexadecyl stearate; isopropyl myristate; tyloxapol; poly(ethylene glycol)5000-phosphatidylethanolamine; poly(ethylene glycol)400-monostearate; phospholipids; synthetic and/or natural detergents having high surfactant properties; deoxycholates; cyclodextrins; chaotropic salts; ion pairing agents; and combinations thereof. An amphiphilic entity component may be a mixture of different amphiphilic entities. Those skilled in the art will recognize that this is an exemplary, not comprehensive, list of substances with surfactant activity. Any amphiphilic entity may be used in the production of synthetic nanocarriers to be used in accordance with the present invention.

In some embodiments, synthetic nanocarriers may optionally comprise one or more carbohydrates. Carbohydrates may be natural or synthetic. A carbohydrate may be a derivatized natural carbohydrate. In certain embodiments, a carbohydrate comprises monosaccharide or disaccharide, including but not limited to glucose, fructose, galactose, ribose, lactose, sucrose, maltose, trehalose, cellbiose, mannose, xylose, arabinose, glucoronic acid, galacturonic acid, mannuronic acid, glucosamine, galactosamine, and neuramic acid. In certain embodiments, a carbohydrate is a polysaccharide, including but not limited to pullulan, cellulose, microcrystalline cellulose, hydroxypropyl methylcellulose (HPMC), hydroxycellulose (HC), methylcellulose (MC), dextran, cyclodextran, glycogen, hydroxyethylstarch, carageenan, glycon, amylose, chitosan, N,O-carboxylmethylchitosan, algin and alginic acid, starch, chitin, inulin, konjac, glucommannan, pustulan, heparin, hyaluronic acid, curdlan, and xanthan. In embodiments, the synthetic nanocarriers do not comprise (or specifically exclude) carbohydrates, such as a polysaccharide. In certain embodiments, the carbohydrate may comprise a carbohydrate derivative such as a sugar alcohol, including but not limited to mannitol, sorbitol, xylitol, erythritol, maltitol, and lactitol.

In some embodiments, synthetic nanocarriers can comprise one or more polymers. In some embodiments, the synthetic nanocarriers comprise one or more polymers that is a non-methoxy-terminated, pluronic polymer. In some embodiments, at least 1%, 2%, 3%, 4%, 5%, 10%, 15%, 20%, 25%, 30%, 35%, 40%, 45%, 50%, 55%, 60%, 65%, 70%, 75%, 80%, 85%, 90%, 95%, 97%, or 99% (weight/weight) of the polymers that make up the synthetic nanocarriers are non-methoxy-terminated, pluronic polymers. In some embodiments, all of the polymers that make up the synthetic nanocarriers are non-methoxy-terminated, pluronic polymers. In some embodiments, the synthetic nanocarriers comprise one or more polymers that is a non-methoxy-terminated polymer. In some embodiments, at least 1%, 2%, 3%, 4%, 5%, 10%, 15%, 20%, 25%, 30%, 35%, 40%, 45%, 50%, 55%, 60%, 65%, 70%, 75%, 80%, 85%, 90%, 95%, 97%, or 99% (weight/weight) of the polymers that make up the synthetic nanocarriers are non-methoxy-terminated polymers. In some embodiments, all of the polymers that make up the synthetic nanocarriers are non-methoxy-terminated polymers. In some embodiments, the synthetic nanocarriers comprise one or more polymers that do not comprise pluronic polymer. In some embodiments, at least 1%, 2%, 3%, 4%, 5%, 10%, 15%, 20%, 25%, 30%, 35%, 40%, 45%, 50%, 55%, 60%, 65%, 70%, 75%, 80%, 85%, 90%, 95%, 97%, or 99% (weight/weight) of the polymers that make up the synthetic nanocarriers do not comprise pluronic polymer. In some embodiments, all of the polymers that make up the synthetic nanocarriers do not comprise pluronic polymer. In some embodiments, such a polymer can be surrounded by a coating layer (e.g., liposome, lipid monolayer, micelle, etc.). In some embodiments, various elements of the synthetic nanocarriers can be attached with the polymer.

Immunosuppressants can be attached to the synthetic nanocarriers by any of a number of methods. Generally, the attaching can be a result of bonding between the immunosuppressants and the synthetic nanocarriers. This bonding can result in the immunosuppressants being attached to the surface of the synthetic nanocarriers and/or contained (encapsulated) within the synthetic nanocarriers. In some embodiments, however, the immunosuppressants are encapsulated by the synthetic nanocarriers as a result of the structure of the synthetic nanocarriers rather than bonding to the synthetic nanocarriers. In preferable embodiments, the synthetic nanocarrier comprises a polymer as provided herein, and the immunosuppressants are attached to the polymer.

When attaching occurs as a result of bonding between the immunosuppressants and synthetic nanocarriers, the attaching may occur via a coupling moiety. A coupling moiety can be any moiety through which an immunosuppressant is bonded to a synthetic nanocarrier. Such moieties include covalent bonds, such as an amide bond or ester bond, as well as separate molecules that bond (covalently or non-covalently) the immunosuppressant to the synthetic nanocarrier. Such molecules include linkers or polymers or a unit thereof. For example, the coupling moiety can comprise a charged polymer to which an immunosuppressant electrostatically binds. As another example, the coupling moiety can comprise a polymer or unit thereof to which it is covalently bonded.

In preferred embodiments, the synthetic nanocarriers comprise a polymer as provided herein. These synthetic nanocarriers can be completely polymeric or they can be a mix of polymers and other materials.

In some embodiments, the polymers of a synthetic nanocarrier associate to form a polymeric matrix. In some of these embodiments, a component, such as an immunosuppressant, can be covalently associated with one or more polymers of the polymeric matrix. In some embodiments, covalent association is mediated by a linker. In some embodiments, a component can be noncovalently associated with one or more polymers of the polymeric matrix. For example, in some embodiments, a component can be encapsulated within, surrounded by, and/or dispersed throughout a polymeric matrix. Alternatively or additionally, a component can be associated with one or more polymers of a polymeric matrix by hydrophobic interactions, charge interactions, van der Waals forces, etc. A wide variety of polymers and methods for forming polymeric matrices therefrom are known conventionally.

Polymers may be natural or unnatural (synthetic) polymers. Polymers may be homopolymers or copolymers comprising two or more monomers. In terms of sequence, copolymers may be random, block, or comprise a combination of random and block sequences. Typically, polymers in accordance with the present invention are organic polymers.

In some embodiments, the polymer comprises a polyester, polycarbonate, polyamide, or polyether, or unit thereof. In other embodiments, the polymer comprises poly(ethylene glycol) (PEG), polypropylene glycol, poly(lactic acid), poly(glycolic acid), poly(lactic-co-glycolic acid), or a polycaprolactone, or unit thereof. In some embodiments, it is preferred that the polymer is biodegradable. Therefore, in these embodiments, it is preferred that if the polymer comprises a polyether, such as poly(ethylene glycol) or polypropylene glycol or unit thereof, the polymer comprises a block-co-polymer of a polyether and a biodegradable polymer such that the polymer is biodegradable. In other embodiments, the polymer does not solely comprise a polyether or unit thereof, such as poly(ethylene glycol) or polypropylene glycol or unit thereof.

Other examples of polymers suitable for use in the present invention include, but are not limited to polyethylenes, polycarbonates (e.g. poly(1,3-dioxan-2one)), polyanhydrides (e.g. poly(sebacic anhydride)), polypropylfumerates, polyamides (e.g. polycaprolactam), polyacetals, polyethers, polyesters (e.g., polylactide, polyglycolide, polylactide-co-glycolide, polycaprolactone, polyhydroxyacid (e.g. poly(β-hydroxyalkanoate))), poly(orthoesters), polycyanoacrylates, polyvinyl alcohols, polyurethanes, polyphosphazenes, polyacrylates, polymethacrylates, polyureas, polystyrenes, and polyamines, polylysine, polylysine-PEG copolymers, and poly(ethyleneimine), poly(ethylene imine)-PEG copolymers.

In some embodiments, polymers in accordance with the present invention include polymers which have been approved for use in humans by the U.S. Food and Drug Administration (FDA) under 21 C.F.R. § 177.2600, including but not limited to polyesters (e.g., polylactic acid, poly(lactic-co-glycolic acid), polycaprolactone, polyvalerolactone, poly(1,3-dioxan-2one)); polyanhydrides (e.g., poly(sebacic anhydride)); polyethers (e.g., polyethylene glycol); polyurethanes; polymethacrylates; polyacrylates; and polycyanoacrylates.

In some embodiments, polymers can be hydrophilic. For example, polymers may comprise anionic groups (e.g., phosphate group, sulphate group, carboxylate group); cationic groups (e.g., quaternary amine group); or polar groups (e.g., hydroxyl group, thiol group, amine group). In some embodiments, a synthetic nanocarrier comprising a hydrophilic polymeric matrix generates a hydrophilic environment within the synthetic nanocarrier. In some embodiments, polymers can be hydrophobic. In some embodiments, a synthetic nanocarrier comprising a hydrophobic polymeric matrix generates a hydrophobic environment within the synthetic nanocarrier. Selection of the hydrophilicity or hydrophobicity of the polymer may have an impact on the nature of materials that are incorporated (e.g. attached) within the synthetic nanocarrier.

In some embodiments, polymers may be modified with one or more moieties and/or functional groups. A variety of moieties or functional groups can be used in accordance with the present invention. In some embodiments, polymers may be modified with polyethylene glycol (PEG), with a carbohydrate, and/or with acyclic polyacetals derived from polysaccharides (Papisov, 2001, ACS Symposium Series, 786:301). Certain embodiments may be made using the general teachings of U.S. Pat. No. 5,543,158 to Gref et al., or WO publication WO2009/051837 by Von Andrian et al.

In some embodiments, polymers may be modified with a lipid or fatty acid group. In some embodiments, a fatty acid group may be one or more of butyric, caproic, caprylic, capric, lauric, myristic, palmitic, stearic, arachidic, behenic, or lignoceric acid. In some embodiments, a fatty acid group may be one or more of palmitoleic, oleic, vaccenic, linoleic, alpha-linoleic, gamma-linoleic, arachidonic, gadoleic, arachidonic, eicosapentaenoic, docosahexaenoic, or erucic acid.

In some embodiments, polymers may be polyesters, including copolymers comprising lactic acid and glycolic acid units, such as poly(lactic acid-co-glycolic acid) and poly(lactide-co-glycolide), collectively referred to herein as "PLGA"; and homopolymers comprising glycolic acid units, referred to herein as "PGA," and lactic acid units, such as poly-L-lactic acid, poly-D-lactic acid, poly-D,L-lactic acid, poly-L-lactide, poly-D-lactide, and poly-D,L-lactide, collectively referred to herein as "PLA." In some embodiments, exemplary polyesters include, for example, polyhydroxyacids; PEG copolymers and copolymers of lactide and glycolide (e.g., PLA-PEG copolymers, PGA-PEG copolymers, PLGA-PEG copolymers, and derivatives thereof. In some embodiments, polyesters include, for example, poly(caprolactone), poly(caprolactone)-PEG copolymers, poly(L-lactide-co-L-lysine), poly(serine ester), poly(4-hydroxy-L-proline ester), poly[α-(4-aminobutyl)-L-glycolic acid], and derivatives thereof.

In some embodiments, a polymer may be PLGA. PLGA is a biocompatible and biodegradable co-polymer of lactic acid and glycolic acid, and various forms of PLGA are characterized by the ratio of lactic acid:glycolic acid. Lactic acid can be L-lactic acid, D-lactic acid, or D,L-lactic acid. The degradation rate of PLGA can be adjusted by altering the lactic acid:glycolic acid ratio. In some embodiments, PLGA to be used in accordance with the present invention is characterized by a lactic acid:glycolic acid ratio of approximately 85:15, approximately 75:25, approximately 60:40, approximately 50:50, approximately 40:60, approximately 25:75, or approximately 15:85.

In some embodiments, polymers may be one or more acrylic polymers. In certain embodiments, acrylic polymers include, for example, acrylic acid and methacrylic acid copolymers, methyl methacrylate copolymers, ethoxyethyl methacrylates, cyanoethyl methacrylate, aminoalkyl methacrylate copolymer, poly(acrylic acid), poly(methacrylic acid), methacrylic acid alkylamide copolymer, poly(methyl methacrylate), poly(methacrylic acid anhydride), methyl methacrylate, polymethacrylate, poly(methyl methacrylate) copolymer, polyacrylamide, aminoalkyl methacrylate copolymer, glycidyl methacrylate copolymers, polycyanoacrylates, and combinations comprising one or more of the foregoing polymers. The acrylic polymer may comprise fully-polymerized copolymers of acrylic and methacrylic acid esters with a low content of quaternary ammonium groups.

In some embodiments, polymers can be cationic polymers. In general, cationic polymers are able to condense and/or protect negatively charged strands of nucleic acids. Amine-containing polymers such as poly(lysine) (Zauner et al., 1998, Adv. Drug Del. Rev., 30:97; and Kabanov et al., 1995, Bioconjugate Chem., 6:7), poly(ethylene imine) (PEI; Boussif et al., 1995, Proc. Natl. Acad. Sci., USA, 1995, 92:7297), and poly(amidoamine) dendrimers (Kukowska-Latallo et al., 1996, Proc. Natl. Acad. Sci., USA, 93:4897; Tang et al., 1996, Bioconjugate Chem., 7:703; and Haensler et al., 1993, Bioconjugate Chem., 4:372) are positively-charged at physiological pH, form ion pairs with nucleic acids. In embodiments, the synthetic nanocarriers may not comprise (or may exclude) cationic polymers.

In some embodiments, polymers can be degradable polyesters bearing cationic side chains (Putnam et al., 1999, Macromolecules, 32:3658; Barrera et al., 1993, J. Am. Chem. Soc., 115:11010; Kwon et al., 1989, Macromolecules, 22:3250; Lim et al., 1999, J. Am. Chem. Soc., 121:5633; and Zhou et al., 1990, Macromolecules, 23:3399). Examples of these polyesters include poly(L-lactide-co-L-lysine) (Barrera et al., 1993, J. Am. Chem. Soc., 115:11010), poly(serine ester) (Zhou et al., 1990, Macromolecules, 23:3399), poly(4-hydroxy-L-proline ester) (Putnam et al., 1999, Macromolecules, 32:3658; and Lim et al., 1999, J. Am. Chem. Soc., 121:5633), and poly(4-hydroxy-L-proline ester) (Putnam et al., 1999, Macromolecules, 32:3658; and Lim et al., 1999, J. Am. Chem. Soc., 121:5633).

The properties of these and other polymers and methods for preparing them are well known in the art (see, for example, U.S. Pat. Nos. 6,123,727; 5,804,178; 5,770,417; 5,736,372; 5,716,404; 6,095,148; 5,837,752; 5,902,599; 5,696,175; 5,514,378; 5,512,600; 5,399,665; 5,019,379; 5,010,167; 4,806,621; 4,638,045; and 4,946,929; Wang et al., 2001, J. Am. Chem. Soc., 123:9480; Lim et al., 2001, J. Am. Chem. Soc., 123:2460; Langer, 2000, Acc. Chem. Res., 33:94; Langer, 1999, J. Control. Release, 62:7; and Uhrich et al., 1999, Chem. Rev., 99:3181). More generally, a variety of methods for synthesizing certain suitable polymers are described in Concise Encyclopedia of Polymer Science and Polymeric Amines and Ammonium Salts, Ed. by Goethals, Pergamon Press, 1980; Principles of Polymerization by Odian, John Wiley & Sons, Fourth Edition, 2004; Contemporary Polymer Chemistry by Allcock et al., Prentice-Hall, 1981; Deming et al., 1997, Nature, 390:386; and in U.S. Pat. Nos. 6,506,577, 6,632,922, 6,686,446, and 6,818,732.

In some embodiments, polymers can be linear or branched polymers. In some embodiments, polymers can be dendrimers. In some embodiments, polymers can be substantially cross-linked to one another. In some embodiments, polymers can be substantially free of cross-links. In some embodiments, polymers can be used in accordance with the present invention without undergoing a cross-linking step. It is further to be understood that the synthetic nanocarriers may comprise block copolymers, graft copolymers, blends, mixtures, and/or adducts of any of the foregoing and other polymers. Those skilled in the art will recognize that the polymers listed herein represent an exemplary, not comprehensive, list of polymers that can be of use in accordance with the present invention.

In some embodiments, synthetic nanocarriers do not comprise a polymeric component. In some embodiments, synthetic nanocarriers may comprise metal particles, quantum dots, ceramic particles, etc. In some embodiments, a non-polymeric synthetic nanocarrier is an aggregate of non-polymeric components, such as an aggregate of metal atoms (e.g., gold atoms).

Compositions according to the invention can comprise elements in combination with pharmaceutically acceptable excipients, such as preservatives, buffers, saline, or phosphate buffered saline. The compositions may be made using conventional pharmaceutical manufacturing and compounding techniques to arrive at useful dosage forms. In an embodiment, compositions, such as those comprising synthetic nanocarriers, are suspended in sterile saline solution for injection together with a preservative.

In embodiments, when preparing synthetic nanocarriers for use as carriers, methods for attaching components to the synthetic nanocarriers may be useful. If the component is a small molecule it may be of advantage to attach the component to a polymer prior to the assembly of the synthetic nanocarriers. In embodiments, it may also be an advantage to prepare the synthetic nanocarriers with surface groups that are used to attach the component to the synthetic nanocarrier through the use of these surface groups rather than attaching the component to a polymer and then using this polymer conjugate in the construction of synthetic nanocarriers.

In certain embodiments, the attaching can be with a covalent linker. In embodiments, components according to the invention can be covalently attached to the external surface via a 1,2,3-triazole linker formed by the 1,3-dipolar cycloaddition reaction of azido groups on the surface of the nanocarrier with a component containing an alkyne group or by the 1,3-dipolar cycloaddition reaction of alkynes on the surface of the nanocarrier with a component containing an azido group. Such cycloaddition reactions are preferably performed in the presence of a Cu(I) catalyst along with a suitable Cu(I)-ligand and a reducing agent to reduce Cu(II) compound to catalytic active Cu(I) compound. This Cu(I)-catalyzed azide-alkyne cycloaddition (CuAAC) can also be referred as the click reaction.

Additionally, the covalent attaching may comprise a covalent linker that comprises an amide linker, a disulfide linker, a thioether linker, a hydrazone linker, a hydrazide linker, an imine or oxime linker, an urea or thiourea linker, an amidine linker, an amine linker, and a sulfonamide linker.

An amide linker is formed via an amide bond between an amine on one component such as an immunosuppressant with the carboxylic acid group of a second component such as the nanocarrier. The amide bond in the linker can be made using any of the conventional amide bond forming reactions with suitably protected amino acids and activated carboxylic acid such N-hydroxysuccinimide-activated ester.

A disulfide linker is made via the formation of a disulfide (S—S) bond between two sulfur atoms of the form, for instance, of R1-S—S—R2. A disulfide bond can be formed by thiol exchange of a component containing thiol/mercaptan group (—SH) with another activated thiol group on a polymer or nanocarrier or a nanocarrier containing thiol/mercaptan groups with a component containing activated thiol group.

A triazole linker, specifically a 1,2,3-triazole of the form

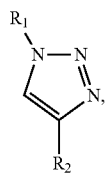

wherein R1 and R2 may be any chemical entities, is made by the 1,3-dipolar cycloaddition reaction of an azide attached to a first component such as the nanocarrier with a terminal alkyne attached to a second component such as the immunosuppressant. The 1,3-dipolar cycloaddition reaction is performed with or without a catalyst, preferably with Cu(I)-catalyst, which links the two components through a 1,2,3-triazole function. This chemistry is described in detail by Sharpless et al., Angew. Chem. Int. Ed. 41(14), 2596, (2002) and Meldal, et al, Chem. Rev., 2008, 108(8), 2952-3015 and is often referred to as a "click" reaction or CuAAC.

In embodiments, a polymer containing an azide or alkyne group, terminal to the polymer chain is prepared. This polymer is then used to prepare a synthetic nanocarrier in such a manner that a plurality of the alkyne or azide groups are positioned on the surface of that nanocarrier. Alternatively, the synthetic nanocarrier can be prepared by another route, and subsequently functionalized with alkyne or azide groups. The component is prepared with the presence of either an alkyne (if the polymer contains an azide) or an azide (if the polymer contains an alkyne) group. The component is then allowed to react with the nanocarrier via the 1,3-dipolar cycloaddition reaction with or without a catalyst which covalently attaches the component to the particle through the 1,4-disubstituted 1,2,3-triazole linker.

A thioether linker is made by the formation of a sulfur-carbon (thioether) bond in the form, for instance, of R1-S—R2. Thioether can be made by either alkylation of a thiol/mercaptan (—SH) group on one component with an alkylating group such as halide or epoxide on a second component. Thioether linkers can also be formed by Michael addition of a thiol/mercaptan group on one component to an electron-deficient alkene group on a second component containing a maleimide group or vinyl sulfone group as the Michael acceptor. In another way, thioether linkers can be prepared by the radical thiol-ene reaction of a thiol/mercaptan group on one component with an alkene group on a second component.

A hydrazone linker is made by the reaction of a hydrazide group on one component with an aldehyde/ketone group on the second component.

A hydrazide linker is formed by the reaction of a hydrazine group on one component with a carboxylic acid group on the second component. Such reaction is generally performed using chemistry similar to the formation of amide bond where the carboxylic acid is activated with an activating reagent.

An imine or oxime linker is formed by the reaction of an amine or N-alkoxyamine (or aminooxy) group on one component with an aldehyde or ketone group on the second component.

An urea or thiourea linker is prepared by the reaction of an amine group on one component with an isocyanate or thioisocyanate group on the second component.

An amidine linker is prepared by the reaction of an amine group on one component with an imidoester group on the second component.

An amine linker is made by the alkylation reaction of an amine group on one component with an alkylating group such as halide, epoxide, or sulfonate ester group on the second component. Alternatively, an amine linker can also be made by reductive amination of an amine group on one component with an aldehyde or ketone group on the second component with a suitable reducing reagent such as sodium cyanoborohydride or sodium triacetoxyborohydride.

A sulfonamide linker is made by the reaction of an amine group on one component with a sulfonyl halide (such as sulfonyl chloride) group on the second component.

A sulfone linker is made by Michael addition of a nucleophile to a vinyl sulfone. Either the vinyl sulfone or the nucleophile may be on the surface of the nanocarrier or attached to a component.

The component can also be conjugated to the nanocarrier via non-covalent conjugation methods. For example, a negative charged immunosuppressant can be conjugated to a positive charged nanocarrier through electrostatic adsorption. A component containing a metal ligand can also be conjugated to a nanocarrier containing a metal complex via a metal-ligand complex.

In embodiments, the component can be attached to a polymer, for example polylactic acid-block-polyethylene glycol, prior to the assembly of the synthetic nanocarrier or the synthetic nanocarrier can be formed with reactive or activatible groups on its surface. In the latter case, the component may be prepared with a group which is compatible with the attachment chemistry that is presented by the synthetic nanocarriers' surface. In other embodiments, a peptide component can be attached to VLPs or liposomes using a suitable linker. A linker is a compound or reagent that is capable of attaching two molecules together. In an embodiment, the linker can be a homobifuntional or heterobifunctional reagent as described in Hermanson 2008. For example, an VLP or liposome synthetic nanocarrier containing a carboxylic group on the surface can be treated with a homobifunctional linker, adipic dihydrazide (ADH), in the presence of EDC to form the corresponding synthetic nanocarrier with the ADH linker. The resulting ADH linked synthetic nanocarrier is then conjugated with a peptide component containing an acid group via the other end of the ADH linker on nanocarrier to produce the corresponding VLP or liposome peptide conjugate.

For detailed descriptions of available conjugation methods, see Hermanson G T "Bioconjugate Techniques", 2nd Edition Published by Academic Press, Inc., 2008. In addition to covalent attachment the component can be attached by adsorption to a pre-formed synthetic nanocarrier or it can be attached by encapsulation during the formation of the synthetic nanocarrier.

Any immunosuppressant as provided herein can be used according to the invention by being, for instance, used in nanocrystalline form, loaded into an ALZET® osmotic pump or by being attached to synthetic nanocarriers (i.e. synthetic nanocarrier-attached immunosuppressant).

Any immunosuppressant as provided herein can be used in the methods or compositions provided and can be, in some embodiments, attached to synthetic nanocarriers. Immunosuppressants include, but are not limited to, statins; mTOR inhibitors, such as rapamycin or a rapamycin analog;

TGF-β signaling agents; TGF-β receptor agonists; histone deacetylase (HDAC) inhibitors; corticosteroids; inhibitors of mitochondrial function, such as rotenone; P38 inhibitors; NF-κβ inhibitors; adenosine receptor agonists; prostaglandin E2 agonists; phosphodiesterase inhibitors, such as phosphodiesterase 4 inhibitor; proteasome inhibitors; kinase inhibitors; G-protein coupled receptor agonists; G-protein coupled receptor antagonists; glucocorticoids; retinoids; cytokine inhibitors; cytokine receptor inhibitors; cytokine receptor activators; peroxisome proliferator-activated receptor antagonists; peroxisome proliferator-activated receptor agonists; histone deacetylase inhibitors; calcineurin inhibitors; phosphatase inhibitors and oxidized ATPs. Immunosuppressants also include IDO, vitamin D3, cyclosporine A, aryl hydrocarbon receptor inhibitors, resveratrol, azathiopurine, 6-mercaptopurine, aspirin, niflumic acid, estriol, tripolide, interleukins (e.g., IL-1, IL-10), cyclosporine A, siRNAs targeting cytokines or cytokine receptors and the like.

Examples of statins include atorvastatin (LIPITOR®, TORVAST®), cerivastatin, fluvastatin (LESCOL®, LESCOL® XL), lovastatin (MEVACOR®, ALTOCOR®, ALTOPREV®), mevastatin (COMPACTIN®), pitavastatin (LIVALO®, PIAVA®), rosuvastatin (PRAVACHOL®, SELEKTINE®, LIPOSTAT®), rosuvastatin (CRESTOR®), and simvastatin (ZOCOR®, LIPEX®).

Examples of mTOR inhibitors include rapamycin and analogs thereof (e.g., CCL-779, RAD001, AP23573, C20-methallylrapamycin (C20-Marap), C16-(S)-butylsulfonamidorapamycin (C16-BSrap), C16-(S)-3-methylindolerapamycin (C16-iRap) (Bayle et al. Chemistry & Biology 2006, 13:99-107)), AZD8055, BEZ235 (NVP-BEZ235), chrysophanic acid (chrysophanol), deforolimus (MK-8669), everolimus (RAD0001), KU-0063794, PI-103, PP242, temsirolimus, and WYE-354 (available from Selleck, Houston, Tex., USA).

Examples of TGF-β signaling agents include TGF-β ligands (e.g., activin A, GDF1, GDF11, bone morphogenic proteins, nodal, TGF-βs) and their receptors (e.g., ACVR1B, ACVR1C, ACVR2A, ACVR2B, BMPR2, BMPR1A, BMPR1B, TGFβRI, TGFβRII), R-SMADS/co-SMADS (e.g., SMAD1, SMAD2, SMAD3, SMAD4, SMAD5, SMAD8), and ligand inhibitors (e.g, follistatin, noggin, chordin, DAN, lefty, LTBP1, THBS1, Decorin).

Examples of inhibitors of mitochondrial function include atractyloside (dipotassium salt), bongkrekic acid (triammonium salt), carbonyl cyanide m-chlorophenylhydrazone, carboxyatractyloside (e.g., from *Atractylis gummifera*), CGP-37157, (−)-Deguelin (e.g., from *Mundulea sericea*), F16, hexokinase II VDAC binding domain peptide, oligomycin, rotenone, Ru360, SFK1, and valinomycin (e.g., from *Streptomyces fulvissimus*) (EMD4Biosciences, USA).

Examples of P38 inhibitors include SB-203580 (4-(4-Fluorophenyl)-2-(4-methylsulfinylphenyl)-5-(4-pyridyl) 1H-imidazole), SB-239063 (trans-1-(4hydroxycyclohexyl)-4-(fluorophenyl)-5-(2-methoxy-pyrimidin-4-yl) imidazole), SB-220025 (5-(2-amino-4-pyrimidinyl)-4-(4-fluorophenyl)-1-(4-piperidinyl)imidazole)), and ARRY-797.

Examples of NF (e.g., NK-κβ inhibitors include IFRD1, 2-(1,8-naphthyridin-2-yl)-Phenol, 5-aminosalicylic acid, BAY 11-7082, BAY 11-7085, CAPE (Caffeic Acid Phenethylester), diethylmaleate, IKK-2 Inhibitor IV, IMD 0354, lactacystin, MG-132 [Z-Leu-Leu-Leu-CHO], NFκB Activation Inhibitor III, NF-κB Activation Inhibitor II, JSH-1, parthenolide, Phenylarsine Oxide (PAO), PPM-18, pyrrolidinedithiocarbamic acid ammonium salt, QNZ, RO 106-9920, rocaglamide, rocaglamide AL, rocaglamide C, rocaglamide I, rocaglamide J, rocaglaol, (R)-MG-132, sodium salicylate, triptolide (PG490), and wedelolactone.

Examples of adenosine receptor agonists include CGS-21680 and ATL-146e.

Examples of prostaglandin E2 agonists include E-Prostanoid 2 and E-Prostanoid 4.

Examples of phosphodiesterase inhibitors (non-selective and selective inhibitors) include caffeine, aminophylline, IBMX (3-isobutyl-1-methylxanthine), paraxanthine, pentoxifylline, theobromine, theophylline, methylated xanthines, vinpocetine, EHNA (erythro-9-(2-hydroxy-3-nonyl) adenine), anagrelide, enoximone (PERFAN™), milrinone, levosimendon, mesembrine, ibudilast, piclamilast, luteolin, drotaverine, roflumilast (DAXAS™, DALIRESP™), sildenafil (REVATION®, VIAGRA®), tadalafil (ADCIRCA®, CIALIS®), vardenafil (LEVITRA®, STAXYN®), udenafil, avanafil, icariin, 4-methylpiperazine, and pyrazolo pyrimidin-7-1.

Examples of proteasome inhibitors include bortezomib, disulfuram, epigallocatechin-3-gallate, and salinosporamide A.

Examples of kinase inhibitors include bevacizumab, BIBW 2992, cetuximab (ERBITUX®), imatinib (GLEEVEC®), trastuzumab (HERCEPTIN®), gefitinib (IRESSA®), ranibizumab (LUCENTIS®), pegaptanib, sorafenib, dasatinib, sunitinib, erlotinib, nilotinib, lapatinib, panitumumab, vandetanib, E7080, pazopanib, and mubritinib.

Examples of glucocorticoids include hydrocortisone (cortisol), cortisone acetate, prednisone, prednisolone, methylprednisolone, dexamethasone, betamethasone, triamcinolone, beclometasone, fludrocortisone acetate, deoxycorticosterone acetate (DOCA), and aldosterone.

Examples of retinoids include retinol, retinal, tretinoin (retinoic acid, RETIN-A®), isotretinoin (ACCUTANE®, AMNESTEEM®, CLARAVIS®, SOTRET®), alitretinoin (PANRETIN®), etretinate (TEGISON) and its metabolite acitretin (SORIATANE®), tazarotene (TAZORAC®, AVAGE®, ZORAC®), bexarotene (TARGRETIN®), and adapalene (DIFFERIN®).

Examples of cytokine inhibitors include IL1ra, IL1 receptor antagonist, IGFBP, TNF-BF, uromodulin, Alpha-2-Macroglobulin, Cyclosporin A, Pentamidine, and Pentoxifylline (PENTOPAK®, PENTOXIL®, TRENTAL®).

Examples of peroxisome proliferator-activated receptor antagonists include GW9662, PPARγ antagonist III, G335, and T0070907 (EMD4Biosciences, USA).

Examples of peroxisome proliferator-activated receptor agonists include pioglitazone, ciglitazone, clofibrate, GW1929, GW7647, L-165,041, LY 171883, PPARγ activator, Fmoc-Leu, troglitazone, and WY-14643 (EMD4Biosciences, USA).

Examples of histone deacetylase inhibitors include hydroxamic acids (or hydroxamates) such as trichostatin A, cyclic tetrapeptides (such as trapoxin B) and depsipeptides, benzamides, electrophilic ketones, aliphatic acid compounds such as phenylbutyrate and valproic acid, hydroxamic acids such as vorinostat (SAHA), belinostat (PXD101), LAQ824, and panobinostat (LBH589), benzamides such as entinostat (MS-275), CI994, and mocetinostat (MGCD0103), nicotinamide, derivatives of NAD, dihydrocoumarin, naphthopyranone, and 2-hydroxynaphaldehydes.

Examples of calcineurin inhibitors include cyclosporine, pimecrolimus, voclosporin, and tacrolimus.

Examples of phosphatase inhibitors include BN82002 hydrochloride, CP-91149, calyculin A, cantharidic acid, cantharidin, cypermethrin, ethyl-3,4-dephostatin, fostriecin sodium salt, MAZ51, methyl-3,4-dephostatin, NSC 95397, norcantharidin, okadaic acid ammonium salt from prorocentrum concavum, okadaic acid, okadaic acid potassium salt, okadaic acid sodium salt, phenylarsine oxide, various phosphatase inhibitor cocktails, protein phosphatase 1C, protein phosphatase 2A inhibitor protein, protein phosphatase 2A1, protein phosphatase 2A2, and sodium orthovanadate.

In some embodiments, the therapeutic macromolecules may be delivered in the form of the therapeutic macromolecule itself, or fragments or derivatives thereof. Therapeutic macromolecules can include therapeutic proteins and therapeutic polynucleotides. Therapeutic proteins include, but are not limited to, infusible therapeutic proteins, enzymes, enzyme cofactors, hormones, blood clotting factors, cytokines and interferons, growth factors, monoclonal antibodies, and polyclonal antibodies (e.g., that are administered to a subject as a replacement therapy), and proteins associated with Pompe's disease (e.g., acid glucosidase alfa, rhGAA (e.g., Myozyme and Lumizyme (Genzyme)). Therapeutic proteins also include proteins involved in the blood coagulation cascade. Therapeutic proteins include, but are not limited to, Factor VIII, Factor VII, Factor IX, Factor V, von Willebrand Factor, von Heldebrant Factor, tissue plasminogen activator, insulin, growth hormone, erythropoietin alfa, VEGF, thrombopoietin, lysozyme, antithrombin and the like. Therapeutic proteins also include adipokines, such as leptin and adiponectin. Other examples of therapeutic proteins are as described below and elsewhere herein.

Examples of therapeutic proteins used in enzyme replacement therapy of subjects having a lysosomal storage disorder include, but are not limited to, imiglucerase for the treatment of Gaucher's disease (e.g., CEREZYME™), α-galactosidase A (a-gal A) for the treatment of Fabry disease (e.g., agalsidase beta, FABRYZYME™), acid α-glucosidase (GAA) for the treatment of Pompe disease (e.g., acid glucosidase alfa, LUMIZYME™, MYOZYME™), and arylsulfatase B for the treatment of Mucopolysaccharidoses (e.g., laronidase, ALDURAZYME™, idursulfase, ELAPRASE™, arylsulfatase B, NAGLAZYME™)), pegloticase (KRYSTEXXA) and pegsiticase.

Examples of enzymes include oxidoreductases, transferases, hydrolases, lyases, isomerases, asparaginases, uricases, glycosidases, asparaginases, uricases, proteases, nucleases, collagenases, hyaluronidases, heparinases, heparanases, lysins, and ligases.

Therapeutic proteins may also include any enzyme, toxin, or other protein or peptide isolated or derived from a bacterial, fungal, or viral source.

Examples of hormones include Melatonin (N-acetyl-5-methoxytryptamine), Serotonin, Thyroxine (or tetraiodothyronine) (a thyroid hormone), Triiodothyronine (a thyroid hormone), Epinephrine (or adrenaline), Norepinephrine (or noradrenaline), Dopamine (or prolactin inhibiting hormone), Antimullerian hormone (or mullerian inhibiting factor or hormone), Adiponectin, Adrenocorticotropic hormone (or corticotropin), Angiotensinogen and angiotensin, Antidiuretic hormone (or vasopressin, arginine vasopressin), Atrial-natriuretic peptide (or atriopeptin), Calcitonin, Cholecystokinin, Corticotropin-releasing hormone, Erythropoietin, Follicle-stimulating hormone, Gastrin, Ghrelin, Glucagon, Glucagon-like peptide (GLP-1), GIP, Gonadotropin-releasing hormone, Growth hormone-releasing hormone, Human chorionic gonadotropin, Human placental lactogen, Growth hormone, Inhibin, Insulin, Insulin-like growth factor (or somatomedin), Leptin, Luteinizing hormone, Melanocyte stimulating hormone, Orexin, Oxytocin, Parathyroid hormone, Prolactin, Relaxin, Secretin, Somatostatin, Thrombopoietin, Thyroid-stimulating hormone (or thyrotropin), Thyrotropin-releasing hormone, Cortisol, Aldosterone, Testosterone, Dehydroepiandrosterone, Androstenedione, Dihydrotestosterone, Estradiol, Estrone, Estriol, Progesterone, Calcitriol (1,25-dihydroxyvitamin D3), Calcidiol (25-hydroxyvitamin D3), Prostaglandins, Leukotrienes, Prostacyclin, Thromboxane, Prolactin releasing hormone, Lipotropin, Brain natriuretic peptide, Neuropeptide Y, Histamine, Endothelin, Pancreatic polypeptide, Renin, and Enkephalin.

Examples of blood or blood coagulation factors include Factor I (fibrinogen), Factor II (prothrombin), tissue factor, Factor V (proaccelerin, labile factor), Factor VII (stable factor, proconvertin), Factor VIII (antihemophilic globulin), Factor IX (Christmas factor or plasma thromboplastin component), Factor X (Stuart-Prower factor), Factor Xa, Factor XI, Factor XII (Hageman factor), Factor XIII (fibrin-stabilizing factor), von Willebrand factor, prekallikrein (Fletcher factor), high-molecular weight kininogen (HMWK) (Fitzgerald factor), fibronectin, fibrin, thrombin, antithrombin III, heparin cofactor II, protein C, protein S, protein Z, protein Z-related protease inhibitot (ZPI), plasminogen, alpha 2-antiplasmin, tissue plasminogen activator (tPA), urokinase, plasminogen activator inhibitor-1 (PAI1), plasminogen activator inhibitor-2 (PAI2), cancer procoagulant, and epoetin alfa (Epogen, Procrit).

Examples of cytokines include lymphokines, interleukins, and chemokines, type 1 cytokines, such as IFN-γ, TGF-β, and type 2 cytokines, such as IL-4, IL-10, and IL-13.

Examples of growth factors include Adrenomedullin (AM), Angiopoietin (Ang), Autocrine motility factor, Bone morphogenetic proteins (BMPs), Brain-derived neurotrophic factor (BDNF), Epidermal growth factor (EGF), Erythropoietin (EPO), Fibroblast growth factor (FGF), Glial cell line-derived neurotrophic factor (GDNF), Granulocyte colony-stimulating factor (G-CSF), Granulocyte macrophage colony-stimulating factor (GM-CSF), Growth differentiation factor-9 (GDF9), Hepatocyte growth factor (HGF), Hepatoma-derived growth factor (HDGF), Insulin-like growth factor (IGF), Migration-stimulating factor, Myostatin (GDF-8), Nerve growth factor (NGF) and other neurotrophins, Platelet-derived growth factor (PDGF), Thrombopoietin (TPO), Transforming growth factor alpha (TGF-α), Transforming growth factor beta (TGF-β), Tumour_necrosis_factor-alpha (TNF-α), Vascular endothelial growth factor (VEGF), Wnt Signaling Pathway, placental growth factor (PlGF), (Foetal Bovine Somatotrophin) (FBS), IL-1, IL-2, IL-3, IL-4, IL-5, IL-6, and IL-7.

Examples of monoclonal antibodies include Abagovomab, Abciximab, Adalimumab, Adecatumumab, Afelimomab, Afutuzumab, Alacizumab pegol, ALD, Alemtuzumab, Altumomab pentetate, Anatumomab mafenatox, Anrukinzumab, Anti-thymocyte globin, Apolizumab, Arcitumomab, Aselizumab, Atlizumab (tocilizumab), Atorolimumab, Bapineuzumab, Basiliximab, Bavituximab, Bectumomab, Belimumab, Benralizumab, Bertilimumab, Besilesomab, Bevacizumab, Biciromab, Bivatuzumab mertansine, Blinatumomab, Brentuximab vedotin, Briakinumab, Canakinumab, Cantuzumab mertansine, Capromab pendetide, Catumaxomab, Cedelizumab, Certolizumab pegol, Cetuximab, Citatuzumab bogatox, Cixutumumab, Clenoliximab, Clivatuzumab tetraxetan, Conatumumab, Dacetuzumab, Daclizumab, Daratumumab, Denosumab, Detumomab, Dorlimomab aritox, Dorlixizumab, Ecromeximab, Eculizumab, Edobacomab, Edrecolomab, Efalizumab, Efungumab, Elotuzumab, Elsilimomab, Enlimomab pegol, Epitumomab cituxetan, Epratuzumab, Erlizumab, Ertumaxomab, Etaracizumab, Exbivirumab, Fanolesomab, Faralimomab, Farletuzumab, Felvizumab, Fezakinumab, Figitumumab, Fontolizumab, Foravirumab, Fresolimumab, Galiximab, Gantenerumab, Gavilimomab, Gemtuzumab ozogamicin, GC1008, Girentuximab, Glembatumumab vedotin, Golimumab, Gomiliximab, Ibalizumab, Ibritumomab tiuxetan, Igovomab, Imciromab, Infliximab, Intetumumab, Inolimomab, Inotuzumab ozogamicin, Ipilimumab, Iratumumab, Keliximab, Labetuzumab, Lebrikizumab, Lemalesomab, Lerdelimumab, Lexatumumab, Libivirumab, Lintuzumab, Lorvotuzumab mertansine, Lucatumumab, Lumiliximab, Mapatumumab, Maslimomab, Matuzumab, Mepolizumab, Metelimumab, Milatuzumab, Minretumomab, Mitumomab, Morolimumab, Motavizumab, Muromonab-CD3, Nacolomab tafenatox, Naptumomab estafenatox, Natalizumab, Nebacumab, Necitumumab, Nerelimomab, Nimotuzumab, Nofetumomab merpentan, Ocrelizumab, Odulimomab, Ofatumumab, Olaratumab, Omalizumab, Oportuzumab monatox, Oregovomab, Otelixizumab, Pagibaximab, Palivizumab, Panitumumab, Panobacumab, Pascolizumab, Pemtumomab, Pertuzumab, Pexelizumab, Pintumomab, Priliximab, Pritumumab, Rafivirumab, Ramucirumab, Ranibizumab, Raxibacumab, Regavirumab Reslizumab, Rilotumumab, Rituximab, Robatumumab, Rontalizumab, Rovelizumab, Ruplizumab, Satumomab pendetide, Sevirumab, Sibrotuzumab, Sifalimumab, Siltuximab, Siplizumab, Solanezumab, Sonepcizumab, Sontuzumab, Stamulumab, Sulesomab, Tacatuzumab tetraxetan, Tadocizumab, Talizumab, Tanezumab, Taplitumomab paptox, Tefibazumab, Telimomab aritox, Tenatumomab, Teneliximab, Teplizumab, Ticilimumab (tremelimumab), Tigatuzumab, Tocilizumab (atlizumab), Toralizumab, Tositumomab, Trastuzumab, Tremelimumab, Tucotuzumab celmoleukin, Tuvirumab, Urtoxazumab, Ustekinumab, Vapaliximab, Vedolizumab, Veltuzumab, Vepalimomab, Visilizumab, Volociximab, Votumumab, Zalutumumab, Zanolimumab, Ziralimumab, and Zolimomab aritox. Monoclonal antibodies further include anti-TNF-α antibodies.

Examples of infusion therapy or injectable therapeutic proteins include, for example, Tocilizumab (Roche/Actemra®), alpha-1 antitrypsin(Kamada/AAT), Hematide® (Affymax and Takeda, synthetic peptide), albinterferon alfa-2b (Novartis/Zalbin™), Rhucin® (Pharming Group, C1 inhibitor replacement therapy), tesamorelin (Theratechnologies/Egrifta, synthetic growth hormone-releasing factor), ocrelizumab (Genentech, Roche and Biogen), belimumab (GlaxoSmithKline/Benlysta®), pegloticase (Savient Pharmaceuticals/Krystexxa™), pegsiticase, taliglucerase alfa (Protalix/Uplyso), agalsidase alfa (Shire/Replagal®), velaglucerase alfa (Shire) and Keyhole Limpet Hemocyanin (KLH).

Additional therapeutic proteins include, for example, engineered proteins, such as Fc fusion proteins, bispecific antibodies, multi-specific antibodies, nanobodies, antigen-binding proteins, antibody fragments, and protein conjugates, such as antibody drug conjugates.

Therapeutic polynucleotides include, but are not limited to nucleic acid aptamers such as Pegaptanib (Macugen, a pegylated anti-VEGF aptamer), antisense therapeutics such as antisense poly- or oligonucleotides (e.g., antiviral drug Fomivirsen, or Mipomersen, an antisense therapeutic that targets the messenger RNA for apolipoprotein B for reduction of cholesterol level); small interfering RNAs (siRNAs) (e.g., dicer substrate siRNA molecules (DsiRNAs) which are 25-30 base pair asymmetric double-stranded RNAs that mediate RNAi with extremely high potency); or modified messenger RNAs (mmRNAs) such as those disclosed in US Patent application 2013/0115272 to de Fougerolles et al. and in Published US Patent application 2012/0251618 to Schrum et al.

Additional therapeutic macromolecules useful in accordance with aspects of this invention will be apparent to those of skill in the art, and the invention is not limited in this respect.

In some embodiments, a component, such as a therapeutic macromolecule or immunosuppressant, may be isolated. Isolated refers to the element being separated from its native environment and present in sufficient quantities to permit its identification or use. This means, for example, the element may be (i) selectively produced by expression cloning or (ii) purified as by chromatography or electrophoresis. Isolated elements may be, but need not be, substantially pure. Because an isolated element may be admixed with a pharmaceutically acceptable excipient in a pharmaceutical preparation, the element may comprise only a small percentage by weight of the preparation. The element is nonetheless isolated in that it has been separated from the substances with which it may be associated in living systems, i.e., isolated from other lipids or proteins. Any of the elements provided herein may be isolated and included in the compositions or used in the methods in isolated form.

D. Methods of making and using the methods and related Compositions

In embodiments wherein the recited immunosuppressant comprises an implantable osmotic pump, the immunosuppressant can be prepared using an ALZET® implantable osmotic pump containing a solution of an immunosuppressant. Such an implantable pump can be implanted subcutaneously for controlled release of an immunosuppressant into the local subcutaneous space for absorption of the compound by local capillaries resulting in systemic administration or intraperitoneally in the peritoneal cavity for controlled release of the immunosuppressant into hepatic portal circulation. The implantable pump can also be used via catheter for controlled intravenous delivery of the immunosuppressant into the venous or arterial circulation. They can be attached to a catheter for intravenous, intracerebral, or intra-arterial infusion or for targeted delivery, where the effects of a drug or test agent are localized in a particular tissue or organ. See, for example, S. M. Stepkowski et al., "Inhibition of host-versus-graft and graft-versus-host responses after small bowel transplantation in rats by rapamycin." Transplantation (1992) 53(–2-) δ 258-264. Other information regarding set up and use of ALZET® brand osmotic pumps, including an extensive literature database is available at alzet.com.

In embodiments wherein the recited immunosuppressant comprise bi-specific antibodies (BsAbs), the bi-specific antibodies can be prepared by genetic or biological methods such as fusion of two different hybridoma cell lines or by chemical methods such as cross linking two antibody molecules via suitable linkers according to methods known in the art. Several methods for producing BsAb have been developed. BsAb can be produced biologically by fusing two hybridoma lines, yielding quadromas that are capable of secreting BsAb. BsAb can also be generated genetically, and a variety of genetic techniques have been used to create bispecific molecules. A third method to create BsAb is by chemical means using a variety of homobifunctional and heterobifunctional chemical linkers (ref: Bispecific Antibodies, edited by Roland E. Kontermann, Springer, 2011). Further information on the formation of BsAbs can be found in the literature, including but not limited to M. Peipp et al., "Bispecific antibodies targeting cancer cells" Biochemical Society Transaction pp. 507-511 vol. 30 part 4 (2002). BsAbs can be administered to the patients by subcutaneous or intravenous injection similarly to the method of using monoclonal antibodies.

In certain embodiments, the recited immunosuppressant may be in the form of an implantable polymeric depot material. Implantable polymeric depot materials may be formulated and administered according to conventional particles found, for instance, in U.S. Pat. No. 5,702,716 to Dunn et al., entitled "Polymeric compositions useful as controlled release implants"; and U.S. Pat. No. 6,130,200 to Brodbeck et al., entitled "Gel composition and methods".

In embodiments, the immunosuppressant is attached to synthetic nanocarriers. Synthetic nanocarriers may be prepared using a wide variety of methods known in the art. For example, synthetic nanocarriers can be formed by methods such as nanoprecipitation, flow focusing fluidic channels, spray drying, single and double emulsion solvent evaporation, solvent extraction, phase separation, milling, microemulsion procedures, microfabrication, nanofabrication, sacrificial layers, simple and complex coacervation, and other methods well known to those of ordinary skill in the art. Alternatively or additionally, aqueous and organic solvent syntheses for monodisperse semiconductor, conductive, magnetic, organic, and other nanomaterials have been described (Pellegrino et al., 2005, Small, 1:48; Murray et al., 2000, Ann. Rev. Mat. Sci., 30:545; and Trindade et al., 2001, Chem. Mat., 13:3843). Additional methods have been described in the literature (see, e.g., Doubrow, Ed., "Microcapsules and Nanoparticles in Medicine and Pharmacy," CRC Press, Boca Raton, 1992; Mathiowitz et al., 1987, J. Control. Release, 5:13; Mathiowitz et al., 1987, Reactive Polymers, δ: 275; and Mathiowitz et al., 1988, J. Appl. Polymer Sci., 35:755; U.S. Pat. Nos. 5,578,325 and 6,007,845; P. Paolicelli et al., "Surface-modified PLGA-based Nanoparticles that can Efficiently Associate and Deliver Virus-like Particles" Nanomedicine. 5(6):843-853 (2010)).

Various materials may be encapsulated into synthetic nanocarriers as desirable using a variety of methods including but not limited to C. Astete et al., "Synthesis and characterization of PLGA nanoparticles" J. Biomater. Sci. Polymer Edn, Vol. 17, No. 3, pp. 247-289 (2006); K. Avgoustakis "Pegylated Poly(Lactide) and Poly(Lactide-Co-Glycolide) Nanoparticles: Preparation, Properties and Possible Applications in Drug Delivery" Current Drug Delivery 1:321-333 (2004); C. Reis et al., "Nanoencapsulation I. Methods for preparation of drug-loaded polymeric nanoparticles" Nanomedicine 2:8-21 (2006); P. Paolicelli et al., "Surface-modified PLGA-based Nanoparticles that can Efficiently Associate and Deliver Virus-like Particles" Nanomedicine. 5(6):843-853 (2010). Other methods suitable for encapsulating materials into synthetic nanocarriers may be used, including without limitation methods disclosed in U.S. Pat. No. 6,632,671 to Unger issued Oct. 14, 2003.

In certain embodiments, synthetic nanocarriers are prepared by a nanoprecipitation process or spray drying. Conditions used in preparing synthetic nanocarriers may be altered to yield particles of a desired size or property (e.g., hydrophobicity, hydrophilicity, external morphology, "stickiness," shape, etc.). The method of preparing the synthetic nanocarriers and the conditions (e.g., solvent, temperature, concentration, air flow rate, etc.) used may depend on the materials to be attached to the synthetic nanocarriers and/or the composition of the polymer matrix.

If synthetic nanocarriers prepared by any of the above methods have a size range outside of the desired range, such synthetic nanocarriers can be sized, for example, using a sieve.

Elements (i.e., components) of the synthetic nanocarriers may be attached to the overall synthetic nanocarrier, e.g., by one or more covalent bonds, or may be attached by means of one or more linkers. Additional methods of functionalizing synthetic nanocarriers may be adapted from Published US Patent Application 2006/0002852 to Saltzman et al., Published US Patent Application 2009/0028910 to DeSimone et al., or Published International Patent Application WO/2008/127532 A1 to Murthy et al.

Alternatively or additionally, synthetic nanocarriers can be attached to components directly or indirectly via non-covalent interactions. In non-covalent embodiments, the non-covalent coupling is mediated by non-covalent interactions including but not limited to charge interactions, affinity interactions, metal coordination, physical adsorption, host-guest interactions, hydrophobic interactions, TT stacking interactions, hydrogen bonding interactions, van der Waals interactions, magnetic interactions, electrostatic interactions, dipole-dipole interactions, and/or combinations thereof. Such couplings may be arranged to be on an external surface or an internal surface of a synthetic nanocarrier. In embodiments, encapsulation and/or absorption is a form of coupling. In embodiments, the synthetic nanocarriers can be combined with the immunosuppressant or therapeutic macromolecule by admixing in the same vehicle or delivery system.

Compositions provided may comprise inorganic or organic buffers (e.g., sodium or potassium salts of phosphate, carbonate, acetate, or citrate) and pH adjustment agents (e.g., hydrochloric acid, sodium or potassium hydroxide, salts of citrate or acetate, amino acids and their salts) antioxidants (e.g., ascorbic acid, alpha-tocopherol), surfactants (e.g., polysorbate 20, polysorbate 80, polyoxyethylene9-10 nonyl phenol, sodium desoxycholate), solution and/or cryo/lyo stabilizers (e.g., sucrose, lactose, mannitol, trehalose), osmotic adjustment agents (e.g., salts or sugars), antibacterial agents (e.g., benzoic acid, phenol, gentamicin), antifoaming agents (e.g., polydimethylsilozone), preservatives (e.g., thimerosal, 2-phenoxyethanol, EDTA), polymeric stabilizers and viscosity-adjustment agents (e.g., polyvinylpyrrolidone, poloxamer 488, carboxymethylcellulose) and co-solvents (e.g., glycerol, polyethylene glycol, ethanol).

Compositions according to the invention may comprise pharmaceutically acceptable excipients. The compositions may be made using conventional pharmaceutical manufacturing and compounding techniques to arrive at useful dosage forms, or may be made using specialized techniques (such as in the case of ALZET® pumps or bi-specific antibodies). Techniques suitable for use in practicing the present invention may be found in Handbook of Industrial Mixing: Science and Practice, Edited by Edward L. Paul, Victor A. Atiemo-Obeng, and Suzanne M. Kresta, 2004 John Wiley & Sons, Inc.; and Pharmaceutics: The Science of Dosage Form Design, 2nd Ed. Edited by M. E. Auten, 2001, Churchill Livingstone. In an embodiment, compositions are in a sterile saline solution for injection together with a preservative.

It is to be understood that the compositions of the invention can be made in any suitable manner, and the invention is in no way limited to compositions that can be produced using the methods described herein. Selection of an appropriate method of manufacture may require attention to the properties of the particular moieties being associated.

In some embodiments, immunosuppressants, therapeutic macromolecules, or compositions comprising such materials are manufactured under sterile conditions or are terminally sterilized. This can ensure that resulting materials or compositions are sterile and non-infectious, thus improving safety when compared to non-sterile materials or compositions. This provides a valuable safety measure, especially when subjects receiving recited materials or compositions have immune defects, are suffering from infection, and/or are susceptible to infection. In some embodiments, the materials or compositions may be lyophilized and stored in suspension or as lyophilized powder depending on the formulation strategy for extended periods without losing activity.

Administration according to the present invention may be by a variety of routes, including but not limited to subcutaneous, intravenous, intraperitoneal, intramuscular, transmucosal, transdermal, transcutaneous or intradermal routes. In a preferred embodiment, administration is via a subcutaneous route of administration. The compositions referred to herein may be manufactured and prepared for administration, in some embodiments concomitant administration, using conventional methods.

The compositions of the invention can be administered in effective amounts, such as the effective amounts described elsewhere herein. Doses of dosage forms may contain varying amounts of immunosuppressants or therapeutic macromolecules, according to the invention. The amount of immunosuppressants or therapeutic macromolecules present in the dosage forms can be varied according to the nature of the therapeutic macromolecules, immunosuppressants, the therapeutic benefit to be accomplished, and other such parameters. In embodiments, dose ranging studies can be conducted to establish optimal therapeutic amounts of immunosuppressants or therapeutic macromolecules to be present in any dosage forms. In embodiments, the immunosuppressants or therapeutic macromolecules are present in dosage forms in an amount effective to generate a tolerogenic immune response to the therapeutic macromolecules following administration to a subject. It may be possible to determine amounts of the immunosuppressants or therapeutic macromolecules effective to generate a tolerogenic immune response using conventional dose ranging studies and techniques in subjects. Administration of the immunosuppressants or therapeutic macromolecules may occur at a variety of frequencies.

Another aspect of the disclosure relates to kits. In some embodiments, the kit comprises an immunosuppressant dose that provides a pharmacodynamic effective-life. In some embodiments, the kit further comprises a dose of a therapeutic macromolecule. The immunosuppressant dose and the therapeutic macromolecule dose can be contained within separate containers or within the same container in the kit. In some embodiments, the container is a vial or an ampoule. In some embodiments, the therapeutic macromolecule dose and/or immunosuppressant dose are contained within a solution separate from the container(s), such that the dose of a therapeutic macromolecule and/or immunosuppressant dose may be added to the container at a subsequent time. In some embodiments, the therapeutic macromolecule dose and/or immunosuppressant dose are in lyophilized form each in a separate container or in the same container, such that they may be reconstituted at a subsequent time. In some embodiments, the kit further comprises instructions for reconstitution, mixing, administration, etc. In some embodiments, the instructions include a description of the methods described herein. Instructions can be in any suitable form, e.g., as a printed insert or a label. In some embodiments, the kit further comprises one or more syringes.

EXAMPLES

Example 1: Rapamycin-Containing Nanocarriers

Materials

Rapamycin was purchased from TSZ CHEM (185 Wilson Street, Framingham, Mass. 01702; Product Catalog #R1017). PLGA of approximately 25,000 Da was purchased from Lakeshore Biochemicals (756 Tom Martin Drive Birmingham, Ala. 35211). Product code 5050 DLG 2.5A. PLA-PEG-OMe block co-polymer with a methyl ether terminated PEG block of approximately 5,000 Da and PLA block of 48,000 Da was purchased from Lakeshore Biochemicals (756 Tom Martin Drive, Birmingham, Ala. 35211). Product Code 100 DL mPEG 5000 5CE. EMPROVE® Polyvinyl Alcohol 4-88, USP (85-89% hydrolyzed, viscosity of 3.4-4.6 mPa·s) was purchased from EMD Chemicals Inc. (480 South Democrat Road Gibbstown, N.J. 08027. Part Number 1.41354).

Method

Solutions were prepared as follows:

Solution 1: PLGA at 75 mg/mL, PLA-PEG-OMe at 25 mg/mL, and rapamycin at 12.5 mg/mL in methylene chloride. The solution was prepared by dissolving PLGA, PLA-PEG-OMe, and rapamycin in pure methylene chloride.

Solution 2: Polyvinyl alcohol at 50 mg/mL in 100 mM pH 8 phosphate buffer.

Solution 3: 70 mM phosphate buffer, pH 8.

An oil-in-water emulsion was created by mixing Solutions 1 (1 mL) and Solution 2 (3 mL) in a small glass pressure tube and sonicating at 30% amplitude for 60 seconds using a Branson Digital Sonifier 250. The emulsion was added to an open 50 mL beaker containing Solution 3 (30 mL) and stirred at room temperature for 2 hours to allow the dichloromethane to evaporate and the nanocarriers to form in suspension. A portion of the suspended nanocarriers was then washed by transferring the nanocarrier suspension to a centrifuge tube, spinning at 75,600 rcf for 40 minutes, removing the supernatant, and re-suspending the pellet in phosphate buffered saline. This washing procedure was repeated and then the pellet was re-suspended in PBS 1× to achieve a nanocarrier suspension having a nominal concentration of 10 mg/mL on a polymer basis. The suspension was stored frozen at −20° C. until use.

Nanocarrier size was determined by dynamic light scattering. The amount rapamycin in the nanocarrier was determined by HPLC analysis. The total dry-nanocarrier mass per mL of suspension was determined by a gravimetric method.

| Effective Diameter (nm) | Rapamycin Load (% w/w) |
|---|---|
| 218 | 9.9 |

Example 2: Polymeric Nanocarrier Containing Polymer-Rapamycin Conjugate (Prophetic)

Step 1: Preparation of PLGA-Rapamycin Conjugate:

PLGA polymer with acid end group (7525 DLG1A, acid number 0.46 mmol/g, Lakeshore Biomaterials; 5 g, 2.3 mmol, 1.0 eq) is dissolved in 30 mL of dichloromethane (DCM). N,N-Dicyclohexylcarbodimide (1.2 eq, 2.8 mmol, 0.57 g) is added followed by rapamycin (1.0 eq, 2.3 mmol, 2.1 g) and 4-dimethylaminopyridine (DMAP) (2.0 eq, 4.6 mmol, 0.56 g). The mixture is stirred at rt for 2 days. The mixture is then filtered to remove insoluble dicyclohexylurea. The filtrate is concentrated to ca. 10 mL in volume and added to 100 mL of isopropyl alcohol (IPA) to precipitate out the PLGA-rapamycin conjugate. The IPA layer is removed and the polymer is then washed with 50 mL of IPA and 50 mL of methyl t-butyl ether (MTBE). The polymer is then dried under vacuum at 35 C for 2 days to give PLGA-rapamycin as a white solid (ca. 6.5 g).

Step 2: Nanocarrier Containing PLGA-Rapamycin is Prepared According to the Procedure Described in Example 1 as Follows:

Solutions for nanocarrier formation are prepared as follows:

Solution 1: PLGA-rapamycin @100 mg/mL in methylene chloride. The solution is prepared by dissolving PLGA-rapamycin in pure methylene chloride. Solution 2: PLA-PEG @100 mg/mL in methylene chloride. The solution is prepared by dissolving PLA-PEG in pure methylene chloride. Solution 3: Polyvinyl alcohol @50 mg/mL in 100 mM pH 8 phosphate buffer.

A primary water-in-oil emulsion is prepared first. W1/O1 is prepared by combining solution 1 (0.75 mL), and solution 2 (0.25 mL) in a small pressure tube and sonicating at 50% amplitude for 40 seconds using a Branson Digital Sonifier 250. A secondary emulsion (W1/O1/W2) is then prepared by combining solution 3 (3.0 mL) with the primary W1/O1 emulsion, vortexing for 10 s, and sonicating at 30% amplitude for 60 seconds using the Branson Digital Sonifier 250. The W1/O1/W2 emulsion is added to a beaker containing 70 mM pH 8 phosphate buffer solution (30 mL) and stirred at room temperature for 2 hours to allow the methylene chloride to evaporate and for the nanocarriers to form. A portion of the nanocarriers is washed by transferring the nanocarrier suspension to a centrifuge tube and centrifuging at 75,600×g and 4° C. for 35 min, removing the supernatant, and re-suspending the pellet in phosphate buffered saline. The washing procedure is repeated, and the pellet is re-suspended in phosphate buffered saline for a final nanocarrier dispersion of about 10 mg/mL.

Example 3: Preparation of Gold Nanocarriers (AuNCs) Containing Rapamycin (Prophetic)

Step 1. Preparation of HS-PEG-Rapamycin:

A solution of PEG acid disulfide (1.0 eq), rapamycin (2.0-2.5 eq), DCC (2.5 eq) and DMAP (3.0 eq) in dry DMF is stirred at rt overnight. The insoluble dicyclohexylurea is removed by filtration and the filtrate is added to isopropyl alcohol (IPA) to precipitate out the PEG-disulfide-di-rapamycin ester and washed with IPA and dried. The polymer is then treated with tris(2-carboxyethyl)phosphine hydrochloride in DMF to reduce the PEG disulfide to thiol PEG rapamycin ester (HS-PEG-rapamycin). The resulting polymer is recovered by precipitation from IPA and dried as previously described and analyzed by H NMR and GPC.

Step 2. Formation of Gold NCs (AuNCs):

An aq. solution of 500 mL of 1 mM HAuCl4 is heated to reflux for 10 min with vigorous stirring in a 1 L round-bottom flask equipped with a condenser. A solution of 50 mL of 40 mM of trisodium citrate is then rapidly added to the stirring solution. The resulting deep wine red solution is kept at reflux for 25-30 min and the heat is withdrawn and the solution is cooled to room temperature. The solution is then filtered through a 0.8 μm membrane filter to give the AuNCs solution. The AuNCs are characterized using visible spectroscopy and transmission electron microscopy. The AuNCs are ca. 20 nm diameter capped by citrate with peak absorption at 520 nm.

Step 3. AuNCs Conjugate with HS-PEG-Rapamycin:

A solution of 150 μl of HS-PEG-rapamycin (10 μM in 10 mM pH 9.0 carbonate buffer) is added to 1 mL of 20 nm diameter citrate-capped gold nanocarriers (1.16 nM) to produce a molar ratio of thiol to gold of 2500:1. The mixture is stirred at room temperature under argon for 1 hour to allow complete exchange of thiol with citrate on the gold nanocarriers. The AuNCs with PEG-rapamycin on the surface is then purified by centrifuge at 12,000 g for 30 minutes. The supernatant is decanted and the pellet containing AuNC-S-PEG-rapamycin is then pellet washed with 1×PBS buffer. The purified Gold-PEG-rapamycin nanocarriers are then resuspend in suitable buffer for further analysis and bioassays.

Example 4: Effect of Encapsulated Rapamycin on the Initiation of Antibody Responses I. Measurement of IgG The level of IgG antibodies were measured generally as follows. Blocker Casein in PBS (Thermo Fisher, Catalog #37528) was used as diluent. 0.05% Tween-20 in PBS was used as wash buffer, prepared by adding 10 ml of Tween-20 ((Sigma, Catalog #P9416-100 mL) to 2 liters of a 10×PBS stock (PBS: OmniPur® 10×PBS Liquid Concentrate, 4L, EMD Chemicals, Catalog #6505) and 18 Liters of deionized water.

Keyhole Limpet Hemocyanin (KLH) at a stock concentration of 10 mg/ml or Ovalbumin (OVA) protein at a stock concentration of 5 mg/mL was used as a coating material. Both materials were diluted to 5 μg/ml was used as a working concentration. Each well of the assay plates was coated with 100 μl diluted KLH or OVA per well, plates were sealed with sealing film (VWR catalog #60941-120), and incubated overnight at 4° C. Costar 9017 96-well Flat bottom plates were used as assay plates (Costar 9017).

Low-binding polypropylene 96-well plate or tubes were used as set-up plates, in which samples were prepared before being transferred to the assay plate. The setup plates did not contain any antigen and, therefore, serum antibodies did not bind to the plate during the setup of the samples. Setup plates were used for sample preparation to minimize binding that might occur during preparation or pipetting of samples if an antigen-coated plate was used to prepare the samples. Before preparing samples in the setup plate, wells were covered with diluent to block any non-specific binding and the plate was sealed and incubated at 4° C. overnight.

Assay plates were washed three times with wash buffer, and wash buffer was completely aspirated out of the wells after the last wash. After washing, 300 μl diluent were added to each well of assay plate(s) to block non-specific binding and plates were incubated at least 2 hours at room temperature. Serum samples were diluted 1:40 in the appropriate well of the setup plate. Standards were used as positive controls. For KLH, a mouse anti-KLH IgG antibody was used at 1 μg/mL starting dilution, then diluted 3-fold across the plate. For OVA, a mouse anti-OVA IgG antibody was used at 0.5 μg/mL starting dilution, then diluted 3-fold across the plate.

Once all samples were prepared in the setup plate, the plate was sealed and stored at 4° C. until blocking of the assay plates was complete. Assay plates were washed three times with wash buffer, and wash buffer was completely aspirated after the last wash. After washing, 100 µL of diluent was added to Columns 2-12 of the assay plates. A pipet was used to transfer samples from the setup plate to the assay plate. Samples were mixed prior to transfer by pipetting 150 µl of diluted serum up and down 3 times. After mixing, 1500 of each sample was transferred from the setup plate and added to the respective assay plate.

Once the starting dilutions of each sample were transferred from the setup plate to the assay plate, serial dilutions were pipetted on the assay plate as follows: 50 µl of each serum sample was removed using a pipet and mixed with the 100 µl of diluent previously added. This step was repeated across the entire plate. After pipetting the dilution of the final column, 50 µl of fluid was removed from the wells in the final column and discarded, resulting in a final volume of 100 µl in every well of the assay plate. Once sample dilutions were prepared in the assay plates, the plates were incubated at room temperature for at least 2 hours.

After the incubation, plates were washed three times with wash buffer. Detection antibody (Goat anti-mouse anti-IgG, HRP conjugated) was diluted 1:1500 (0.33 µg/mL) in diluent and 100 µl of the diluted antibody was added to each well. Plates were incubated for 1 hour at room temperature and then washed five times with wash buffer and wash buffer was completely aspirated out of the wells after the last wash. After washing, detection substrate was added to the wells. Equal parts of substrate A and substrate B (BD Biosciences TMB Substrate Reagent Set, catalog #555214) were combined immediately before addition to the assay plates, and 100 µl of the mixed substrate solution were added to each well and incubated for 10 minutes in the dark. The reaction was stopped by adding 50 µl of stop solution (2N H2SO4) to each well after the 10 minute period. The optical density (OD) of the wells was assessed immediately after adding the stop solution on a plate reader at 450 nm with subtraction at 570 nm. Data analysis was performed using Molecular Device's software SoftMax Pro v 6.2.2. A four-parameter logistic curve-fit graph was prepared with the dilution on the x-axis (log scale) and the OD value on the y-axis (linear scale), and the half maximum value (EC50) for each sample was determined. The plate template at the top of the layout was adjusted to reflect the dilution of each sample (1 per row).

II. Preparation of Particulate Ovalbumin Protein (pOVA)

Materials

Chicken egg ovalbumin (OVA) was purchased from Worthington Biochemical Corporation (730 Vassar Avenue, Lakewood, N.J. 08701; Product code LS003054). Phosphate buffered saline (PBS) was purchased from Mediatech (9345 Discovery Boulevard, Manassas, Va. 20109; Product code 21-040-CV). Sodium hydroxide (NaOH, Product code 367176) and trifluoroacetic acid (TFA, Product code T62200) were purchased from Sigma-Aldrich Corp. (3050 Spruce Street, St. Louis, Mo. 63103).

Method

Solutions were prepared as follows:

Solution 1: OVA at 15 mg/mL in PBS. The solution was prepared by dissolving ovalbumin directly in PBS. Solution 2: NaOH at 1 M in water. The solution was prepared by dissolving NaOH directly in endotoxin-free water.

OVA was coacervated by repeatedly raising and lowering the pH of the ovalbumin solution. Solution 1 (10 mL) was added to a 20-mL glass vial containing a magnetic stir bar. While stirring, Solution 2 was added dropwise to the vial until the solution reached a pH of 12. TFA was then added dropwise to the vial until the solution reached a pH of 2. This raising and lowering of the pH was repeated three additional times. Solution 2 was then added dropwise to the vial until the solution reached a pH of 7.

The size of the coacervated OVA particles was then reduced by high pressure homogenization. The coacervated OVA suspension was loaded into a Microfluidics LV1 with G10Z interaction chamber and then homogenized using three passes at 20,000 psi. The resulting particulate OVA (pOVA) with size in the range of 190-240 nm was stored at −20 C.

III. In Vivo Testing of Encapsulated Rapamycin on the Initiation of Antibody Responses Groups of C57BL/6 animals (n=5) were left untreated and unimmunized (No immunization), untreated and immunized (No treatment) or treated with rapamycin-containing nanocarriers and immunized (Rapa-NCs) from Example 1 at days 0, 3 and 7. The immunizations consisted of injections of a particulate form of Ovalbumin (pOVA). The injections were in the hind limb subcutaneously. The dose of particles for each injection was the equivalent of 100 µg of rapamycin for a total of 300 µg after the three injections. Starting at day 14 untreated and treated animals (No treatment and Rapa-NCs) received biweekly immunizations (days 14, 28 and 42) with 10 µg of pOVA prepared as above injected in the front limbs (30 µl each) and 5014 of keyhole limpet hemocyanin (KLH, Sigma Aldrich) in the base tail (50 µl each flank). All animals were bled at the indicated days in FIG. 1 and the anti-OVA response was determined by ELISA.

The data demonstrate that encapsulated rapamycin effectively inhibited the anti-OVA response when injected 7 days prior to the administration of antigen, within the range of the pharmacodynamic effective-life as provided herein.

Figure 2:
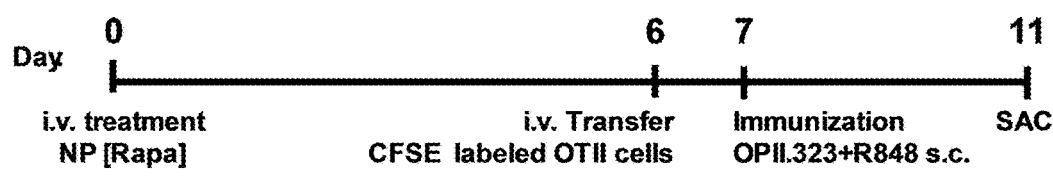
FIG. 2 shows a protocol and results from various rapamycin doses.
Figure 2:
Figure 2:
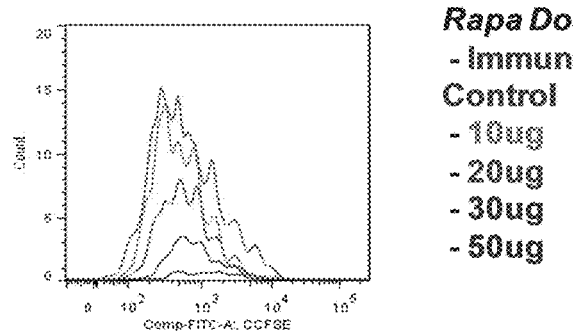

Example 5: Dose-Dependent Inhibition of T Cell Activation with Encapsulated Rapamycin In order to test the dose-dependency of rapamycin-mediated inhibition on T cell activation CD45.1+ animals (B6.SJL) were injected with encapsulated rapamycin (NP [Rapa], as disclosed in Example 1) intravenously at different doses (10 to 50 µg of Rapamycin and one PBS control). These animals share the same genetic background with C57BL/6 mice but express a different isoform of the CD45 molecule (CD45.1 instead of CD45.2). Six days later T cells isolated by magnetic cell sorting (MACS, Miltenyi) from the spleen and lymph nodes of OTII mouse strain that express CD45.2 and a transgenic TCR recognizing a peptide from chicken ovalbumin presented in the context of MHC CLII ($OVA_{323-339}$ or OPII.323) were adoptively transferred into the CD45.1+-treated animals. These cells were also labeled with CFSE (Invitrogen) to track their proliferation status. The next day (day 7) all animals were injected with an immunogenic dose of OPII.323 mixed with the TLR7/8 agonist R4848 subcutaneously in the hind limbs. At day 11 animals were sacrificed, the lymph nodes draining the site of injection (popliteal) were excised and the cells analyzed by flow cytometry to identify the transferred CD45.2+TCRb+ CD4+7AAD-T cells (antibodies from Biolegend). As shown in FIG. 2, injections of as low as 20 µg of Rapamycin have an inhibitory effect in the activation and the survival of these T cells even 6 days after the injection of the nanocarriers, again within the range of the pharmacodynamic effective-life as provided herein. Mounting rapamycin dosing yielded decreased cell numbers and proliferation.

Example 6: Immunosuppressant Using an Implantable Osmotic Pump and Evaluating its Tolerogenic Immune Responses In Vivo (Prophetic)

Step 1:

Rapamycin is dissolved in a vehicle consisting of dimethyl sulfoxide (DMSO)/polyethylene glycol 400 and loaded in ALZET® implantable osmotic pumps (0.2 mL in volume, Model 2001, Durect Corp., Cupertino, Calif.). The pumps are then implanted subcutaneously (s.c.) in the right lateral lower abdomen of the mouse according to ALZET® pump operating procedures. With the pumps, rapamycin is administered s.c. continuously for 2 days at dose of 2.5 mg/kg/day.

Step 2:

Groups of C57BL/6 animals (n=5) are left untreated and unimmunized (No immunization), untreated and immunized (No treatment) or treated with the above rapamycin loaded osmotic pump implanted subcutaneously in lateral lower abdomen of the mice and immunized at days 0, 3 and 7. The immunizations consist of injections of a particulate form of Ovalbumin (pOVA). With the pumps, rapamycin is administered s.c. continuously for 2 days at a dose of 2.5 mg/kg/day. The dose of rapamycin for each injection is the equivalent of 100 µg of Rapamycin for a total of 300 µg after the three injections. Starting at day 14 untreated and treated animals (No treatment and Rapamycin loaded pump) receive biweekly immunizations (days 14, 28 and 42) with 100 µg of a therapeutic protein such as acid glucosidase alfa, or tissue plasminogen activator, or erythropoietin alfa, or Dorlixizumab, or Rituximab injected in the front limbs. All animals are bled at days 40 and 54 and the anti-protein response is determined by ELISA. Rapamycin administered via the implanted osmotic pump are expected to effectively inhibit the anti-protein response when injected within the pharmacodynamic effective-life as provided herein, and these effects are expected to be apparent even after priming and two boosts with the proteins.

Example 7: Immunosuppressant Using an Implantable Osmotic Pump and Evaluating its Tolerogenic Immune Responses In Vivo (Prophetic)

Step 1:

A stock solution of rapamycin (Rapa) in N,N-dimethylacetamide (DMAC) (19 mg/ml) is stored at 4° C. and protected from exposure to light. To obtain appropriate Rapa concentrations based upon the weight of the rats, the stock solution is diluted in a mixture of 10% Tween-80, 20% DMAC, and 70% polyethylene glycol 400 (PEG400). Appropriately diluted Rapa is loaded into ALZET® brand implantable osmotic pumps (model 2002; Durect Corp., Cupertino, Calif.), which has been primed for 4-6 h by incubation in sterile saline at 37° C. Thereafter, the delivery cannula is inserted into the mouse's lumbar vein for intravenous delivery of rapamycin.

Step 2:

Groups of C57BL/6 animals (n=5) are left untreated and unimmunized (No immunization), untreated and immunized (No treatment) or treated with the above rapamycin loaded osmotic pump and immunized at days 0, 3 and 7. The immunizations consist of injections of a particulate form of Ovalbumin (pOVA). With the pumps, rapamycin is administered via intravenous infusion for 2 days at dose of 2.5 mg/kg/day. The dose of rapamycin for each infusion is the equivalent of 100 µg of Rapamycin for a total of 300 µg after the three infusions. Starting at day 14 untreated and treated animals (No treatment and Rapamycin loaded pump) receive biweekly immunizations (days 14, 28 and 42) with 50-100 µg of a therapeutic polynucleotide such as Pegaptanib, Mipomersen, a modified messenger RNAs (mmRNAs) such as those disclosed in US Patent application 2013/0115272 to de Fougerolles et al.

All animals are bled at days 40 and 54 and the anti-protein response is determined by ELISA. Rapamycin administered via the implanted osmotic pump is expected to effectively inhibit the anti-polynucleotide response when injected within the pharmacodynamic effective-life as provided herein, and these effects are expected to be apparent even after priming and two boosts with the polynucleotide.

Example 8: Bi-Specific Antibody Immunosuppressant Using Chemically Cross-Linked Anti-GITR Antibody and Anti-Idiotypic Antibody Against Inhibitory Factor VIII Antibody for Tolerance Induction to Factor-VIII Protein (Prophetic)

Step 1: Preparation of Bispectic Antibody

F(ab')$_2$ fragments of anti-GITR-antibodies such as epratuzumab and anti-idiotypic antibody against inhibitory Factor VIII antibody (prepared according to U.S. Pat. No. 8,071,094) are prepared using ImmunoPure F(ab')$_2$ Preparation Kit (Pierce) according to manufacturer's instructions. F(ab')$_2$ containing fractions are pooled and concentrated using a 10,000 MWCO centrifugal filter (Millipore). Each F(ab')$_2$ is reduced to F(ab)-thiol by adding 2-mercaptoethanol to a final concentration of 20 mM at 30° C. for 20-40 min. Samples are chilled on ice and then passed over chilled Sephadex G25 columns equilibrated in 50 mM sodium acetate/0.5 mM EDTA pH 5.3. Protein-containing fractions are pooled. The anti-GITR Fab-thiol is then maleimidated for 30 min in an ice bath by addition of ½ volume of pre-chilled 12 mM cross-linker, o-phenylenedimaleimide (o-PDM) (dissolved in DMF). Anti-GITR-maleimidated-Fab is then passed over a chilled Sephadex G25 column equilibrated in 50 mM sodium acetate/0.5 mM EDTA pH 5.3. Protein-containing fractions are pooled and immediately added to the anti-idiotypic antibody against inhibitory Factor VIII antibody-thiol-Fab in a 1:1 molar ratio. The reaction is placed under nitrogen and stirred gently for 15-20 h at 4° C. The pH is adjusted to pH 8.0 using 1 M Tris-HCl pH 8.0, followed by the addition of 2-mercaptoethanol to a final concentration of 20 mM. The reaction is incubated for 20-40 min at 30° C. and then alkylated by adding iodoacetamide to a final concentration of 25 mM. The mixture is then passed over a Superdex 200 column equilibrated in PBS pH 7.4, and fractions are collected. Individual fractions are run on 10% SDS-PAGE gels under non-reducing conditions and stained with Coomassie Brilliant Blue (Sigma) or Silver Snap II Kit (Pierce). Bispecific antibody (anti-GITR/anti-idiotypic antibody against inhibitory Factor VIII antibodies) are identified, pooled and stored for use as immunosuppressant (dose 10 µg/day).

Step 2. Tolerance Induction for Factor VIII

Groups of C57BL/6 animals (n=5) are left untreated and unimmunized (No immunization), untreated and immunized (No treatment) or treated with the above bispecific antibody at 10 μg/day and immunized at days 0, 3 and 7. The immunizations consist of injections of particulate Ovalbumin (pOVA). Starting at day 14 untreated and treated animals (No treatment and bispecific antibody treatment) receive biweekly immunizations (days 14, 28 and 42) with 150 IU/kg of a recombinant human antihaemophilic factor VIII (Factor-VIII).

All animals are bled at days 40 and 54 and the anti-protein response is determined by ELISA. Bispecific antibody (anti-GITR/anti-idiotypic antibody against inhibitory Factor VIII antibodies) is expected to effectively inhibit the anti-Factor VIII response when injected within the pharmacodynamic effective-life as provided herein, and these effects are expected to be apparent even after priming and two boosts with Factor VIII protein.

0000366, Poly (D,L-lactide-co-glycolide) 50:50 RESOMER® RG502H, PLGA-502H, code no. 260187, Poly (D,L-lactide-co-glycolide) 50:50 RESOMER® RG503, PLGA-503, code no. 0080765, Poly (D,L-lactide-co-glycolide) 50:50 RESOMER® RG506, PLGA-506, code no. 95051, Poly (D,L-lactide-co-glycolide) 50:50 RESOMER® RG755, PLGA-755, code no. 95037, (Boehringer Ingelheim Chemicals, Inc., Petersburg, Va.), and the following solvents or mixtures: glyceryl triacetate (Eastman Chemical Co., Kingsport, Term.), benzyl benzoate ("BB"), ethyl benzoate ("EB"), methyl benzoate ("MB"), triacetin ("TA"), and triethyl citrate ("TC") (Aldrich Chemical Co., St Louis, Mo.). When solvent combinations are used, for example 20% triacetin and 80% benzyl benzoate, the solvent mixture is directly added to the pre-weighed dry polymer. Typical polymer molecular weights are in the range of 14,400-39,700 ($M_w$) [6,400-12,200 ($M_n$)]. Representative gel vehicles are described in Table 1 below.

TABLE 1

Gel Vehicles

| Solvent/Poly | Solvent | Polymer | Amount Solvent | Amount Polymer | Gel Weight | Ratio |
|---|---|---|---|---|---|---|
| 50/50 | BB | PLGA-502 | 5 g | 5 g | 10 g | 1.0 50/50 |
| | TA/BB Mix | PLGA-502 | 5 g | 5 g | 10 g | 1.0 60/40 |
| | TA/BB Mix | PLGA-502 | 6 g | 4 g | 10 g | 1.5 70/30 |
| | TA/BB Mix | PLGA-502 | 7 g | 3 g | 10 g | 2.3 80/20 |
| | TA/BB Mix | PLGA-502 | 8 g | 2 g | 10 g | 4.0 50/50 |
| | EB | PLGA-502 | 5 g | 5 g | 10 g | 1.0 50/50 |
| | TA/EB Mix | PLGA-502 | 5 g | 5 g | 10 g | 1.0 50/50 |
| | BB | PLGA-502 | 25 g | 25 g | 50 g | 1.0 55/45 |
| | BB | PLGA-502 | 27.5 g | 22.5 g | 50 g | 1.2 50/50 |
| | BB | PLGA-502 | 50 g | 50 g | 100 g | 1.0 50/50 |
| | TA/BB Mix | PLGA-502 | 50 g | 50 g | 100 g | 1.0 50/50 |
| | BB | PLGA-502H | 5 g | 5 g | 10 g | 1.0 50/50 |
| | BB | PLGA-503 | 50 g | 50 g | 100 g | 1.0 |

Example 9: Immunosuppressant Using an Implantable Polymeric Depot Material and Evaluating its Tolerogenic Immune In Vivo (Prophetic)

Step 1: Gel Vehicle Preparation

A glass vessel is tared on a Mettler PJ3000 top loader balance. Poly (D,L-lactide-co-glycolide) 50:50 RESOMER® RG502 (PLGA-502) is weighed into the glass vessel. The glass vessel containing PLGA-502 is tared and the corresponding solvent (as set forth in Table 2) is added. Amounts expressed as percentages for various polymer/solvent combinations are set forth in Table 1 below. The polymer/solvent mixture is manually stirred with a stainless steel square-tip spatula, resulting in a sticky amber paste-like substance containing white polymer particles. The vessel containing the polymer/solvent mixture is sealed and placed in a temperature controlled incubator equilibrated to 39 C. The polymer/solvent mixture is removed from the incubator when it appeared to be a clear amber homogeneous gel. Incubation time intervals may range from 1 to 4 days, depending on solvent and polymer type and solvent and polymer ratios. Additional depot gel vehicles are prepared with the following polymers: Poly (D,L-lactide-co-glycolide) 50:50 RESOMER® L104, PLGA-L104, code no. 33007, Poly (D,L-lactide-co-glycolide) 50:50 RESOMER® RG206, PLGA-206, code no. 8815, Poly (D,L-lactide-co-glycolide) 50:50 RESOMER® RG502, PLGA-502, code

TABLE 2

Immunosuppressants atorvastatin
rapamycin
C16-(S)-butylsulfonamidorapamycin (C16-BSrap)
Temsirolimus
activin A
atractyloside (dipotassium salt)
2-(1,8-naphthyridin-2-yl)-Phenol,
E-Prostanoid 2
Theophylline
Bortezomib
imatinib (GLEEVEC ®)
methylprednisolone
tretinoin (retinoic acid, RETIN-A ®)
Cyclosporin A
pioglitazone
pimecrolimus
cantharidin Various immunosuppressants according to Table 2 above (10-20% w/w), are added to a specified clear amber depot gel vehicle and blended manually until the dry powder is wetted completely. Then, mixture is thoroughly blended by conventional mixing using a Caframo mechanical stirrer with an attached square-tip metal spatula. Final homogenous gel immunosuppressant implantable polymeric depot materials are transferred to 3, 10 or 30 cc disposable syringes for storage or dispensing.

Step 2: Evaluating Tolerogenic Immune Responses In Vivo

Groups of C57BL/6 animals (n=5) are left untreated and unimmunized (No immunization), untreated and immunized (No treatment) or treated with the above implantable polymeric depot material containing 100 μg of Rapamycin and immunized at days 0, 3 and 7. The immunizations consist of injections of particulate Ovalbumin (pOVA). The polymer depot-rapamycin is implanted in the hind limb. The dose of polymer depot-rapamycin is the equivalent of 100 μg of rapamycin for a total of 300 μg after three treatments. Starting at day 14 untreated and treated animals (No treatment and Rapa-depot) receive biweekly immunizations (days 14, 28 and 42) with 2 mg/kg of a therapeutic protein such as recombinant tissue plasminogen activator (rtPA) injected in the front limbs. All animals are bled at the indicated days and the anti-rtPA response is determined by ELISA. Gel-implant containing rapamycin is expected to effectively inhibit the anti-rtPA response when injected within the pharmacodynamic effective-life as provided herein, and these effects are expected to be apparent even after priming and two boosts with rtPA.

Example 10: Administration within the Pharmacodynamic Effective-Life of Rapamycin Attached to Synthetic Nanocarriers Materials Rapamycin was purchased from TSZ CHEM (185 Wilson Street, Framingham, Mass. 01702; Product Code R1017). PLGA with a lactide:glycolide ratio of 3:1 and an inherent viscosity of 0.69 dL/g was purchased from SurModics Pharmaceuticals (756 Tom Martin Drive, Birmingham, Ala. 35211; Product Code 7525 DLG 7A). PLA-PEG-OMe block co-polymer with a methyl ether terminated PEG block of approximately 5,000 Da and an overall inherent viscosity of 0.5 DL/g was purchased from Lakeshore Biochemicals (756 Tom Martin Drive, Birmingham, Ala. 35211; Product Code 100 DL mPEG 5000 5CE). EMPROVE® Polyvinyl Alcohol 4-88, USP (85-89% hydrolyzed, viscosity of 3.4-4.6 mPa·s) was purchased from EMD Chemicals Inc. (480 South Democrat Road Gibbstown, N.J. 08027. Product Code 1.41350).

Method

Solutions were prepared as follows:

Solution 1: PLGA at 75 mg/mL, PLA-PEG-OMe at 25 mg/mL, and rapamycin at 12.5 mg/mL in methylene chloride. The solution was prepared by dissolving PLGA, PLA-PEG-OMe, and rapamycin in pure methylene chloride. Solution 2: Polyvinyl alcohol @50 mg/mL in 100 mM pH 8 phosphate buffer.

An oil-in-water emulsion was used to prepare the nanocarriers. The O/W emulsion was prepared by combining Solution 1 (1.0 mL) and Solution 2 (3.0 mL) in a small pressure tube and sonicating at 30% amplitude for 60 seconds using a Branson Digital Sonifier 250. The O/W emulsion was added to a beaker containing 70 mM pH 8 phosphate buffer solution. Three identical emulsions were formed, and added to the same beaker with the first emulsion. These were then stirred at room temperature for 2 hours to allow the methylene chloride to evaporate and for the nanocarriers to form. A portion of the nanocarriers was washed by transferring the nanocarrier suspension to centrifuge tubes and centrifuging at 75,600×g and 4° C. for 35 minutes, removing the supernatant, and re-suspending the pellet in phosphate buffered saline. The washing procedure was repeated, and the pellet was re-suspended in phosphate buffered saline for a final nanocarrier dispersion of about 10 mg/mL. The washed nanocarrier solution was then filtered using 1.2 μm PES membrane syringe filters from Pall, part number 4656.

Nanocarrier size was determined by dynamic light scattering. The amount of rapamycin in the nanocarrier was determined by HPLC analysis. The total dry-nanocarrier mass per mL of suspension was determined by a gravimetric method.

| Effective Diameter (nm) | Rapamycin Content (% w/w) |
|---|---|
| 241 | 11.1 |

Figure 3:
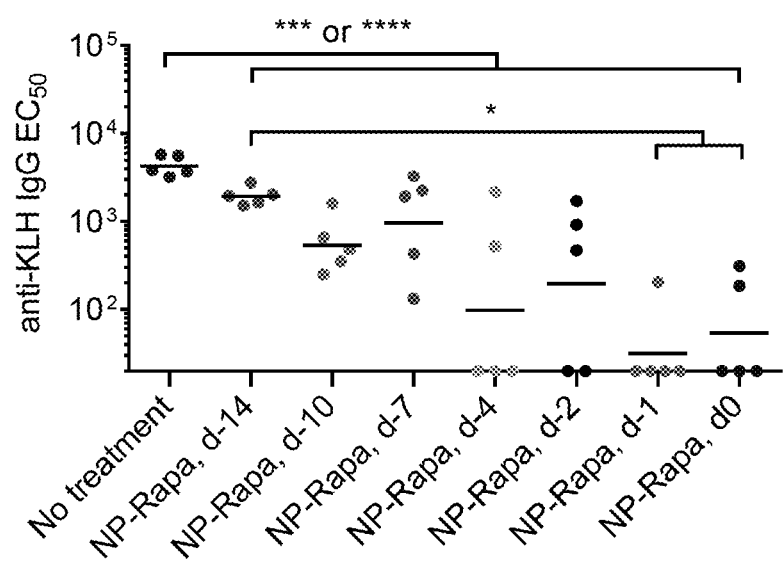
FIG. 3 demonstrates the effects of administration within the pharmacodynamic effective-life of synthetic nanocarriers attached to rapamycin.

Determination of the Immunosuppressive Window (Pharmacodynamic Effective-Life) of Rapamycin-Loaded Nanocarriers C57BL/6 age-matched (5-6 weeks) female were injected i.v. in the tail vain with 0.9 mg of the nanocarriers at various time points (as indicated in FIG. 3) from 14, 10, 7, 4, 2, and 1 day(s) previous (d-14, -10, -7, -4.-2 and -1, respectively) to the same day of injections of keyhole limpet hemocyanin (d0, 200 μg, KLH). All animals received weekly injections of KLH at days 0, 7 and 14 (200 μg, KLH). Antibody titers in the blood of these animals were determined at day 19.

The results in FIG. 3 show that injections of rapamycin-containing nanocarriers even 14 days previous to the immunization modify the antibody response to KLH and that tolerogenic nanocarriers provide a significant immunosuppressive window during which initiation of immune responses are dampened. The results demonstrate the ability to reduce antigen-specific immune responses by administering an immunosuppressant and antigen within the pharmacodynamic effective-life of the immunosuppressant.

Example 11: Antigen-Specific Tolerogenic Responses to Chicken Ovalbumin with Encapsulated Rapamycin NP[Rapa] Materials and Methods Materials Rapamycin was purchased from TSZ CHEM (185 Wilson Street, Framingham, Mass. 01702), product code R1017. PLGA with a lactide:glycolide ratio of 1:1 and an inherent viscosity of 0.24 dL/g was purchased from Lakeshore Biomaterials (756 Tom Martin Drive, Birmingham, Ala. 35211), product code 5050 DLG 2.5A. PLA-PEG-OMe block co-polymer with a methyl ether terminated PEG block of approximately 5,000 Da and an overall inherent viscosity of 0.50 DL/g was purchased from Lakeshore Biomaterials (756 Tom Martin Drive, Birmingham, Ala. 35211), product code 100 DL mPEG 5000 5CE. EMPROVE® Polyvinyl Alcohol 4-88, USP (85-89% hydrolyzed, viscosity of 3.4-4.6 mPa·s) was purchased from EMD Chemicals Inc. (480 South Democrat Road Gibbstown, N.J. 08027), product code 1.41350. Cellgro phosphate buffered saline 1× (PBS 1×) was purchased from Corning (9345 Discovery Blvd. Manassas, Va. 20109), product code 21-040-CV.

Method

Solutions were prepared as follows:

Solution 1: A polymer and rapamycin mixture was prepared by dissolving PLGA at 75 mg per 1 mL, PLA-PEG-Ome at 25 mg per 1 mL, and rapamycin as 12.5 mg per 1 mL in dichloromethane. Solution 2: Polyvinyl alcohol was prepared at 50 mg/mL in 100 mM pH 8 phosphate buffer.

An O/W emulsions was prepared by combining Solution 1 (1.0 mL) and Solution 2 (3.0 mL) in a small glass pressure tube and sonicating at 30% amplitude for 60 seconds using a Branson Digital Sonifier 250. The O/W emulsion was added to an open beaker containing 70 mM pH 8 phosphate buffer solution (60 mL). Three additional, identical O/W emulsions were prepared and added to the same beaker as the first. These were then stirred at room temperature for 2 hours to allow the dichloromethane to evaporate and for the nanocarriers to form. A portion of the nanocarriers was washed by transferring the nanocarrier suspension to centrifuge tubes and centrifuging at 75,600×g and 4° C. for 35 minutes, removing the supernatant, and re-suspending the pellet in PBS 1×. The wash procedure was repeated and then the pellet was re-suspended in PBS 1× to achieve a nanocarrier suspension having a nominal concentration of 10 mg/mL on a polymer basis. An identical formulation was prepared as above in a separate beaker, and combined with the first after the wash step. The mixed nanocarrier solution was then filtered using 1.2 µm PES membrane syringe filters from Pall part number 4656, and stored at −20° C.

Nanocarrier size was determined by dynamic light scattering. The amount of rapamycin in the nanocarrier was determined by HPLC analysis. The total dry-nanocarrier mass per mL of suspension was determined by a gravimetric method.

| Effective Diameter (nm) | Rapamycin Content (% w/w) |
| --- | --- |
| 220 | 11.85 |

NP[OVA] Materials and Methods
Materials

Ovalbumin protein, was purchased from Worthington Biochemical Corporation (730 Vassar Avenue, Lakewood, N.J. 08701), product code LS003054). PLGA with 54% lactide and 46% glycolide content and an inherent viscosity of 0.24 dL/g was purchased from Lakeshore Biomaterials (756 Tom Martin Drive, Birmingham, Ala. 35211), product code 5050 DLG 2.5A). PLA-PEG block co-polymer with a methyl ether terminated PEG block of approximately 5,000 Da and Mw of 28,000 Da, inherent viscosity of 0.38 dL/g was purchased from Lakeshore Biomaterials (756 Tom Martin Drive, Birmingham, Ala. 35211), product code 100 DL mPEG 5000 4CE. EMPROVE® Polyvinyl Alcohol 4-88, USP, 85-89% hydrolyzed, viscosity of 3.4-4.6 mPa·s, was purchased from EMD Chemicals Inc. (480 South Democrat Road Gibbstown, N.J. 08027), product code 1.41350.1001. Cellgro Phosphate-buffered saline 1× (PBS 1×) was purchased from Corning (9345 Discovery Blvd. Manassas, Va. 20109), product code 21-040-CV.
Method Solutions were prepared as follows:

Solution 1: Ovalbumin protein @50 mg/mL was prepared in 10 mM phosphate buffer pH 8 with 10% by weight sucrose. Solution 2: PLGA was prepared by dissolving PLGA at 100 mg per 1 mL of dichloromethane in the chemical fume hood. Solution 3: PLA-PEG-OMe was prepared by dissolving PLA-PEG-OMe at 100 mg per 1 mL of dichloromethane in the chemical fume hood.

Solution 4: Polyvinyl alcohol @65 mg/mL in 100 mM phosphate buffer, pH 8.

A primary (W1/O) emulsion was first created by mixing Solutions 1 through 3. Solution 1 (0.2 mL), Solution 2 (0.75 mL), and Solution 3 (0.25 mL) were combined in a small glass pressure tube which was pre-chilled >4 minutes in an ice water bath, and sonicated at 50% amplitude for 40 seconds over an ice bath using a Branson Digital Sonifier 250. A secondary (W1/O/W2) emulsion was then formed by adding Solution 4 (3 mL) to the primary emulsion, vortex mixing to create a milky dispersion, and then sonicating at 30% amplitude for 60 seconds over an ice bath using the Branson Digital Sonifier 250. The secondary emulsion was added to an open 50 mL beaker containing PBS 1× (30 mL). A second identical double emulsion formulation was prepared as described above, and added to the same 50 mL beaker as the first. The two preparations were stirred at room temperature for 2 hours to allow the dichloromethane to evaporate and the nanocarriers to form in suspension. A portion of the suspended nanocarriers was washed by transferring the nanocarrier suspension to a centrifuge tube, spinning at 75,600 rcf for 50 minutes, removing the supernatant, and re-suspending the pellet in PBS 1×. This washing procedure was repeated and then the pellet was re-suspended in PBS 1× to achieve a nanocarrier suspension having a nominal concentration of 10 mg/mL on a polymer basis. The suspension was stored frozen at −20 C until use.

| Effective Diameter (nm) | Ovalbumin Content (% w/w) |
| --- | --- |
| 164 | 5.81 |

NP[GSK1059615] Materials and Methods
Materials

GSK1059615 was purchased from MedChem Express (11 Deer Park Drive, Suite 102D Monmouth Junction, N.J. 08852), product code HY-12036. PLGA with a lactide:glycolide ratio of 1:1 and an inherent viscosity of 0.24 dL/g was purchased from Lakeshore Biomaterials (756 Tom Martin Drive, Birmingham, Ala. 35211), product code 5050 DLG 2.5A. PLA-PEG-OMe block co-polymer with a methyl ether terminated PEG block of approximately 5,000 Da and an overall inherent viscosity of 0.26 DL/g was purchased from Lakeshore Biomaterials (756 Tom Martin Drive, Birmingham, Ala. 35211; Product Code 100 DL mPEG 5000 5K-E). Cellgro phosphate buffered saline 1× pH 7.4 (PBS 1×) was purchased from Corning (9345 Discovery Blvd. Manassas, Va. 20109), product code 21-040-CV.
Method Solutions were prepared as follows:

Solution 1: PLGA (125 mg), and PLA-PEG-OMe (125 mg), were dissolved in 10 mL of acetone. Solution 2: GSK1059615 was prepared at 10 mg in 1 mL of N-methyl-2-pyrrolidinone (NMP).

Nanocarriers were prepared by combining Solution 1 (4 mL) and Solution 2 (0.25 mL) in a small glass pressure tube and adding the mixture drop wise to a 250 mL round bottom flask containing 20 mL of ultra-pure water under stirring. The flask was mounted onto a rotary evaporation device, and the acetone was removed under reduced pressure. A portion of the nanocarriers was washed by transferring the nanocarrier suspension to centrifuge tubes and centrifuging at 75,600 rcf and 4° C. for 50 minutes, removing the supernatant, and re-suspending the pellet in PBS 1×. The washing procedure was repeated, and the pellet was re-suspended in PBS 1× to achieve a nanocarrier suspension having a nominal concentration of 10 mg/mL on a polymer basis. The washed nanocarrier solution was then filtered using 1.2 µm PES membrane syringe filters from Pall, part number 4656. An identical nanocarrier solution was prepared as above, and pooled with the first after the filtration step. The homogenous suspension was stored frozen at −20° C.

Nanocarrier size was determined by dynamic light scattering. The amount of GSK1059615 in the nanocarrier was determined by UV absorption at 351 nm. The total dry-nanocarrier mass per mL of suspension was determined by a gravimetric method.

| Effective Diameter (nm) | GSK1059615 Content (% w/w) |
|---|---|
| 143 | 1.02 |

Figure 4:
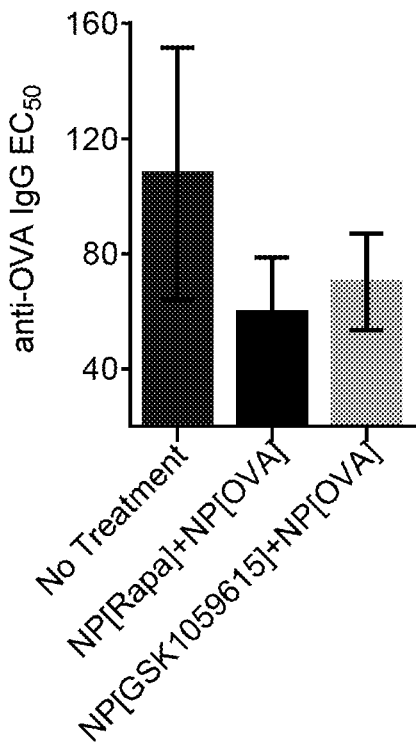
FIG. 4 demonstrates the effects of synthetic nanocarriers attached to rapamycin or nanocarriers attached to GSK1059615 administered concomitantly with encapsulated protein.

C57BL/6 age-matched (5-6 weeks) female mice were injected i.v. in the tail vein on days −21 and −14 with saline (No Treatment), 1.1 mg of whole Ovalbumin-loaded nanocarriers (NP[OVA]) combined to either 1.2 mg of rapamycin-containing nanocarriers (NP[Rapa]) or 8 mg of GSK1059615-containing nanocarriers (NP[GSK1059615]). At day 0 all animals were injected s.c. in the hind limbs with 25 µg of particulate OVA (pOVA) admixed to 2 µg of CpG followed by injections of just 25 µg pOVA on days 7 and 14. Antibody titers were measured on day 21. In absence of any treatment, the animals developed a robust immune response against OVA that can be measured by the anti-OVA IgG antibody titers. The antibody titers at day 21 shown in FIG. 4 demonstrate that 2 doses of synthetic tolerogenic nanocarriers administered concomitantly with encapsulated OVA in the same solution (NP[OVA]+NP[Rapa] or NP[GSK1059615]) were effective in reducing antibody formation to OVA even after 1 injection of OVA+CpG and 2 injections of OVA alone. These results show that encapsulated immunosuppressants (such as rapamycin and GSK1059615) when concomitantly delivered with a protein can prevent antibody formation to that protein.

Example 12: Administration Pharmacodynamic Effective Life Using Synthetic Nanocarriers (Prophetic)

A pilot trial is performed on non-human primate subjects using soluble Factor VIII and the synthetic nanocarriers of Example 1. 50 non-human primate subjects are randomly assigned to 5 arms: placebo, and then four dose levels of synthetic nanocarriers chosen for dose ranging. The dose ranging is to establish a pharmacodynamic effective-life ranging from 20 hours to 1 month, with a preferred pharmacodynamic effective-life target of one day. On day zero, the subjects in each active arm all are administered the dose of synthetic nanocarriers subcutaneously, and within 24 hours of the synthetic nanocarrier dose get an infusion of a standard infusion dose of Factor VIII. Two weeks later, each animal is challenged with a standard dose of soluble Factor VIII, and the level of anti-Factor VIII IgG antibodies is measured using standard ELISA techniques. The lowest dose of synthetic nanocarriers from among the four active arms that shows significant reduction in anti-Factor VIII antibodies is selected as the test dose.

The test dose of synthetic nanocarriers is then allometrically scaled for administration to human subjects, and is used in a human clinical trial to determine a range of administration dose levels of synthetic nanocarriers used with standard doses of soluble Factor VIII. Administration doses of synthetic nanocarriers and Factor VIII are then made available for regular clinical practice.

Example 13: Administration Pharmacodynamic Effective Life Using Synthetic Osmotic Pumps (Prophetic)

A pilot trial is performed on non-human primate subjects using soluble Factor VIII and osmotic pumps (prepared generally according to Example 6, but substituting GSK1059615 for the rapamycin of Example 6). 50 non-human primate subjects are randomly assigned to 5 arms: placebo, and then four dose levels of GSK1059615 delivered by osmotic pump and chosen for dose ranging. The dose ranging is to establish a pharmacodynamic effective-life ranging from 20 hours to 1 month, with a preferred pharmacodynamic effective-life target of one day. On day zero, the subjects in each active arm all are administered the dose of synthetic nanocarriers subcutaneously, and within 24 hours of the synthetic nanocarrier dose get an infusion of a standard infusion dose of Factor VIII. Two weeks later, each animal is challenged with a standard dose of soluble Factor VIII, and the level of anti-Factor VIII IgG antibodies is measured using standard ELISA techniques. The lowest dose of GSK1059615 delivered by osmotic pump from among the four active arms that shows significant reduction in anti-Factor VIII antibodies is selected as the test dose.

The test dose of GSK1059615 delivered by osmotic pump is then allometrically scaled for administration to human subjects, and is used in a human clinical trial to determine a range of administration dose levels of GSK1059615 delivered by osmotic pump used with standard doses of soluble Factor VIII. Administration doses of GSK1059615 delivered by osmotic pump and Factor VIII are then made available for regular clinical practice.

Example 14: Administration Pharmacodynamic Effective Life Using Therapeutic Polynucleotides (Prophetic)

A pilot trial is performed on non-human primate subjects using mmRNA encoding for asparaginase (made generally according to prepared according to US Patent application 2013/0115272 to de Fougerolles et al. ("mmRNA")) and the synthetic nanocarriers of Example 1. 50 non-human primate subjects are randomly assigned to 5 arms: placebo, and then four doses of synthetic nanocarriers chosen for dose ranging. The dose ranging is to establish a pharmacodynamic effective-life ranging from 20 hours to 1 month, with a preferred pharmacodynamic effective-life target of one day. On day zero, the subjects in each active arm all are administered the dose of synthetic nanocarriers subcutaneously, and within 24 hours of the synthetic nanocarrier dose get an infusion of a standard infusion dose of Factor VIII. Two weeks later, each animal is challenged with a standard dose of mmRNA, and the level of anti-mmRNA antibodies is measured using standard ELISA techniques. The lowest dose of synthetic nanocarriers from among the four active arms that shows significant reduction in anti-mmRNA antibodies is selected as the test dose.

The test dose of synthetic nanocarriers is then allometrically scaled for administration to human subjects, and is used in a human clinical trial to determine a range of administration dose of synthetic nanocarriers used with standard dose levels of mmRNA. Administration doses of synthetic nanocarriers and mmRNA are then made available for regular clinical practice.

Example 15: Administration Pharmacodynamic Effective Life Using Nanocrystalline Immunosuppressants (Prophetic)

A pilot trial is performed on non-human primate subjects using soluble Factor VIII and the synthetic nanocarriers of Example 1. 50 non-human primate subjects are randomly assigned to 5 arms: placebo, and then four dose levels of nanocrystalline rapamycin chosen for dose ranging. The dose ranging is to establish a pharmacodynamic effective-life ranging from 20 hours to 1 month, with a preferred pharmacodynamic effective-life target of one day. On day zero, the subjects in each active arm all are administered the dose of nanocrystalline rapamycin subcutaneously, and within 24 hours of the nanocrystalline rapamycin dose get an infusion of a standard infusion dose of Factor VIII. Two weeks later, each animal is challenged with a standard dose of soluble Factor VIII, and the level of anti-Factor VIII IgG antibodies is measured using standard ELISA techniques. The lowest dose of nanocrystalline rapamycin from among the four active arms that shows significant reduction in anti-Factor VIII antibodies is selected as the test dose.

The test dose of nanocrystalline rapamycin is then allometrically scaled for administration to human subjects, and is used in a human clinical trial to determine a range of administration dose levels of nanocrystalline rapamycin used with standard doses of soluble Factor VIII. Administration doses of nanocrystalline rapamycin and Factor VIII are then made available for regular clinical practice.

Example 16: Administration Pharmacodynamic Effective Life Using Nanocrystalline Immunosuppressants (Prophetic)

A pilot trial is performed on non-human primate subjects using mmRNA encoding for asparaginase (made generally according to prepared according to US Patent application 2013/0115272 to de Fougerolles et al. ("mmRNA")) and nanocrystalline rapamycin. 50 non-human primate subjects are randomly assigned to 5 arms: placebo, and then four doses of nanocrystalline rapamycin chosen for dose ranging. The dose ranging is to establish a pharmacodynamic effective-life ranging from 20 hours to 1 month, with a preferred pharmacodynamic effective-life target of one day. On day zero, the subjects in each active arm all are administered the dose of nanocrystalline rapamycin subcutaneously, and within 24 hours of the nanocrystalline rapamycin dose get an infusion of a standard infusion dose of Factor VIII. Two weeks later, each animal is challenged with a standard dose of mmRNA, and the level of anti-mmRNA antibodies is measured using standard ELISA techniques. The lowest dose of nanocrystalline rapamycin from among the four active arms that shows significant reduction in anti-mmRNA antibodies is selected as the test dose.

The test dose of nanocrystalline rapamycin is then allometrically scaled for administration to human subjects, and is used in a human clinical trial to determine a range of administration dose of nanocrystalline rapamycin used with standard dose levels of mmRNA. Administration doses of nanocrystalline rapamycin and mmRNA are then made available for regular clinical practice.

What is claimed is:

1. A method comprising:

administering an immunosuppressant to a subject in a first class of subjects at an administration dose that provides an administration pharmacodynamic effective-life, with respect to a therapeutic macromolecule, the duration of which pharmacodynamic effective-life ranges from a minimum of 20 hours to a maximum of 1 month; and administering the therapeutic macromolecule to the subject within the duration of the administration pharmacodynamic effective-life of the immunosuppressant;

wherein the therapeutic macromolecule and immunosuppressant are not attached to one another, and the therapeutic macromolecule is not attached to a synthetic nanocarrier.

2. The method of claim 1, wherein the method further comprises:

determining the administration dose of the immunosuppressant based on a test dose of the immunosuppressant;

wherein the test dose possesses a test pharmacodynamic effective-life with respect to the therapeutic macromolecule the duration of which pharmacodynamic effective-life ranges from a minimum of 20 hours to a maximum of 1 month in a second class of subjects.

3. The method of claim 1, wherein the immunosuppressant comprises synthetic nanocarriers that comprise a synthetic nanocarrier-attached immunosuppressant, implantable osmotic pumps, bi-specific antibodies, or implantable polymeric depot materials.

4. The method of claim 1, wherein the immunosuppressant comprises a synthetic nanocarrier-attached immunosuppressant.

5. The method of claim 1, wherein the synthetic nanocarrier comprises lipid nanoparticles, polymeric nanoparticles, metallic nanoparticles, surfactant-based emulsions, dendrimers, buckyballs, nanowires, virus-like particles, protein particles, or nanoparticles that comprise a combination of nanomaterials, optionally, wherein such nanoparticles are lipid-polymer nanoparticles.

6. The method of claim 1, wherein the immunosuppressant comprises statins; mTOR inhibitors; TGF-β signaling agents; TGF-β receptor agonists; histone deacetylase inhibitors; corticosteroids; inhibitors of mitochondrial function; P38 inhibitors; NF-κβ inhibitors, Dexamethasone; TCPA-1; IKK VII; adenosine receptor agonists; prostaglandin E2 agonists; phosphodiesterase inhibitors; proteasome inhibitors; kinase inhibitors; G-protein coupled receptor agonists; G-protein coupled receptor antagonists; glucocorticoids; retinoids; cytokine inhibitors; cytokine receptor inhibitors; cytokine receptor activators; peroxisome proliferator-activated receptor antagonists; peroxisome proliferator-activated receptor agonists; histone deacetylase inhibitors; calcineurin inhibitors; phosphatase inhibitors; PI3KB inhibitors; autophagy inhibitors; aryl hydrocarbon receptor inhibitors; proteasome inhibitor I (PSI); oxidized ATPs; IDO, vitamin D3; cyclosporins; aryl hydrocarbon receptor inhibitors; resveratrol; azathiopurine; 6-mercaptopurine; 6-thioguanine; FK506; sanglifehrin A; salmeterol; mycophenolate mofetil; aspirin and other COX inhibitors; niflumic acid; estriol; or triptolide.

7. The method of claim 4, wherein a loading of the immunosuppressant in the synthetic nanocarriers ranges between 0.0001 wt % and 50 wt %, based on the total dry recipe weight of materials in the synthetic nanocarrier (weight/weight).

8. The method claim 1, wherein the therapeutic macromolecule comprises a therapeutic protein or a therapeutic polynucleotide.

9. The method of claim 8, wherein the therapeutic protein comprises enzymes, enzyme cofactors, hormones, blood clotting factors, cytokines, growth factors, monoclonal antibodies or polyclonal antibodies.

10. The method of claim 1, wherein the administration pharmacodynamic effective-life has a duration that ranges from a minimum of 20 hours to a maximum of 2 weeks.

11. The method of claim 10, wherein the administration pharmacodynamic effective-life has a duration that ranges from a minimum of 20 hours to a maximum of 1 week.

12. The method of claim 11, wherein the administration pharmacodynamic effective-life has a duration that ranges from a minimum of 24 hours to a maximum of 2 days.

13. The method of claim 1, wherein the test pharmacodynamic effective-life has a duration that ranges from a minimum of 20 hours to a maximum of 2 weeks.

14. The method of claim 13, wherein the test pharmacodynamic effective-life has a duration that ranges from a minimum of 20 hours to a maximum of 1 week.

15. The method of claim 14, wherein the test pharmacodynamic effective-life has a duration that ranges from a minimum of 24 hours to a maximum of 2 days.

16. The method of claim 1, wherein the administration dose of the immunosuppressant is determined based on the test dose of the immunosuppressant, together with use of allometric or isometric scaling techniques.

17. The method of claim 1, wherein the first class of subjects and the second class of subjects are a same class of subjects.

18. The method of claim 1, wherein the first class of subjects and the second class of subjects are different classes of subjects.

19. The method of claim 1, wherein the mean of a particle size distribution obtained using dynamic light scattering of the synthetic nanocarriers is a diameter greater than 100 nm.

20. The method of claim 4, wherein an aspect ratio of the synthetic nanocarriers is greater than 1:1, 1:1.2, 1:1.5, 1:2, 1:3, 1:5, 1:7 or 1:10.

* * * * *

UNITED STATES PATENT AND TRADEMARK OFFICE
CERTIFICATE OF CORRECTION

| | |
|---|---|
| PATENT NO. | : 10,335,395 B2 |
| APPLICATION NO. | : 14/269058 |
| DATED | : July 2, 2019 |
| INVENTOR(S) | : Kishimoto |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 366 days.

Signed and Sealed this
Second Day of June, 2020

Andrei Iancu
*Director of the United States Patent and Trademark Office*